US009567644B2

(12) United States Patent
Chinnaiyan et al.

(10) Patent No.: US 9,567,644 B2
(45) Date of Patent: Feb. 14, 2017

(54) RAF GENE FUSIONS

(71) Applicant: THE REGENTS OF THE UNIVERSITY OF MICHIGAN, Ann Arbor, MI (US)

(72) Inventors: Arul Chinnaiyan, Plymouth, MI (US); Nallasivam Palanisamy, Ann Arbor, MI (US); Shanker Kalyana-Sundaram, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 18 days.

(21) Appl. No.: 14/589,543

(22) Filed: Jan. 5, 2015

(65) Prior Publication Data
US 2015/0191795 A1 Jul. 9, 2015

Related U.S. Application Data

(62) Division of application No. 13/300,063, filed on Nov. 18, 2011, now Pat. No. 8,945,556.

(60) Provisional application No. 61/415,495, filed on Nov. 19, 2010.

(51) Int. Cl.
*C12Q 1/68* (2006.01)
*G01N 33/574* (2006.01)

(52) U.S. Cl.
CPC ......... *C12Q 1/6886* (2013.01); *G01N 33/5748* (2013.01); *C12Q 2600/156* (2013.01); *C12Q 2600/158* (2013.01); *G01N 2333/91205* (2013.01)

(58) Field of Classification Search
None
See application file for complete search history.

(56) References Cited

U.S. PATENT DOCUMENTS

| 4,109,496 | A | 8/1978 | Allemann et al. |
|---|---|---|---|
| 4,323,546 | A | 4/1982 | Crockford |
| 4,683,195 | A | 7/1987 | Mullis et al. |
| 4,683,202 | A | 7/1987 | Mullis et al. |
| 4,800,159 | A | 1/1989 | Mullis et al. |
| 4,873,191 | A | 10/1989 | Wagner et al. |
| 4,965,188 | A | 10/1990 | Mullis et al. |
| 4,968,103 | A | 11/1990 | McNab et al. |
| 5,130,238 | A | 7/1992 | Malek et al. |
| 5,225,326 | A | 7/1993 | Bresser |
| 5,270,184 | A | 12/1993 | Walker et al. |
| 5,283,174 | A | 2/1994 | Arnold, Jr. et al. |
| 5,283,317 | A | 2/1994 | Saifer et al. |
| 5,399,491 | A | 3/1995 | Kacian et al. |
| 5,455,166 | A | 10/1995 | Walker et al. |
| 5,480,784 | A | 1/1996 | Kacian et al. |
| 5,545,524 | A | 8/1996 | Trent |
| 5,614,396 | A | 3/1997 | Bradley et al. |
| 5,631,169 | A | 5/1997 | Lakowicz et al. |
| 5,710,029 | A | 1/1998 | Ryder et al. |
| 5,776,782 | A | 7/1998 | Tsuji |
| 5,814,447 | A | 9/1998 | Ishiguro |
| 5,824,518 | A | 10/1998 | Kacian et al. |
| 5,854,206 | A | 12/1998 | Twardzik et al. |
| 5,856,125 | A | 1/1999 | Mavrothalassitis et al. |
| 5,925,517 | A | 7/1999 | Tyagi et al. |
| 5,928,862 | A | 7/1999 | Morrison et al. |
| 6,034,218 | A | 3/2000 | Reed et al. |
| 6,043,033 | A | 3/2000 | Bandman et al. |
| 6,080,912 | A | 6/2000 | Bremel et al. |
| 6,121,489 | A | 9/2000 | Dorner |
| 6,150,097 | A | 11/2000 | Tyagi et al. |
| 6,166,194 | A | 12/2000 | Wong |
| 6,198,107 | B1 | 3/2001 | Seville et al. |
| 6,262,245 | B1 | 7/2001 | Xu et al. |
| 6,303,305 | B1 | 10/2001 | Wittwer et al. |
| 6,350,448 | B1 | 2/2002 | Bandman et al. |
| 6,395,278 | B1 | 5/2002 | Xu et al. |
| 6,444,419 | B1 | 9/2002 | Wong |
| 6,534,274 | B2 | 3/2003 | Becker et al. |
| 6,541,205 | B1 | 4/2003 | Yokoyama et al. |
| 6,573,043 | B1 | 6/2003 | Cohen |
| 6,828,429 | B1 | 12/2004 | Srivastava et al. |
| 6,872,811 | B1 | 3/2005 | MacBeth et al. |
| 6,902,892 | B1 | 6/2005 | Salceda et al. |
| 7,008,765 | B1 | 3/2006 | Bussemakers et al. |
| 7,037,667 | B1 | 5/2006 | Afar et al. |
| 7,125,969 | B1 | 10/2006 | Benz et al. |
| 7,138,235 | B2 | 11/2006 | Bussemakers et al. |
| 7,199,137 | B2 | 4/2007 | Dean |

(Continued)

FOREIGN PATENT DOCUMENTS

| EP | 0684315 | 6/2002 |
|---|---|---|
| EP | 1409727 | 4/2004 |

(Continued)

OTHER PUBLICATIONS

Fischer et al., The Journal of Biological Chemistry, 2007, vol. 282 pp. 26503-26516.*
Tomlins et al., Nature, 2007, vol. 448, pp. 595-601.*
Cho et al., Int. J. Cancer, 2006, vol. 119, pp. 1858-1862.*
Mitelman et al., "Fusion genes and rearranged genes as a linear function of chromosome aberrations in cancer." Nat Genet. Apr. 2004;36(4):331-4.
Volik et al., "End-sequence profiling: sequence-based analysis of aberrant genomes." Proc Natl Acad Sci U S A. Jun. 24, 2003;100(13):7696-7701.
Ruan et al., "Fusion transcripts and transcribed retrotransposed loci discovered through comprehensive transcriptome analysis using Paired-End diTags (PETs)." Genome Res. Jun. 2007;17(6):828-38.
Hampton et al., "A sequence-level map of chromosomal breakpoints in the MCF-7 breast cancer cell line yields insights into the evolution of a cancer genome." Genome Res. Feb. 2009;19(2):167-77.
Hahn et al., "Finding fusion genes resulting from chromosome rearrangement by analyzing the expressed sequence databases." Proc Natl Acad Sci U S A. Sep. 7, 2004;101(36):13257-61.

(Continued)

*Primary Examiner* — Mindy G Brown
(74) *Attorney, Agent, or Firm* — Casimir Jones, S.C.

(57) ABSTRACT

The present disclosure relates to compositions and methods for cancer diagnosis, research and therapy, including but not limited to, cancer markers. In particular, the present disclosure relates to RAF gene fusions as diagnostic markers and clinical targets for cancer.

8 Claims, 17 Drawing Sheets

(56) References Cited

U.S. PATENT DOCUMENTS

| | | |
|---|---|---|
| 7,229,774 B2 | 6/2007 | Chinnaiyan |
| 7,374,885 B2 | 5/2008 | Becker et al. |
| 7,638,278 B2 | 12/2009 | Pollack |
| 7,718,369 B2 | 5/2010 | Tomlins et al. |
| 2002/0119531 A1 | 8/2002 | Bandman et al. |
| 2002/0182586 A1 | 12/2002 | Morris |
| 2002/0183251 A1 | 12/2002 | Xu et al. |
| 2003/0103981 A1 | 6/2003 | Spancake |
| 2003/0108963 A1 | 6/2003 | Schlegel et al. |
| 2003/0170625 A1 | 9/2003 | Rosenthal et al. |
| 2003/0175736 A1 | 9/2003 | Chinnaiyan et al. |
| 2003/0185830 A1 | 10/2003 | Xu et al. |
| 2004/0009481 A1 | 1/2004 | Schlegel et al. |
| 2004/0259086 A1 | 12/2004 | Schlegel et al. |
| 2005/0009086 A1 | 1/2005 | Salceda et al. |
| 2005/0042638 A1 | 2/2005 | Arnold, Jr. et al. |
| 2005/0112711 A1 | 5/2005 | Romano et al. |
| 2005/0164223 A1 | 7/2005 | Schalken et al. |
| 2005/0214309 A1 | 9/2005 | Hinrichs et al. |
| 2006/0019256 A1 | 1/2006 | Clarke et al. |
| 2006/0046265 A1 | 3/2006 | Becker et al. |
| 2006/0068425 A1 | 3/2006 | Monahan |
| 2006/0115821 A1 | 6/2006 | Einstein |
| 2006/0275794 A1 | 12/2006 | Carrino et al. |
| 2007/0042381 A1 | 2/2007 | Bentwich et al. |
| 2007/0212702 A1 | 9/2007 | Tomlins et al. |
| 2008/0269157 A1 | 10/2008 | Srivastava et al. |
| 2009/0170075 A1 | 7/2009 | Petrovics et al. |
| 2009/0208937 A1 | 8/2009 | Chinnaiyan |
| 2009/0239221 A1 | 9/2009 | Chinnaiyan et al. |
| 2010/0063088 A1 | 3/2010 | Wood |
| 2010/0305188 A1 | 12/2010 | Nakano |
| 2011/0065113 A1 | 3/2011 | Chinnaiyan et al. |
| 2013/0040858 A1 | 2/2013 | Tomlins et al. |

FOREIGN PATENT DOCUMENTS

| | | |
|---|---|---|
| WO | 9410300 | 5/1994 |
| WO | 9815837 A1 | 4/1998 |
| WO | 9845420 | 10/1998 |
| WO | 9962942 | 12/1999 |
| WO | 9965929 | 12/1999 |
| WO | 0000605 | 1/2000 |
| WO | 0004149 | 1/2000 |
| WO | 0012758 | 3/2000 |
| WO | 0018961 | 4/2000 |
| WO | 0023111 | 4/2000 |
| WO | 0000092 | 11/2000 |
| WO | 0065067 | 11/2000 |
| WO | 0153836 | 7/2001 |
| WO | 0157058 | 8/2001 |
| WO | 0160860 | 8/2001 |
| WO | 0188124 | 11/2001 |
| WO | 0210443 A1 | 2/2002 |
| WO | 03009814 | 2/2003 |
| WO | 03011888 A1 | 2/2003 |
| WO | 03053223 | 7/2003 |
| WO | 2004070056 A2 | 2/2004 |
| WO | 2004023973 | 3/2004 |
| WO | 2004074320 | 9/2004 |
| WO | 200492397 | 10/2004 |
| WO | 2004097358 | 11/2004 |
| WO | 2004113571 | 12/2004 |
| WO | 2005007090 | 1/2005 |
| WO | 2005007830 | 2/2005 |
| WO | 2005003387 | 3/2005 |
| WO | 2005113816 | 12/2005 |
| WO | 2006028655 | 3/2006 |
| WO | 2007033187 A | 3/2007 |
| WO | 2009009432 | 1/2009 |
| WO | 2010096660 | 8/2010 |

OTHER PUBLICATIONS

Shadeo & Lam. "Comprehensive copy number profiles of breast cancer cell model genomes." Breast Cancer Res. 2006;8(1):R9.

Neve et al., "A collection of breast cancer cell lines for the study of functionally distinct cancer subtypes." Cancer Cell. Dec. 2006;10(6):515-27.

Bodmer et al., "Disruption of a novel MFS transporter gene, DIRC2, by a familial renal cell carcinoma-associated t (2;3)(q35;q21)." Hum Mol Genet. Mar. 15, 2002;11(6):641-9.

Montagut et al., "Targeting the RAF-MEK-ERK pathway in cancer therapy." Cancer Letters Feb. 2009, 283 (2):125-134.

Sjolander et al., "Integrated fluid handling system for biomolecular interaction analysis." Anal Chem. Oct. 15, 1991;63(20):2338-45.

Szabo et al., "Surface plasmon resonance and its use in biomolecular interaction analysis (BIA)." Curr Opin Struct Biol. Oct. 1995;5(5):699-705.

In situ hybridization in neurobiology: advances in methodology. Edited by Eberwine, Valentino, Barchas. Oxford University Press Inc., England 1994.

In situ hybridization : medical applications, Edited by G.R. Coulton and J. de Belleroche. Kluwer Academic Publishers, Boston 1992.

In Situ Hybridization: A Practical Approach. Edited by D. G. Wilkinson. Oxford University Press, USA, 1992.

Huang et al., "Whole genome DNA copy number changes identified by high density oligonucleotide arrays." Hum Genomics. May 2004;1(4):287-99.

Barlund et al., "Cloning of BCAS3 (17q23) and BCAS4 (20q13) genes that undergo amplification, overexpression, and fusion in breast cancer." Genes Chromosomes Cancer. Dec. 2002;35(4):311-7.

Tuzun et al., "Fine-scale structural variation of the human genome" Nat Genet. Jul. 2005;37(7):727-32.

Mitelman et al., "Prevalence estimates of recurrent balanced cytogenetic aberrations and gene fusions in unselected patients with neoplastic disorders." Genes Chromosomes Cancer. Aug. 2005;43(4):350-66.

Smith et al., "Cloning, expression, and characterization of a soluble calcium-activated nucleotidase, a human enzyme belonging to a new family of extracellular nucleotidases." Arch Biochem Biophys. Oct. 1, 2002;406(1)105-15.

Wood et al., "The genomic landscapes of human breast and colorectal cancers." Science. Nov. 16, 2007;318 (5853):1108-13.

Soda et al., "Identification of the transforming EML4-ALK fusion gene in non-small-cell lung cancer." Nature. Aug. 2, 2007;448(7153):561-6.

Pfluger, D. Towards Understanding of Prostate Cancer Heterogenity. Master Thesis. Universitat Ulm and Weill Cornell Medical College. 2008. 58 pages.

Einhauer et al., "The Flag peptide, a versatile fusion tag for the purification of recombinant proteins." J Biochem Biophys Methods. Oct. 30, 2001;49(1-3):455-65.

Illum & Jones, "Attachment of monoclonal antibodies to microspheres." Methods Enzymol. 1985; 112:67-84.

Joosten et al., "The production of antibody fragments and anitbody fusion proteins by yeasts and filamentous fungi." Microbial Cell Factories 2003, 2:1-15.

Palanisamy, N. "Rearrangements of the RAF kinase pathway in prostate cancer, gastric cancer and melanoma." Nature Medicine 2010 16(7):793-798.

RAF Family Antibody Sampler Kit #2330, Cell Signaling Technology, downloaded from: http://www.cellsignal.com/products/2330.html on May 16, 2013.

Wang et al., "Identification and characterization of AGTRAP, a human homolog of murine Angiotensin II Receptor-Associated Protein (Agtrap)" Intl. J Biochem. & Cell Biology 2002, 34:93-102.

CA Office Action Issued Mar. 29, 2011 (Application No. 2692441).

Edwards et al., "Expression analysis onto microarrays of randomly selected cDNA clones highlights HOXB13 as a marker of human prostate cancer." Br J Cancer. Jan. 31, 2005;92(2):376-81.

Gao et al., "Combinatorial activities of Akt and B-Raf/Erk signaling in a mouse model of androgen-independent prostate cancer." Proc Natl Acad Sci U S A. Sep. 26, 2006;103(39):14477-82.

Genbank Accession No. NT_086880.1, 3 pages, Aug. 20, 2004.

He, et al., "Profile of Ets gene expression in human breast carcinoma." Cancer Biol Ther. Jan. 2007;6(1):76-82.

(56) References Cited

OTHER PUBLICATIONS

Kumar-Sinha Al., "SLC45A3-ELK4 chimera in prostate cancer: spotlight on cis-splicing." Cancer Discov. Jul. 2012;2 (7):582-5.
Makkonen et al., "Identification of ETS-like transcriptome factor 4 as a novel androgen receptor target in prostate cancer cells." Oncogene May 12, 2008, 27(36): 4865-4876.
NEB Catalog, 1998/99, pp. 121 and 284.
Park et al., "Antibody-Based Detection of ERG Rearrangement-Positive Prostate Cancer." Neoplasia Jul. 2010, 12(7): 590-598.
Schmidt et al., "Quantitative Multi-Gene Expression Profiling of Primary Prostate Cancer." The Prostate 66:1521-1534.
Singh et al., "Genome-wide expression profiling reveals transcriptomic variation and perturbed gene networks in androgen-dependent and androgen-independent prostate cancer cells." Cancer Lett. Jan. 18, 2008;259(1):28-38.
Strausberg et al., "The cancer genome anatomy project: building an annotated gene index." Trends Genet. Mar. 2000;16(3):103-6.
Sun et al., "TMPRSS2-ERG fusion, a common genomic alteration in prostate cancer activates C-MYC and abrogates prostate epithelial differentiation." Oncogene Jun. 9, 2008, 27(40):5348-5353.
Wilson et al., "The membrane-anchored serine protease, TMPRSS2, activates PAR-2 in prostate cancer cells" Biochem. J. (2005) 388: 967-972.
Zucman et al., "Combinatorial generation of variable fusion proteins in the Ewing family of tumours." EMBO Journal 1993, 12(12): 4481-4487.
Forrest et al. Cancer Genet Cytogenet 181-183.
Tomlins, et al., "Recurrent Fusion of TMPRSS2 and ETS Transcription Factor Genes in Prostate Cancer", Science, vol. 310, No. 5748, Oct. 28, 2005, pp. 644-648.
Tomlins, et al., "TMPRSS2: ETV4 Gene Fusions Define a Third Molecular Subtype of Prostate Cancer", Cancer Research 2006; 66: (7), Apr. 1, 2006, pp. 3396-3400.
Tusher et al., "Significance analysis of microarrays applied to the ionizing radiation response," PNAS vol. 98, No. 9, Apr. 24, 2001, pp. 5116-5121.
Vasselli, et al., "Predicting survival in patients with metastatic kidney cancer by gene-expression profiling in the primary tumor", PNAS, vol. 100, No. 12, Jun. 10, 2003, pp. 6858-6963.
Velasco, et al., "Identification and validation of novel androgen-regulated genes in prostate cancer", Endocrinology vol. 145(8), 2004, pp. 3913-3924.
Wang, et al., "Gene-expression profiles to predict distant metastasis of lymph-node-negative primary breast cancer", The Lancet, vol. 365, No. 9460, Feb. 19-25, 2005, pp. 671-679.
Welsh, et al., "Analysis of gene expression identifies candidate markers and pharmacological targets in prostate cancer", Cancer Research, vol. 61, Aug. 15, 2001, pp. 5974-5978.
Wigle, et al., "Molecular profiling of non-small cell lung cancer and correlation with disease-free survival", Cancer Research, vol. 62, Jun. 1, 2002, pp. 3005-3008.
Yoshimoto, et al., Three-color FISH analysis of TMPRSS2/ERG fusions in prostate cancer indicates that genomic microdeletion of chromosome 21 is associated with rearrangement, Neoplasia, vol. 8, No. 6, Jun. 2006, pp. 465-469.
Zhan, et al., "Global gene expression profiling of multiple myeloma, monoclonal gammopathy of undetermined significance, and normal bone marrow plasma cells", Blood, vol. 99, No. 5, Mar. 1, 2002, pp. 1745-1757.
Abdulkadir, Sarki A., "Conditional Loss of Nkx3.1 in Adult Mice Induces Prostatic Intraepithelial Neoplasia," Molecular and Cellular Biology, Mar. 2002, pp. 1495-1503.
Antoniou, Michael, et al., "Transgenes encompassing dual-promoter CpG islands from the human TBP and HNRPA2B1 loci are resistant to geterochromatin-mediated silencing", Genomics, vol. 82, 2003, pp. 269-279.
Attard, G., et al., "Duplication of the fusion of TMPRSS2 to ERG sequences identifies fatal human prostate cancer", Onogene vol. 27, 2008, pp. 253-263.

Beheshti, B., et al., "Identification of a high Frequency of Chromosomal Rearrangements in the Centromeric Regions of prostate Cancer Cell Lines by Sequential Giemsa Banding and Spectral Karyotyping", Molecular Diagnosis, vol. 5, No. 1,2000, pp. 23-32.
Beheshti, Ben, et al., "Evidence of Chromosomal Instability in Prostate Cancer Determined by Spectral Karyotyping (SKY) and Interphase Fish Analysis", Neoplasia, vol. 3, No. 1, 2001, pp. 62-69.
Cai, Changmeng, et al., "ETV1 is a Novel Androgen Receptor-Regulated Gene that Mediates Prostate Cancer Cell Invasion", Molecular Endocrinology, May 15, 2007, 21 (8), pp. 1835-1846.
Di Cristofano, Antonio, et al., "Pten and p27KIP1 cooperate in prostate cancer tumor suppression in the mouse", Nature Genetics, vol. 27, Feb. 2001, pp. 222-224.
Eisenberg, Eli and Levanon, Erez Y., "Human housekeeping genes are compact", Trends in Genetics, vol. 19, No. 7, Jul. 2003, pp. 362-365.
Fingleon, Barbara, "Matrix metalloproteinases: roles in cancer and metastasis", Frontiers in Bioscience, vol. 11, Jan. 1, 2006, pp. 479-491.
Gibas, Zenon, "A high-Resolution Study of Chromosome Changes in a Human Prostatic Carcinoma Cell Line (LNCaP)", Cancer Genetics and Cytogenetics 1984, vol. 11, p. 399-404.
Guasch, Geraldine, et al., "Endogenous retroviral sequence is fused to FGFR1 kinase in the 8p12 stem-cell myeloproliferative disorder with t(8;19)(p12;q13.3)", Blood, vol. 10, No. Jan. 1, 2003, pp. 286-288.
Kalos, Michael, et al, "Prostein Expression is highly Restricted to Normal and Malignant Prostate Tissues", The Prostate 60:246-256 (2004).
Kim, Minjung, et al., "Cooperativity of Nkx3.1 and Pten loss of function in a mouse model of prostate carcinogenesis", PNAS, Mar. 5, 2002, vol. 99, No. 5, pp. 2884-2778.
Mirosevich, Janni, et al., "Expression and role of Foxa proteins in Prostate Cancer", the Prostate 66:1013-1028 (2006).
Mirosevich, Janni, et al., "Expression of Foxa Transcription Factors in the Developing and Adult Murine Prostate", The Prostate 62:339-352 (2005).
Murillo, Horacio, et al., "Prostate Cancer Cells use Genetic and Epigenetic mechanisms for Progression to Androgen Independence", Genes, Chromosomes 7 Cancer, 2006, pp. 702-716.
Ono, Masao, et al., "Stimulation of Expression of the Human Endogenous retrovirus Genome by Female Steroid Hormones in Human Breast Cancer Cell Line T47D", Journal of Virology, Jun. 1987, pp. 2059-2062.
Pang, See-Tong, et al., "Cytogenetic and Expression profiles Associated with Transformation to Androgen-Resistant Prostate Cancer", the Prostate 66: 157-172 (2006).
Patience, Clive, et al., "Human Endogenous Retrovirus Expression and Reverse Transcriptase Activity in the T47D Mammary Carcinoma Cell Line", Journal of Virology, Apr. 1996, pp. 2654-2657.
Weigle, Bernd, et al., "D-PCa-2: A Novel Transript Highly Overexpressed in Human prostate and Prostate Cancer", International Journal of Cancer, vol. 109, 2004, pp. 882-892.
Shai, Xu-Bao, et al., "Molecular Alterations Associated With LNCaP Cell Progression to Androgen Indpendence", The Prostate 60:257-271 (2004).
Smith, Richard, et al., "Expression profiling of EWS/FLI identifies NKX2.2 as a critical target gene in Ewing's sarcoma", Cancer Cell, vol. 9, May 2006, pp. 405-416.
Stauffer, Yves, et al, Digital Expression profiles of human endogenous retroviral families in normal and cancerous tissues, Cancer Immunity 4:2 (2004).
Stavenhagen, Jeffrey B. and Robins, Diane M., "An Ancient Provirus Has Imposed Androgen Regulation on the Adjacent Mouse Sex-Limited Protein Gene", Cell, vol. 55, No. 2, Oct. 21, 1988, pp. 247-254.
Stefford, Jon C., The use of multicolor fluorescence technologies in the characterization of prostate carcinoma cell lines: a comparison of multiplex fluorescence in situ hybridization and spectral karyotyping data, Cancer Genetics and Cytogenetics, vol. 124, 2001, pp. 112-121.
Suzukawa, Kazumi, et al., "Identification of a Breakpoint Cluster Region 3' of the Ribophorin I Gene at 3q21 Associated With the

(56) References Cited

OTHER PUBLICATIONS

Transcriptional Activation of the EVI1 Gene in Acute Myelogenous Leukemias With inv(3) (q21q26)", Blood, vol. 84, No. 8, Oct. 15, 1994, pp. 2681-2688.
Takaha, Natsuki, et al., "High Mobility Group Protein I(Y): A Candidate Architectural protein for Chromosomal Rearrangements in Prostate Cancer Cells", Cancer Research vol. 62, Feb. 1, 2002, pp. 647-651.
Thalmann, George N., "Androgen-independent Cancer Progression and Bone Metastasis in the LNCaP Model of Human Prostate Cancer", Cancer Research, vol. 54, May 15, 1994, pp. 2577-2581.
Tomlins, Scott A., et al., "Integrative Biology of Prostate Cancer Progression", Annual Review of pathology: Mechanisms of Disease, vol. 1, 2006, pp. 243-271.
Van Bokhoven, Adrie, et al., "Spectral Karyotype (SKY) Analysis of Human Prostate Carcinoma Cell Lines", The Prostate 57:226-244 (2003).
Wang-Johanning, Feng, et al., "Quantitation of HERV-K env gene expression and splicing in human breast cancer", Onogene(2003)22,pp. 1528-1535.
Watson, Spencer K., et al., "Cytogenetically balanced translocations are associated with focal copy number alterations", Hum Genet (2007) 120, pp. 795-805.
Wieser, "Rearrangements of Chromosome Band 3q21 in Myeloid Leukemia." Leukemia & Lymphoma Jan. 2002, 43(1): 59-65.
Williams, Steven, et al., "CpG-island fragments from the HNRPA2B1/CBX3 genomic locus reduce silencing and enhance transgene expression from the hCMV promoter/enhancer in mammalian cells", BMC Biotechnology, 2005, 5:17,9 pages.
Xu, Jiangchun, et al., "Identification and Characterization of Prostein, a Novel Prostate-specific Protein", Cancer Research, vol. 61, Feb. 15, 2001, pp. 1563-1568.
Tomlins, Scott A., et al., "Integrative molecular concept modeling of prostate cancer progression", Nature Genetics, vol. 39, No. 1, Jan. 2007, pp. 41-51.
Hartel, et al., "Characterisation of steroid receptor expression in the human prostate carcinoma cell line 22RV1 and quantification of androgen effects on mRNA regulation of prostate-specific genes," The Journal of Steroid Biochemistry & Molecular Biology 2004, vol. 92(3): pp. 187-197.
Schroeder (2007) European Urology 53:208-11 (2008) Comments on Attard et al. (2007), "Duplication of the Fusion of TMPRSS2 to ERG sequences identifies Fatal Human Prostate Cancer", Onogene 2007; 1-11.
Kumar-Sinha Chandan et al., "Evidence of Recurrent Gene Fusions in Common Epithelial Tumors," Trends in Mol. Medicine, Nov. 2006, 12(11):529-536.
Perner Sven et al., "TMPRSS2-ERG fusion prostate cancer: an early molecular event associated with invasion," The American Journal of Surgical Pathology, Jun. 2007. vol. 31(6), pp. 882-888.
Nam Robert K et al., "Expression of TMPRSS2: ERG gene fusion in prostate cancer cells is an important prognostic factor for cancer progression," Cancer Biology & Therapy Jan. 2007, vol. 6, pp. 40-45.
Walker Michael G. et al., "Prediction of gene function by genome-scale expression analysis: Prostate cancer-associated genes" vol. 9, pp. 1198-1203, Dec. 1, 1999.
Kumar-Sinha Chandan et al., "Recurrent gene fusions in prostate cancer." Nature reviews, Cancer (Jul. 2008) 8 (7):497-511.
Tomlins Scott A. et al, "Distinct classes of chromosal rearrangements create oncogenic ETS gene fusions in prostate cancer," Nature 2, Aug. 2007, vol. 448, pp. 595-599.
Helgeson Beth et al., "Characterization of TMPRSS2: ETV5 and SLC45A3: ETV5 gene fusions in prostate cancer," Cancer Research Jan. 1, 2008, vol. 68, pp. 73-80.
Seton-Rodgers, "Breast cancer: A striking resemblance" (Nature Reviews) Sep. 2007, vol. 7, p. 638.
Morris et al, (2008), "The discovery and application of gene fusions in prostate cancer," BJU International, vol. 102 p. 276-82.
Rickman et al., (2009) "SLC45A3-ELK4 is a novel and frequent erythroblast transformation-specific fusion transcript in prostate cancer," Cancer Research, 69, p. 2734-2738.
Han Bo et al., "A Fluorescence in Situ Hybridization Screen for E26 Transformation-Specific Aberrations: Identification of DDX5-ETV4 Fusion Protein in Prostate Cancer" Cancer Research Sep. 2008 68(18):7629-7637.
Hermans Karing G et al., "Truncated ETV1, Fused to Novel Tissued-Specific Genes, and Full Length ETV1 in Prostate Cancer" Cancer Research Sep. 2008 68:7541-7549.
Plueger Dorothee et al., "N-MYC Downstream Regulated Gene 1 (NDRG1) is fused to ERG in Prostate Cancer." Neoplasia (Aug. 2009) 11(8):804.
Kamnasaran, Deepak et al., "Rearrangment in the PITX2 and MIPOL1 genes in a patient with a t(4;14) chromosome." European Journal of Human Genetics: EJHG, Apr. 11, 2003(4)315-324.
Singh, Jas et al., "Annotation of androgen dependence to human prostate cancer associated genes by microarray analysis of mouse prostate" Cancer Letters 2006, 237:298-304.
Singh, Jas et al., "RNA Reference mediated silencing of SPINK reduces invasion and proliferation of prostate cancer cells." Proceedings of the Annual Meeting of the American Association for Cancer Research, (Apr. 2006) 47 (1):823 US.
Bjartell, A. et al., "Tumor-Associated Trypsin Inhibitor (TATI, PSTI, SPINK1) Expression in Prostate Cancer is Related to Tumor Grade" European Urology Supplements (Sep. 2006) 5(14):79.
Li Shijun et al., "Application of genomic technologies to human prostate cancer" OMICS A Journal of Integrative Biology (Sep. 2006) 10(3):261-275.
Laxman, Bharathi, et al., "A First-Generation Mulitplex Biomarker Analysis of Urine for the Early Detection of Prostate Cancer." Cancer Research (Feb. 2008) 68(3):645-649.
Rhodes et al., "Large-scale meta-analysis of cancer microarray data identifies common transcriptional profiles of neoplastic transformation and progression" Proc Natl Acad Sci USA (2004) 101:9309.
Haverback et al., "Trypsin, Trypsinogen and Trypsin Inhibitor in Human Pancreatic Juice." Am J. Med. (1960) 29:421-433.
Kazal et al., "Isolation of a Crystalline Trypsin Inhibitor-Anticoagulant Protein from Pancreas." Journal of the American Chemical Society (1948) 70:3034-3040.
Paju et al., "Biochemistry and Clinical Role of Trypsinogens and Pancreatic Secretory Trypsin Inhibitor." Crit. Rev. Clin. Lab Sci. (2006) 43:103-42.
Greene et al., "Human Pancreatic Secretory Trypsin Inhibitor." Methods Enzymol (1976) 45:813-25.
Stenman, "Tumor-associated Trypsin Inhibitor." Clin Chem (2002) 48:1206-9.
Schalken, "Molecular Diagnostics and Therapy of Prostate Cancer: New Avenues." Eur. Urol 1998 34 (Suppl.3):3-6.
Bussemakers et al., "DD3:A new Prostate-specific Gene, Highly Overexpressed in Prostate Cancer," Cancer Res. (1999) 59:5975-5979.
Bussemakers et al., "Changes in Gene Expression and Targets for Therapy." Eur. Urol. (1999) 35:408-412.
De Kok et al., "DD3PCA3, a Very Sensitive and Specific Marker to Detect Prostate Tumors." Cancer Res. (2002) 2695-8.
Block et al., "Use of targeted glycoroteomics to identify serum glycoproteins that correlate with liver cancer in woodchucks and humans." Proc Natl Acad Sci USA (2005) 102:779-784.
Kladney et al., "GP73, a novel Golgi-localized protein unregulated by viral infection." Gene 2000 249:53-65.
Yu et al., "Gene expression Alterations in Prostate Cancer Predicting Tumor Aggression and Preceding Development of Malignancy." J Clin Onc (Jul. 2004) 22(14):2790-2799.
Glinsky et al., "Gene expression profiling predicts clinical outcome of prostate cancer." J Clin Invest (2004) 113:913-23.
Vanaja et al., "Transcriptional Silencing of Zinc Finger Protein 185 Identified by Expressing Profiling is Associated with Prostate Cancer Progression." Cancer Res (2003) 63:3877-82.
Dhanasekaran et al., "Delineation of prognostic biomarkers in prostate cancer." Nature (2001) 412:822-6.
Bittner et al., "A window on the dynamics of biological switches." Biotechnol. (2005) 23:183-4.

(56) References Cited

OTHER PUBLICATIONS

Su et al., "Molecular Classification of Human Carcinomas by Use of Gene Expression Signatures." Cancer Res (2201) 61:7388-93.
Andren et al., "How Well Does the Gleason Score Predict Prostate Cancer Death? A 20-Year Follow up of a Population Based Cohort in Sweden." J Urol (2006) 175:1337-40.
Johansson et al., "Natural History of Early, Localized Prostate Cancer." JAMA (2004) 291: 2713-9.
Han et al., "Long-term Biochemical Disease-Free and Cancerspecific Survival Following Anatomic Radical Retropubic Prostatectomy." Urol Clin North Am (2001) 28:555-65.
Hull et al., "Cancer Control with Radical Prostatectomy Alone in 1,000 Consecutive Patients." J. Urol (2002) 167:528-34.
Kattan et al., "Postoperative Nomogram for Disease Recurrence After Radical Prostatectomy for Prostate Cancer." J. Clinical Oncol. (1999) 17:1499-507.
Kattan et al., "The Addition of Interleukin-6 Soluble Receptor and Transforming Growth Factor Beta1 Improves a Preoperative Nomogram for Predicting Biochemical Progression in Patients with Clinically Localized Prostate Cancer." J Clin Oncol (2003) 21:3537-9.
Paju et al., "Increased Expression of Tumor-Associated Trypsin Inhibitor, TATI, in Prostate Cancer and in Androgen-Independent 22Rv1 Cells." Eur Urol (2007) 52:1670-1681.
Sramkoski, R.M. et al., "A New Human Prostate Carcinoma Cell Line 22RV1." In Vitro Cell Dev Biol Anim (1999) 35:403-9.
Tomlins et al., "Whole Transcriptome Amplification for Gene Expression Profiling and Development of Molecular Archives." Neoplasia (2006) 8:153-62.
Vandesompele et al., "Accurate normalization of real-time quantitative RT-PCR data by geometric averaging of multiple internal control genes." Genome Biol 2002; 3 Research 0034.1-0034.11.
Kumar-Sinha et al., "Elevated Alpha-Methylacyl-CoA Racemase Enzymatic Activity in Prostate Cancer." Am J. Path (2004) 164:787-93.
Specht et al., "Quantitative Gene Expression Analysis in Microdissected Archival Formalin-Fixed and Paraffin-Embedded Tumor Tissue." Am J. Pathol. 2001, 158:419-29.
Rubin et al., "alpha Methylacyl Coenzyme A Racemase as a Tissue Biomarker for Prostate Cancer." JAMA (2002) 287:1662-70.
Faith et al., "Trefoil Factor 3 Overexpression in Prostate Carcinoma: Prognostic Importance Using Tissue Microarrays." Prostate (2004) 61:215-27.
Garraway et al., "Trefoil Factor 3 is Overexpressed in Human Prostate Cancer." Prostate 2004 61:209-14.
Hessels et al., "DD3PCA3-based Molecular Urine Analysis for the Diagnosis of Prostate Cancer." Eur Urol (2003) 44:8-15.
Fradet et al., "UPM3, A new molecular urine test for the detection of Prostate Cancer." Urology (2004) 64:311-5.
Groskopf et al., "APTIMA PCA3 Molecular Urine Test: Development of a Method to Aid in the Diagnosis of Prostate Cancer." Clin Chem 2006 52:1089-95.
Marks et al., "PCA3 Molecular Urine Assay for Prostate Cancer in Men Undergoing Repeat Biopsy." Urology (2007) 69:532-5.
Delong et al., "Comparing the Areas Under Two or More Correlated Receiver Operating Characteristic Curves: A Nonparametric Approach." Biometrics (1988) 44:837-45.
Affymetrix NETAFXX Details for MG-U74AV2 Microarray Specifically Showing that ETV1 is present on the array accessed from www.affymetrix.com on May 1, 2009.
Affymetrix NETAFXX Details for MG-U74AV2 Microarray Specifically Showing that ERG is present on the array accessed from www.affymetrix.com on May 1, 2009.
Affymetrix NETAFXX Details for MG-U74AV2 Accessed from www.affymetrix.com on Aug. 18, 2008.
Database EMBL (Online) Mar. 2, 2007 "140298_1373_0575 3' ESTs from HeLa cell *Homo sapiens* Cdna 3', mRNA sequence." XP002597931 retrieved from EBI accession No. EMBL:EH3299833 Nucleotides 2-11.
Wallace, James C. et al., "High-density rhesus macaque Oligonucleotide Microarray design using early-stage rhesus genome sequence information and human genome annotations." BMC Genomics (Jan. 2007) v.8.
Database Entrez Nucleotide (Online) Sep. 21, 2008, "*Homo sapiens* solute carrier family 45, member 3 (SLC45A3), mRNA; version NM_033102.2 GI: 93277086" Accession No. NM033102 nucleotides 1525-1563 (A).
Tognon Cristina et al., "Expression of the ETV6-NTRK3 gene fusion as a primary event in human secretory breast carcinoma" Cancer Cell (Nov. 2002) 2(5):367-376 (X).
Maher, Christopher, et al., "Transcriptome sequencing to detect gene fusions in cancer." Nature (Mar. 2009) 458(7234):97-101.
Maher, Christopher, et al., "Chmimeric transcript discovery by paird-end transcriptome sequencing" Proceedings of the National Academy of Sciences of the United States of America (Jul. 2009) 106(30):12353-12358.
U.S. Office Action Mailed: Sep. 29, 2010 (Sep. 29, 2010), U.S. Appl. No. 12/272,865, filed Nov. 18, 2008 (Nov. 18, 2008) 20 Pages.
International Search Report Mailed: May 25, 2010 (May 25, 2010), Application No. PCT/US2009/064957; Filing Date: Nov. 18, 2009 (Nov. 18, 2009) WIPO Publication No. WO 2010/059702 (9 Pages).
Australian Further Office Action Mailed: Jan. 18, 2011 (Jan. 18, 2011), Application No. 2006291054; Filing Date: Sep. 12, 2006 (Sep. 12, 2006) 2 Pages.
Australian Office Action Mailed: Dec. 23, 2009 (Dec. 23, 2009), Application No. 2006291054; Filing Date: Sep. 12, 2006 (Sep. 12, 2006) 3 Pages.
Canadian Office Action Mailed: Nov. 16, 2010 (Nov. 16, 2010), Application No. 2,662,295; Filing Date: Sep. 12, 2006 (Sep. 12, 2006) 11 Pages.
Chinese Office Action Mailed: Dec. 31, 2010 (Dec. 12, 2010), Application No. 200680041826.6; Filing Date: Sep. 12, 2006 (Sep. 12, 2006) Publication No. 101341256 (8 Pages).
U.S. Final Office Action Mailed: Aug. 13, 2009, (Aug. 13, 2009), U.S. Appl. No. 11/519,397, filed Sep. 12, 2006 (Sep. 12, 2006) 36 Pages.
U.S Office Action Mailed: Feb. 23, 2009 (Feb. 23, 2009), U.S. Appl. No. 11/519,397, filed Sep. 12, 2006 (Sep. 12, 2006) 50 Pages.
International Search Report Mailed: Dec. 4, 2007 (Dec. 4, 2007), Application No. PCT/US2006/035507; Filing Date: Sep. 12, 2006 (Sep. 12, 2006); WIPO Publication No. WO 2007/033187 (5 Pages).
European Office Action Mailed: May 5, 2010 (May 5, 2010), Application No. 08826146.6; Filing Date: Jul. 3, 2008 (Jul. 3, 2008); Publication No. 2171094 (23 Pages).
International Search Report Mailed: Jan. 30, 2009 (Jan. 30, 2009), Application No. PCT/2008/069201; Filing Date: Jul. 3, 2008 (Jul. 3, 2008); WIPO Publication No. WO 2009/009431 (5 Pages).
U.S. Office Action Mailed: Feb. 1, 2011 (Feb. 1, 2011), U.S. Appl. No. 11/825,552, filed Jul. 6, 2007 (Jul. 6, 2007) ; Publication No. 2009-0208937 (20 Pages).
U.S. Office Action Mailed: May 26, 2010 (May 26, 2010), U.S. Appl. No. 11/825,552, filed Jul. 6, 2007 (Jul. 6, 2007); Publication No. 2009-0208937 (61 Pages).
International Search Report Mailed: Apr. 15, 2009 (Apr. 15, 2009); Application No. PCT/US2008/069204; Filing Date: Jul. 3, 2008 (Jul. 3, 2008); WIPO Publication No. WO 2009/009432 (8 Pages).
Australian Office Action Mailed: Nov. 5, 2010 (Nov. 5, 2010); Application No. 2007317306; Filing Date: Nov. 8, 2007 (Nov. 8, 2007) 2 Pages.
Canadian Office Action Mailed: Jan. 6, 2011 (Jan. 6, 2011); Application No. 2,668,961; Filing Date: Nov. 8, 2007 (Nov. 8, 2007) 5 Pages.
European Office Action Mailed: Aug. 17, 2010 (Aug. 17, 2010); Application No. 07864115.6; Filing Date: Nov. 8, 2007 (Nov. 8, 2007) Publication No. 2079851 (9 Pages).
International Search Report Mailed: Jul. 28, 2009 (Jul. 28, 2009); Application No. PCT/US2007/084090; Filing Date: Nov. 8, 2007 (Nov. 8, 2007) WIPO Publication No. WO 2008/058239 (5 Pages).
International Search Report Mailed: Nov. 5, 2010 (Nov. 5, 2010); Application No. PCT/US2010/020501; Filing Date: Jan. 8, 2010 (Jan. 8, 2010); WIPO Publication No. WO 2010/081001 (9 Pages).

(56) References Cited

OTHER PUBLICATIONS

Goodsell DS (1999), "The Molecular Perspective: The ras Oncogene," Oncologist 4(3): 263-4.
Downward J, ( 2003), "Targeting RAS signalling pathways in cancer therapy," Nat Rev Cancer 3(1): 11-22.
Wennerberg et al., 2005, "The Ras super-Family at a glance," J. Cell Sci, 118 (PT 5): 843-6.
Munemitsu et al., 1990, "Molecular Cloning and Expression of a G25K cDNA, the Human Homolog of the Yeast Cell Cycle Gene CDC42," Mol Cell Biol 10(11): 5977-82.
Sithanandam et al, "Complete coding sequence of a human B-raf cDNA and detection of B-raf protein kinase with isozyme specific antibodies," (1990) Oncogene 5(12): 1775-80.
Sithanandam et al, ( 1992), "B-raf and a B-raf pseudogene are located on 7q in man," Oncogene, 7 (4) 795-9.
Davies et al, 2002, "Mutations of the BRAF gene in human cancer," Nature 417, (6892): 949-54.
Mark et al, (Apr. 1984), "Primary structure of v-raf: relatedness to the src family of oncogenes," Science 224 (4646) 285-9.
Shimizu et al, (1986), "Structure of the activated c-raf-1 gene from human stomach cancer," Princess Takamatsu Symp, 17: 85-91.
Sridhar et al, ( 2005), "Raf kinase as a target for anticancer therapeutics," Mol Cancer Ther 4(4): 677-85.
Burns, R. (ed.), Immunochemical Protocols, 3rd Ed., Humana Press, 2005.
Harlow and Lane, Antibodies: A Laboratory Manual,, Cold Spring Harbor Laboratory (1988).
Kozbor et al, "The production of monoclonal antibodies from human lymphocytes," Immunology Today 4: 72-79 (1983).
Kohler and Milstein, (1975), "Continuous cultures of fused cells secreting antibody of predefined specificity," Nature 256: 495-497.
Mullis et al, (1987), Specific synthesis of DNA in vitro via a polymerase-catalyzed chain reaction, Meth Enzymol 155: 335-350.
Murakawa et al, (1988), "Direct detection of HIV-1 RNA from AIDS and ARC patient samples," DNA 7: 287-295.
Weiss, (1991), "Hot prospect for new gene amplifier," Science 254: 1292-1293.
Cheung et al., "Integration of cytogenetic landmarks into the draft sequence of the human genome." Nature 2001, 409:953-958.
Kuo et al., "Detection of aneuploidy involving chromosomes 13, 18, or 21, by fluorescence in situ hybridization (FISH) to interphase and metaphase amniocytes." Am. J. Human Genet. 1991, 49:112-119.
Ward et al., "Rapid prenatal diagnosis of chromosomal aneuploidies by fluorescence in situ hybridization: clinical experience with 4,500 specimens." Am. J. Hum. Gen. 1993, 52:854-865.
Persing, David H. "In Vitro Nucleic Acid Amplification Techniques" Diagnostic Medical Microbiology: Principles and Applications 1993, 51-87.
Liu et al., "Lineage Relationship between LNCaP and LNCaP-Derived Prostate Cancer Cell Lines." The Prostate 2004, 60:98-108.
Pettus et al., "Multiple abnormalities detected by dye reversal genomic microarrays in prostate cancer: A much greater sensitivity than conventional cytogenetics." Cancer Genet. Cytogent. 2004, 154(2):110-118.
Jarayaman et al., "p300/cAMP-responsive Element-binding Protein Interactions with Ets-1 and Ets-2 in the Transcriptional Activation of the Human Stromelysin Promoter." J Biol Chem 1999, 274:17342-17352.
Zou et al., "The Oncogenic TLS-ERG Fusion Protein Exerts Different Effects in Hematopeoitic Cells and Fibroblasts." Molecular and Cellular Biology 2005, 25(14): 6235-6246.
Yang et al., "EWS-FLI-1 Fusion Protein Interacts with Hyperphosphorylated RNA Polymerase II and Interferes with Serine-Arginine Protein-mediated RNA Splicing." J Biol. Chem. 2000, 275(48):37612-37618.
Lukkonen et al., "Tumor-associated trypsin inhibitor in normal and malignant renal tissue and in serum of renal-cell carcinoma patients." International J of Cancer 1999, 83(4):486-490.
Solakidi et al., "Co-expression of trypsin and tumour-associated trypsin inhibitor (TATI) in colorectal adenocarcinomas." Histology and Histopathology 2003, 18(4):1181-1188.
Fukayama et al., "immunohistochemical localization of pancreatic secretory trypsin inhibitor in fetal and adult pancreatic and extrapancreatic tissues." J Histochemistry and Cytochemistry. 1986 34(2): 227-235.
Wu et al., "Regulation of the ETS transcription factor ER81 by the 90-kDa ribosomal S6 kinase 1 and protein kinase A." J Biology Chem. 2002, 277(45): 42669-42679.
Brahmajothi et al., "Regional localization of ERG, the channel protein responsible for the rapid component of the delayed rectifier, K+ current in the ferret heart." Circulation Research 1997, 81(1):128-135.
Iftikhar et al., "Disease-and cell-specific expression of GP73 in human liver disease." Am. J Gastrenterology 2004, 99(6):1087-1095.
Harbig et al., "A sequence identification of the genes detected by probesets on the Affymetrix U133 plus 2.0 array." Nucleic Acids Research. Feb. 2005, 33(3): e31.
Whitehead et al., "Variation in tissue-specific gene expression among natural populations." Genome Biology 2005, 6(2): R13.
Hoshikawa et al., "Hypoxia induces different genes in the lungs of rats compared with mice." Physiol. Genomics 2003, 12:209-219.
Affymetrix HG_U95Av2 array showing SPINK1 https://www.affymetrix.com/analysis/netaffx/fullrecord.affx?pk=HG-U95AV2:38582_AT accesses online Jun. 1, 2012.
Affymetrix HG_U95Av2 array showing ERG https://www.affymetrix.com/analysis/netaffx/fullrecord.affx?pk=HG-U95AV2:36383_AT accesses online Jun. 1, 2012.
Ikawa et al., "B-raf, a new member of the raf family, is activated by DNA rearrangement." Mol Cell Biol. Jun. 1988; 8(6):2651-4.
Wan et al., "Mechanism of activation of the RAF-ERK signaling pathway by oncogenic mutations of B-RAF." Cell Mar. 19, 2004; 116(6):855-67.
Olive, "Quantitative methods for the analysis of protein phosphorylation in drug development." Expert Rev Proteomics Oct. 2004; 1(3):327-41.
Bos, "ras Oncogenes in Human Cancer: A Review." Cancer Res 1989; 49:4682-4689.
Kranenburg, "The KRAS oncogene: past, present, and future." Biochim Biophys Acta. Nov. 25, 2005;1756(2):81-2.
Hnatowich et al., "The preparation and labeling of DTPA-coupled albumin." Int J Appl Radiat Isot. May 1982;33 (5):327-32.
Khaw et al., "Myocardial infarct imaging of antibodies to canine cardiac myosin with indium-111-diethylenetriamine pentaacetic acid." Science. Jul. 11, 1980; 209(4453):295-7.
Wong et al., "A rapid chemical method of labeling human plasma proteins with 99mTc-pertechnetate at pH 7.4." Int J Appl Radiat Isot. May 1978;29(4-5):251-3.
Wong et al., "Imaging endocarditis with Tc-99m-labeled antibody—an experimental study: concise communication." J Nucl Med. Mar. 1982;23(3):229-34.
Scheinberg et al., "Tumor imaging with radioactive metal chelates conjugated to monoclonal antibodies." Science. Mar. 19, 1982; 215(4539):1511-3.
Wang et al., "An integrative approach to reveal driver gene fusions from paired-end sequencing data in cancer." Nat Biotechnol. Nov. 2009;27(11):1005-1011.
Cohen et al, "BRAF mutation in papillary thyroid carcinoma." J Natl Cancer Inst. Apr. 16, 2003;95(8):625-7.
Xing, "BRAF mutation in thyroid cancer." Endocr Relat Cancer. Jun. 2005; 12(2):245-62.
Ciampi, "Oncogenic AKAP9-BRAF fusion is a novel mechanism of MAPK pathway activation in thyroid cancer." J Clin Invest. Jan. 2005; 115(1):94-101.
Wang et al., "BRAF mutations in colon cancer are not likely attributable to defective DNA mismatch repair." Cancer Res. Sep. 1, 2003;63(17):5209-12.
Dessars et al., "Chromosomal translocations as a mechanism of BRAF activation in two cases of large congenital melanocytic nevi." J Invest Dermatol. Jun. 2007;127(6):1468-70.

(56) References Cited

OTHER PUBLICATIONS

Wilhelm et al., "Preclinical overview of sorafenib, a multikinase inhibitor that targets both Raf and VEGF and PDGF receptor tyrosine kinase signaling." Mol Cancer Ther. Oct. 2008; 7(10):3129-40.
Sala et al., "BRAF silencing by short hairpin RNA or chemical blockade by PLX4032 leads to different responses in melanoma and thyroid carcinoma cells." Mol Cancer Res. May 2008;6(5):751-9.
Warzecha et al., "ESRP1 and ESRP2 are epithelial cell-type-specific regulators of FGFR2 splicing." Mol Cell. Mar. 13, 2009; 33(5):591-601.
Cho et al., "BRAF and KRAS mutations in prostatic adenocarcinoma." Int J Cancer. Oct. 15, 2006;119(8):1858-62.
MacConaill et al., "Profiling critical cancer gene mutations in clinical tumor samples." PLoS One. Nov. 18, 2009; 4(11):e7887.
Garte et al., "Inhibition of H-ras oncogene transformation of NIH3T3 cells by protease inhibitors." Cancer Res. Jun. 15, 1987;47(12):3159-62.
Hoeflich et al., "In vivo antitumor activity of MEK and phosphatidylinositol 3-kinase inhibitors in basal-like breast cancer models." Clin Cancer Res. Jul. 15, 2009;15(14):4649-64.
Pratilas et al., "(V600E)BRAF is associated with disabled feedback inhibition of RAF-MEK signaling and elevated transcriptional output of the pathway." Proc Natl Acad Sci U S A. Mar. 17, 2009;106(11):4519-24.
Jeong et al., "BRAF activation initiates but does not maintain invasive prostate adenocarcinoma." PLoS One. 2008;3(12):e3949.
Janknecht, "Analysis of the ERK-stimulated ETS transcription factor ER81." Mol Cell Biol. Apr. 1996; 16(4):1550-6.
Varambally et al., "Integrative genomic and proteomic analysis of prostate cancer reveals signatures of metastatic progression." Cancer Cell Nov. 2005, 8:393-406.
*Homo sapiens* angiotensin II receptor-associated protein (AGTRAP), transcript variant 2, mRNA, NCBI Reference Sequence: NM_001040194.1, 4 pages.
*Homo sapiens* angiotensin II receptor-associated protein (AGTRAP), transcript variant 4, Mrna, NCBI Reference Sequence: NM_001040196.1, 4 pages.
*Homo sapiens* angiotensin II receptor-associated protein (AGTRAP), transcript variant 5, mRNA, NCBI Reference Sequence: NM_001040197.1, 4 pages.
Walker G. et al, , "Isothermal in vitro amplification of DNA by a restriction enzyme/DNA polymerase system," Proc Natl Acad Sci USA 1992, 89: 392-396.
Lizardi et al, "Exponential Amplification of Recombinant-RNA Hybridization Probes," Biotechnol 6: 1197-1202 (1988).
Kwoh et al, "Transcription-based amplification system and detection of amplified human immunodeficiency virus type 1 with a bead-based sandwich hybridization format," Proc Natl Acad Sci USA 1989, 86: 1173-1177.
Guatelli et al, "Isothermal, in vitro amplification of nucleic acids by a multienzyme reaction modeled after retroviral replication," Proc Natl Acad Sci USA (1990), 87: 1874-1878.
Nelson, Norman C., et al., "Detection of Acridinium Esters by Chemiluminescence" Nonisotopic Probing, Blotting, and Sequencing, 2nd Edition, edited by Larry J. Kricka, (1995) Ch. 17, pp. 391-428.
Sumerdon et al, "An Optimized Antibody-Chelator Conjugate for Imaging of Carcinoembryonic Antigen with Indium-111," Nucl Med Biol 17: 247-254 (1990).
Griffin et al, (1991), "Initial clinical study of indium-111-labeled clone 110 anticarcinoembryonic antigen antibody in patients with colorectal cancer," J Clin Oncol, 9: 631-640.
Lauffer, (1991), "Targeted relaxation enhancement agents for MRI," Magnetic Resonance in Medicine 22: 339-342 (1991).
Zervos et al, "Mxi1, a protein that specifically interacts with Max to bind Myc-Max recognition sites," Cell 72: 223-232 (1993).
Madura et al,, "N-recognin/Ubc2 interactions in the N-end rule pathway," J Biol Chem 2668. 12046-12054 (1993).

Bartel et al, "Elimination of false positives that arise in using the two-hybrid system," Biotechniques 14: 920-924 (1993).
Iwabuchi et al, "Use of the two-hybrid system to identify the domain of p53 involved in oligomerization," Oncogene 8: 1693-1696 (1993).
Karnoub et al, "Ras oncogenes: split personalities," Nat Rev Mol Cell Biol, 9, 517-531 ( 2008).
Rodriguez-Viciana et al, "Cancer targets in the Ras pathway," Cold Spring Harb Symp Quant Biol 70, 461-467 (2005).
Moul et al, "Infrequent RAS oncogene mutations in human prostate cancer," Prostate 20, 327-338 (1992).
Seeburg et al, "Biological properties of human c-Ha-rasl genes mutated at codon 12," Nature 312, 71-75 (1984).
Schubbert et al., "Hyperactive Ras in developmental disorders and cancer," Nat Rev Cancer 7, 295-308, (2007).
Mullighan et al, "BCR-ABL1 lymphoblastic leukaemia is characterized by the deletion of Ikaros," Nature 453, 110-114 (2008).
Graux et al, " Fusion of NUP214 to ABL1 on amplified episomes in T-cell acute lymphoblastic leukemia," Nat Genet 36, 1084-1089 (2004).
Ferreira et al, "Array CGH and gene-expression profiling reveals distinct genomic instability patterns associated with DNA repair and cell-cycle checkpoint pathways in Ewing's sarcoma," Oncogene 27, 2084-2090 (2008).
Koivunen et al, "EML4-ALK fusion gene and efficacy of an ALK kinase inhibitor in lung cancer," Clin Cancer Res 14, 4275-4283 (2008).
Stergianou et al, "Fusion of NUP214 to ABL1 on amplified episomes in T-ALL—implications for treatment," Leukemia 19, 1680-1681 (2005).
Graff et al, "Increased AKT activity contributes to prostate cancer progression by dramatically accelerating prostate tumor growth and diminishing p27Kip1 expression," J. Biol Chem 275, 24500-24505 (2000).
Xu et al, "MAPKAPK2 and HSP27 are downstream effectors of p38 MAP kinase-mediated matrix metalloproteinase type 2 activation and cell invasion in human prostate cancer," Oncogene 25, 2987-2998 (2006).
Li et al, "A neoplastic gene fusion mimics trans-splicing of RNAs in normal human cells," Science 321, 1357-1361 (2008).
Der et al, "Transforming genes of human bladder and lung carcinoma cell lines are homologous to the ras genes of Harvey and Kirsten sarcoma viruses," Proc Natl Acad Sci USA 79, 3637-3640 (1982).
Zhu et al, "Transformation potential of Ras isoforms correlates with activation of phosphatidylinositol 3-kinase but not ERK," J Biol Chem 279, 37398-37406 (2004).
Moynihan et al, "Fine-mapping, genomic organization, and transcript analysis of the human ubiquitin-conjugating enzyme gene UBE2L3," Genomics 51, 124-127 (1998).
Hoeller et al., "Targeting the ubiquitin system in cancer therapy," Nature 458, 438-444 (2009).
Barr et al. 1996, "In Vivo Amplification of the PAX3-Fkhr and PAX7-Fkhr Fusion Genes in Alveolar Rhabdomyosarcoma" Hum. Mol. Genet., 5; 15-21.
Ciampi, R. et al., "BRAF kinase activation via chromosomal rearrangment in radiation-induced and sporadic thyroid cancer." Cell Cycle 2005 4(4): 547-548.
Jones, D.T. et al., "Tandem duplication producing a novel oncogenic BRAF fusion gene defines the majority of pilocytic astrocytomas." Cancer Research 2008 68(21):8673-8677.
Esgueva, R. et al., "Prevalence of TMPRSS2-ERG and SLC45A3-ERG gene fusions in a large prostatectomy cohort." Modern Pathology 2010 23(4):539-546.
Palanisamy, N. "Rearrangments of the RAF kinase pathway in prostate cancer, gastric cancer and melanoma." Nature Medicine 2010 16(7):793-798.
Fradet et al., "APTIMA® PCA3 Molecular Urine Test: Development of Prostate Cancer" European Urology Supplements 2006, 5(2): 275.
Kong et al. "Consistent Detection of TLS/FUS-ERG Chimeric Transcripts in Acute Myeloid Leukemia With t(16;21) (p11;q22) and Identification of a Novel Transcript" Blood 1997, 90:1192.

(56) References Cited

OTHER PUBLICATIONS

International Search Report Mailed May 20, 2011 Application No. PCT/US2010/048915; 13 Pages.
US Final Office Action Mailed Jun. 22, 2011, U.S. Appl. No. 12/272,865.
Australian Office Action Mailed Jun. 27, 2011 Application No. 2008275304, 2 Pages.
US Final Office Action Mailed Aug. 23, 2011, U.S. Appl No. 11/825,552, 42 Pages.
European Office Action Issued Jun. 28, 2011, Application No. 08772418.3, 4 Pages.
European Office Action Issued Jun. 27, 2011, Application No. 07864115.6, 6 Pages.
EP Search Report Dated Jul. 8, 2011; Application No. 06814528.3.
Li J. et al., "PTEN, A Putative Protein Tyrosene Phosphatase Gene Mutated in Human Brain, Breast, and Prostate Cancer." Science, American Association for the Advancement of Science 1997, 275:1943-1947.
Jarrard D.F. et al., "Deltional, Mutational, and Methylation Analyses of CDKN2 (P16/MTS1) in Primary and Metastatic Prostate Cancer." Genes, Chromosomes & Cancer 1997, 19(2):90-96.
Asatiani E. et al., "Deletion, methylation, and expression of the NKX3.1 suppressor gene in primary human prostate cancer." Cancer Research 2005, 65(4):1164-1173.
Jeon In-Sang et al., "A variant Ewing's sarcoma translocation (7;22) fuses the EWS gene to the ETS gene ETV1." Oncogene 1995, 10(6):1229-1234.
Oikawa T. et al., "Molecular biology of the ETS family of transcription factors." Gene 2003, 303(16):11-34.
Sorenson Poul H B et al., "A Second Ewing's sarcoma translocation, t(21; 22), fuses the EWS gene to anther ETS-family transcription factor, ERG." Nature Genetics 1994, 6(2):146-151.
AU Office Action dated Jul. 5, 2011; Application No. 2009316693; 3 pages.
*Homo sapiens* angiotensin II receptor-associated protein (AGTRAP), transcript variant 3, Mrna, NCBI Reference Sequence: NM_001040195.1.
"*Homo sapiens* epithelial splicing regulatory protein 1 (ESRP1), transcript variant 1, mRNA NCBI Reference Sequence: NM_017697.3".
*Homo sapiens* v-raf murine sarcoma viral oncogene homolog B1 (BRAF), RefSeqGene on chromosome 7, NCBI Reference Sequence: NG_007873.2.
*Homo sapiens* v-raf murine sarcoma viral oncogene homolog B (BRAF), Mrna NCBI Reference Sequence: NM_004333.4.
*Homo sapiens* v-raf-1 murine leukemia viral oncogene homolog 1 (RAF1), RefSeqGene (LRG_413) on chromosome 3 NCBI Reference Sequence: NG_007467.1.
*Homo sapiens* v-raf-1 murine leukemia viral oncogene homolog 1 (RAF1), mRNA NCBI Reference Sequence: NM_002880.3.
Cruz et al., "Absence of BRAF and NRAS Mutations in Uveal Melanoma." Cancer Research Oct. 1, 2003, 63:5761-5766.
Benner et al., "Evolution, language and analogy in functional genomics." Trends in Genetics Jul. 2001, 17(7): 414-418.
Lynch et al., "Activating mutations in the epidermal growth factor receptor underlying responsiveness of non-small-cell lung cancer to gefitinib." N Engl J Med. May 20, 2004;350(21):2129-39.
Slamon et al., "Use of chemotherapy plus a monoclonal antibody against HER2 for metastatic breast cancer that overexpresses HER2." N Engl J Med. Mar. 15, 2001;344(11):783-92.
Demetri et al., "Efficacy and safety of imatinib mesylate in advanced gastrointestinal stromal tumors." N Engl J Med. Aug. 15, 2002;347(7):472-80.
Druker et al., "Five-year follow-up of patients receiving imatinib for chronic myeloid leukemia." N Engl J Med. Dec. 7, 2006;355(23):2408-17.
Greenman et al., "Patterns of somatic mutation in human cancer genomes." Nature. Mar. 8, 2007;446(7132):153-8.
Weir et al., "Characterizing the cancer genome in lung adenocarcinoma." Nature. Dec. 6, 2007;450(7171):893-8.
Barber et al., "Somatic mutations of EGFR in colorectal cancers and glioblastomas." N Engl J Med. Dec. 30, 2004;351(27):2883.
Futreal et al., "A census of human cancer genes." Nat Rev Cancer. Mar. 2004;4(3):177-83.
Choi et al., "Identification of novel isoforms of the EML4-ALK transforming gene in non-small cell lung cancer." Cancer Res. Jul. 1, 2008;68(13):4971-6.
Perner et al., "EML4-ALK fusion lung cancer: a rare acquired event." Neoplasia. Mar. 2008; 10(3):298-302.
Rikova et al., "Global survey of phosphotyrosine signaling identifies oncogenic kinases in lung cancer." Cell. Dec. 14, 2007;131(6):1190-203.
Campbell et al., "Identification of somatically acquired rearrangements in cancer using genome-wide massively parallel paired-end sequencing." Nat Genet. Jun. 2008;40(6):722-9.
Parsons et al., "An integrated genomic analysis of human glioblastoma multiforme." Science. Sep. 26, 2008;321(5897):1807-12.
Lin et al., "Prostate-localized and androgen-regulated expression of the membrane-bound serine protease TMPRSS2." Cancer Res. Sep. 1, 1999;59(17):4180-4.
GenBank: AAC51784.1, serine protease [*Homo sapiens*].
GenBank: U75329.1, Human serine protease mRNA, complete cds.
Ota et al., "Complete sequencing and characterization of 21,243 full-length human cDNAs." Nat Genet. Jan. 2004;36 (1):40-5.
Genbank Accession NM_014685.3, *Homo sapiens* homocysteine-inducible, endoplasmic reticulum stress-inducible, ubiquitin-like domain member 1 (HERPUD1), transcript variant 1, Mrna.
Genbank Accession NM_004449.4, *Homo sapiens* v-ets erythroblastosis virus E26 oncogene homolog (avian) (ERG), transcript variant 2, mRNA.
Genbank Accession M17254.1, Human erg2 gene encoding erg2 protein, complete cds.
Swiss Protein Acc. No. P11308.2, RecName: Full=Transcriptional regulator ERG; AltName: Full=Transforming protein ERG.
Genbank Accession No. NC_00007.11, *Homo sapiens* chromosome 7, complete sequence.
Genbank Accession No. NT_007819.15, *Homo sapiens* chromosome 7 genomic contig.
Genbank Accession No. NM_004956.4, *Homo sapiens* ets variant 1 (ETV1), transcript variant 1, mRNA.
Genbank Accession No. NP_004947.2, ETS translocation variant 1 isoform a [*Homo sapiens*].
Genbank Accession No. NC_000017.9, *Homo sapiens* chromosome 17, reference assembly, complete sequence.
Genbank Accession No. NT_010783.14, *Homo sapiens* chromosome 17 genomic contig, reference assembly.
Genbank Accession No. NM_001986.2, *Homo sapiens* ets variant 4 (ETV4), transcript variant 1, mRNA.
UniProtKB/Swiss-Prot: P43268.3, RecName: Full=ETS translocation variant 4; AltName: Full=Adenovirus E1A enhancer-binding protein; AltName: Full=E1A-F; AltName: Full=Polyomavirus enhancer activator 3 homolog; Short=Protein PEA3.
NC_000003.10, *Homo sapiens* chromosome 3, reference assembly, complete sequence, 1 page.
NM_004454.2, *Homo sapiens* ets variant 5 (ETV5), Mrna, 5 pages.
McConnell et al., "The cytosensor microphysiometer: biological applications of silicon technology." Science. Sep. 25, 1992;257(5078):1906-12.
Klinger et al., "Rapid detection of chromosome aneuploidies in uncultured amniocytes by using fluorescence in situ hybridization (FISH)." Am J Hum Genet. Jul. 1992;51(1):55-65.
Rubin et al.,Rapid ("warm") autopsy study for procurement of metastatic prostate cancer. Clin Cancer Res. Mar. 2000;6(3):1038-45.
Karolchik et al., "The UCSC Table Browser data retrieval tool." Nucleic Acids Res. Jan. 1, 2004;32(Database Issue):D493-6.
GenBank: DQ204772.1, *Homo sapiens* TMPRSS2/ERGa fusion transcript.
M30829.1, Human bcr/abl fusion protein mRNA, partial cds, clone K28.

(56) References Cited

OTHER PUBLICATIONS

Communi et al., "Cotranscription and intergenic splicing of human P2Y11 and SSF1 genes." J Biol Chem. May 11, 2001;276(19):16561-6.
Shtivelman et al., "Fused transcript of abl and bcr genes in chronic myelogenous leukaemia." Nature. Jun. 13-19, 1985;315(6020):550-4.
Kato et al., "Activation of Holliday junction-recognizing protein involved in the chromosomal stability and immortality of cancer cells." Cancer Res. Sep. 15, 2007;67(18):8544-53.
Bashir et al., "Evaluation of paired-end sequencing strategies for detection of genome rearrangements in cancer." PLoS Comput Biol. Apr. 25, 2008;4(4):e1000051.
Yu et al., "Integrative genomics analysis reveals silencing of beta-adrenergic signaling by polycomb in prostate cancer." Cancer Cell. Nov. 2007;12(5):419-31.
Afar, et al., "Catalytic cleavage of the Androgen-regulated TMPRSS2 Protease Results in Its Secretion by Prostate and Prostate Cancer Epithelia," Cancer Research, 2001, pp. 1686-1692 vol. 61.
Ahlers and Figg. "ETS-TPRSS2 Fusion Gene Products in Prostate Cancer." Cancer Biology & Therapy, (2006) 5:3 pp. 254-255.
Cerveira, et al. "TMPRSS2-ERG Gene Fusion Causing ERG Overexpression Precedes Chromosome Copy Number Changes in Prostate Carcinomas and Paired HGPIN Lesions." Neoplasia, (2006) pp. 826-832 vol. 8 (10).
Demichelis, et al. "TMPRSS2: ERG gene fusion associated with lethal prostate cancer in a watchful waiting cohort." Oncogene, (2007) 26(31):4596-4599.
Hendriksen, et al. "Evolution of the Androgen Receptor Pathway during Progression of Prostate Cancer." Cancer Research, (2006) 66(10):5012-5020.
Hermans, et al. "TMPRSS2:ERG Fusion by Translocation or Interstitial Deletion is Highly Relevant in Androgen-Dependent Prostate Cancer, But is Bypassed in Late-Stage Androgen Receptor-Negative Prostate Cancer." Cancer D Research (2006) pp. 10658-10663, vol. 66:22.
Jacquinet, et al. "Cloning and characterization of the cDNA and gene for human epitheliasin." European Journal of Biochemistry (2001) pp. 2687-2699, vol. 268.
Laxman, Bharathi, et al., "Noninvasive Detection of TMPRSS2:ERG Fusion Transcripts in the Urine of Men with Prostate Cancer," Neoplasia, 2006, pp. 885-888 vol. 8(10).
Mehra, et al. "Comprehensive assessment of TMPRSS2 and ETS family gene aberrations in clinically localized prostate cancer." Modern Pathology, (2007) vol. 20(5):538-544.
Mosquera, et al. "Morphological Features of TMPRSS2-ERG gene fusion prostate cancer." Journal of Pathology, (2007) pp. 91-101, vol. 212.
Oettgen, et al. "PDEF, a Novel Prostate Epithelium-specific Ets Transcription Factor, Interacts with the Androgen Receptor and Activates Prostate-specific Antigen Gene Expression." Journal of Biological Chemistry, (2000) pp. 1216-1225, vol. 275:2.
Owczarek et al. "Detailed mapping of the ERG-ETS2 interval of human chromosome 21 and comparison with the region of conserved synteny on mouse chromosome 16." Gene, (2004) pp. 65-77, vol. 324.
Perner, et al. "TMPRSS2:ERG Fusion-Associated Deletions Provide Insight into the Heterogeneity of Prostate Cancer." Cancer Res, (2006) pp. 8337-8341, vol. 66:17.
Petrovics et al. "Frequent overexpression of ETS-related gene-1 (ERG1) in prostate cancer transcriptome." Oncogene (2005) pp. 3847-3852, vol. 24.
Reddy, et al. "The erg gene: A human gene related to the ets oncogene." Proc. Natl. Acad. Sci. (1987) pp. 6131-6135, vol. 84, USA.
Rubin and Chinnaiyan. "Bioinformatics approach leads to the discovery of the TMPRSS2:ETS gene fusion in prostate cancer." Laboratory Investigation (2006) pp. 1099-11 02, vol. 86.
Vaarala, et al. "The TMPRSS2 Gene Encoding Transmembrane Serine Protease Is Overexpressed in a Majority of Prostate Cancer Patients: Detection of Mutated TMPRSS2 Form in a Case of Aggressive Disease." International Journal of Cancer, (2001) pp. 705-710, vol. 94.
Rao, et al. "erg, a Human ets-Related Gene on Chromosome 21: Alternative Splicing, Polyadenylation, and Translation." Science (1987), 237(4815):635-639.
Wang, et al. "Expression of Variant TMPRSS2/ERG Fusion Messenger RNAs is Associated with Aggressive Prostate Cancer," Cancer Res. (2006) pp. 8347-8351, vol. 66: 17.
Bittner et al, "Molecular classification of cutaneous malignant melanoma by gene expression profiling," Nature, vol. 406, Apr. 2000, pp. 536-540.
Chen, et al., "Variation in gene expression patterns in human gastric cancers", PNAS, vol. 14, Aug. 2003, pp. 3208-3215.
Cheok, et al., Treatment-specific changes in gene expression discriminate in vivo drug response in human leukemia cells, Nature Genetics, vol. 34, May 2003, pp. 85-90, 231.
Deininger, The development of imatinib as a therapeutic agent for chronic myeloid leukemia, Blood, vol. 105, No. 7, Apr. 1, 2005, pp. 2640-2653.
de Klein, "A cellular oncogene is translocated to the Philadelphia chromosome in chronic myelocytic leukaemia", Nature, vol. 300, Dec. 1982, pp. 765-767.
Dhanasekaran, et al., "Molecular profiling of human prostate tissues: insights into gene expression patterns of prostate development during puberty", The FASEB Journal, vol. 19, No. 2, Feb. 2005, pp. 243-245.
Eisen, et al., "Cluster analysis and display of genome-wide expression patterns", PNAS, vol. 95, No. 25, Dec. 8, 1998, pp. 14863-14868.
Ferrando, et al., "Gene expression signatures define novel oncogenic pathways in T cell acute lymphoblastic leukemia", Cancer Cell, vol. 1, Feb. 2002, pp. 75-87.
Fonseca, et al., "Genetics and Cytogenetics of Multiple Myeloma: A Workshop Report", Cancer Research, vol. 64, Feb. 15, 2004, pp. 1546-1558.
Garraway, et al., "Integrative genomic analyses identify MITF as a lineage survival oncogene amplified in malignant melanoma", Nature, vol. 436, Jul. 7, 2005, pp. 117-122.
Golub, et al., "Molecular classification of cancer: class discovery and class prediction by gene expression monitoring", Science, vol. 286, Oct. 15, 1999, pp. 531-537.
Huang, et al., "Gene expression predictors of breast cancer outcomes", The Lancet, vol. 361, May 10, 2003, pp. 1590-1596.
Jain, et al., "Expression profiles provide insights into early malignant potential and skeletal abnormalities in multiple endocrine neoplasia type 2B syndrome tumors", Cancer Research 64, Jun. 1, 2004, pp. 3907-3913.
Keats, et al., "Overexpression of transcripts originating from the MMSET locus characterizies all t(4:14)(p16;q32)-positive multiple myeloma patients", Blood, vol. 105, No. 10, May 15, 2005, pp. 4060-4069.
Lapointe, et al., "Gene expression profiling identifies clinically relevant subtypes of prostate cancer", PNAS, Jan. 20, 2004, vol. 101, No. 3, pp. 811-816.
Latulippe, et al., "Comprehensive gene expression analysts of prostate cancer reveals distinct transcriptional programs associated with metastatic disease", Cancer Research 62, Aug. 1, 2002, pp. 4499-4506.
Lin, et al., "Prostate-localized and Androgen-regulated Expression of the Membrane-bound Serine Protease TMPRSS2", Cancer Research 59, Sep. 1, 1999, pp. 4180-4184.
Mitelman, F., "Recurrent chromosome aberrations in cancer", Mutation Research 462 (2000), pp. 247-253.
Paoloni-Giacobino, et al., "Cloning of the TMPRSS2 gene, which encodes a novel serine protease with transmembrane, LDLRA, and SRCR domains and maps to 21q22.3", Genomics, vol. 44, No. 3, Sep. 15, 1997, pp. 309-320.
Paris, et al., "Whole genome scanning identifies genotypes associated with recurrence and metastasis in prostate tumors", Human Molecular Genetics, 2004, vol. 13, No. 13, pp. 1303-1313.
Rabbitts, T.H., "Chromosomal translocations in human cancer", Nature, vol. 372, Nov. 10, 1994, pp. 143-149.

(56) References Cited

OTHER PUBLICATIONS

Rhodes, et al., "ONCOMINE: A cancer microarray database and integrated data-mining platform", Neoplasia, vol. 6, No. 1, Jan./Feb. 2004, pp. 1-6.

Rosenwald et al. "The proliferation gene expression signature is a quantitative integrator of oncogenic events that predicts survival in mantle cell lymphoma," Cancer Cell., vol. 3, Feb. 2003, pp. 185-197.

Rowley, "A new Consistent Chromosomal Abnormality in Chronic Myelogenous Leukaemia Identified by Quinacrine Fluorescence and Giemsa Staining", Nature, vol. 243, Jun. 1, 1973, pp. 290-293.

Rowley, J.D., "Chromosome translocations: dangerous liaisons revisted", Nature Reviews, Cancer; vol. 1, Dec. 2001, pp. 245-250.

Rubin, et al., "Overexpression, amplification, and androgen regulation of TPD52 in prostate cancer", Cancer Research 64, Jun. 1, 2004, pp. 3814-3822.

Schwartz, et al., "Gene expression in ovarian cancer reflects both morphology and biological behavior, distinguishing clear cell from other poor-prognosis ovarian carcinomas", Cancer Research 62, Aug. 15, 2002, pp. 4722-4729.

Slamon, et al., "Human breast cancer: correlation of relapse and survival with amplification of the HER-2/neu oncogene", Science, vol. 235, No. 4785, Jan. 9, 1987, pp. 177-182.

Soller et al., "Confirmation of the High Frequency of the TMPRSS2/ERG Fusion Gene in Prostate Cancer", Genes, Chromosomes & Cancer, vol. 45 (2006), pp. 717-719.

Sotiriou, et al., "Breast cancer classification and prognosis based on gene expression profiles from a population-based study", PNAS, vol. 100, No. 18, Sep. 2, 2003, pp. 10393-10398.

Tian, et al., The role of the Wnt-signaling antagonist DKK1 in the development of osteolytic lesions in multiple myeloma, The New England Journal of Medicine, vol. 349, No. 26, Dec. 25, 2003, pp. 2483-2494.

Ichikawa et al., "Dual transforming activities of the FUS (TLS)-ERG leukemia fusion protein conferred by two N-terminal domains of FUS (TLS)." Mol Cell Biol. Nov. 1999;19(11):7639-50.

Iljin, et al. "TMPRSS2 fusions with oncogenic ETS factors in prostate cancer involve unbalanced genomic rearrangements and are associated with HDAC1 and epigenetic reprogramming." Cancer Res. Nov. 1, 2006; 66(21)10242-6.

He Jintang et al., "Antibody-independent targeted quantification of TMPRSS2-ERG fusion protein products in prostate cancer." Mol Oncol. Oct. 2014;8(7):1169-80.

Tackels-Horne et al., "Identification of differentially expressed genes in hepatocellular carcinoma and metastatic liver tumors by oligonucleotide expression profiling." Cancer. Jul. 15, 2001;92(2):395-405.

\* cited by examiner a b c d a b

US 9,567,644 B2

RAF GENE FUSIONS

This application is a divisional of U.S. patent application Ser. No. 13/300,063, filed Nov. 18, 2011, which claims priority to U.S. provisional patent application 61/415,495, filed Nov. 19, 2010, each of which is herein incorporated by reference in its entirety.

GOVERNMENT SUPPORT

This invention was made with government support under CA132874, CA069568, CA111275 and DA021519 awarded by the National Institutes of Health and W81XWH-09-2-0013 awarded by the Army/MRMC. The government has certain rights in the invention.

FIELD OF THE INVENTION

The present disclosure relates to compositions and methods for cancer diagnosis, research and therapy, including but not limited to, cancer markers. In particular, the present disclosure relates to RAF gene fusions as diagnostic markers and clinical targets for cancer.

BACKGROUND OF THE INVENTION

A central aim in cancer research is to identify altered genes that are causally implicated in oncogenesis. Several types of somatic mutations have been identified including base substitutions, insertions, deletions, translocations, and chromosomal gains and losses, all of which result in altered activity of an oncogene or tumor suppressor gene. First hypothesized in the early 1900's, there is now compelling evidence for a causal role for chromosomal rearrangements in cancer (Rowley, *Nat Rev Cancer* 1: 245 (2001)). Recurrent chromosomal aberrations were thought to be primarily characteristic of leukemias, lymphomas, and sarcomas. Epithelial tumors (carcinomas), which are much more common and contribute to a relatively large fraction of the morbidity and mortality associated with human cancer, comprise less than 1% of the known, disease-specific chromosomal rearrangements (Mitelman, *Mutat Res* 462: 247 (2000)). While hematological malignancies are often characterized by balanced, disease-specific chromosomal rearrangements, most solid tumors have a plethora of non-specific chromosomal aberrations. It is thought that the karyotypic complexity of solid tumors is due to secondary alterations acquired through cancer evolution or progression.

Two primary mechanisms of chromosomal rearrangements have been described. In one mechanism, promoter/enhancer elements of one gene are rearranged adjacent to a proto-oncogene, thus causing altered expression of an oncogenic protein. This type of translocation is exemplified by the apposition of immunoglobulin (IG) and T-cell receptor (TCR) genes to MYC leading to activation of this oncogene in B- and T-cell malignancies, respectively (Rabbitts, *Nature* 372: 143 (1994)). In the second mechanism, rearrangement results in the fusion of two genes, which produces a fusion protein that may have a new function or altered activity. The prototypic example of this translocation is the BCR-ABL gene fusion in chronic myelogenous leukemia (CML) (Rowley, *Nature* 243: 290 (1973); de Klein et al., *Nature* 300: 765 (1982)). Importantly, this finding led to the rational development of imatinib mesylate (Gleevec), which successfully targets the BCR-ABL kinase (Deininger et al., *Blood* 105: 2640 (2005)). Thus, identifying recurrent gene rearrangements in common epithelial tumors may have profound implications for cancer drug discovery efforts as well as patient treatment.

SUMMARY OF THE INVENTION

The present disclosure relates to compositions and methods for cancer diagnosis, screening, research and therapy, including but not limited to, cancer markers. In particular, the present disclosure relates to RAF gene fusions as diagnostic markers and clinical targets for cancer.

Embodiments of the present disclosure provide a method for identifying a neoplastic cell (e.g., gastric cancer or melanoma) in a patient comprising: exposing a patient sample comprising a cell, or a secretion thereof to a detection reagent; and detecting the presence or absence in the sample of a gene fusion having a 5' portion from a transcriptional regulatory region of, for example, an SLC45A3, RAF family member, AGTRAP or ESRP1 gene and a 3' portion from a RAF family member gene or an ESRP1 gene, wherein detecting the presence in the sample of the gene fusion identifies cancer (e.g., gastric cancer or melanoma) in the patient. In some embodiments, the transcriptional regulatory region of the SLC45A3, RAF family member, AGTRAP or ESRP1 gene comprises a promoter region of the gene. In some embodiments, the detecting comprises detecting chromosomal rearrangements of genomic DNA having a 5' DNA portion from the transcriptional regulatory region of the SLC45A3, RAF family member, AGTRAP or ESRP1 gene and a 3' DNA portion from the RAF family member gene or the ESPR1 gene. In other embodiments, the detecting comprises detecting chimeric mRNA transcripts having a 5' RNA portion transcribed from the transcriptional regulatory region of the SLC45A3, RAF family member, AGTRAP or ESRP1 gene and a 3' RNA portion transcribed from a RAF family member gene or an ESRP1 gene. In some embodiments, the sample is, for example, tissue, blood, plasma, serum, urine, urine supernatant, urine cell pellet or cells (e.g., gastric or skin cells or a fecal sample). In some embodiments, the RAF family member gene is BRAF or RAF1. In some embodiments, the method further comprises the step of detecting the level of expression of the gene fusion in the sample, wherein detecting an enhanced level of expression of the gene fusion in the patient sample relative to the level of expression of the gene fusion in a normal sample (e.g., relative to the level in normal cells, increase or decrease in level relative to a prior time point, increase or decrease relative to a pre-established threshold level, etc.) indicates the presence of a neoplastic prostate cell or a cell predisposed to the onset of a neoplastic state in the sample.

Further embodiments provide the step of determining a treatment course of action based on the presence or absence of the gene fusion. For example, in some embodiments, the treatment course of action comprises administration of a RAF pathway inhibitor (e.g., BAY43-9006, PLX4720, AZ 628, GCD 0879 or PLX4032) when the gene fusion is present in the sample.

Additional embodiments of the present disclosure provide compositions, kits or systems comprising at least one of the following: (a) an oligonucleotide probe comprising a sequence that hybridizes to a junction of a chimeric genomic DNA or chimeric mRNA in which a 5' portion of the chimeric genomic DNA or chimeric mRNA is from a transcriptional regulatory region of an AGTRAP gene and a 3' portion of the chimeric genomic DNA or chimeric mRNA is from a RAF family member gene; (b) a first oligonucleotide probe comprising a sequence that hybridizes to a 5' portion of a chimeric genomic DNA or chimeric mRNA from a transcriptional regulatory region of an AGTRAP gene and a second oligonucleotide probe comprising a sequence that hybridizes to a 3' portion of the chimeric genomic DNA or chimeric mRNA from a RAF family member gene; (c) a first amplification oligonucleotide comprising a sequence that hybridizes to a 5' portion of a chimeric genomic DNA or chimeric mRNA from a transcriptional regulatory region of an AGTRAP gene and a second amplification oligonucleotide comprising a sequence that hybridizes to a 3' portion of the chimeric genomic DNA or chimeric mRNA from a RAF family member gene; (d) an oligonucleotide probe comprising a sequence that hybridizes to a junction of a chimeric genomic DNA or chimeric mRNA in which a 5' portion of the chimeric genomic DNA or chimeric mRNA is from a transcriptional regulatory region of a RAF family member gene and a 3' portion of the chimeric genomic DNA or chimeric mRNA is from an ESRP1 member gene; (e) a first oligonucleotide probe comprising a sequence that hybridizes to a 5' portion of a chimeric genomic DNA or chimeric mRNA from a transcriptional regulatory region of a RAF family member gene and a second oligonucleotide probe comprising a sequence that hybridizes to a 3' portion of the chimeric genomic DNA or chimeric mRNA from an ESRP1 gene; or (f) a first amplification oligonucleotide comprising a sequence that hybridizes to a 5' portion of a chimeric genomic DNA or chimeric mRNA from a transcriptional regulatory region of a RAF family member gene and a second amplification oligonucleotide comprising a sequence that hybridizes to a 3' portion of the chimeric genomic DNA or chimeric mRNA from an ESRP1 gene. In some embodiments, the RAF family member gene is BRAF or RAF1.

Additional embodiments of the present disclosure are provided in the description and examples below.

DEFINITIONS

Figure 1:
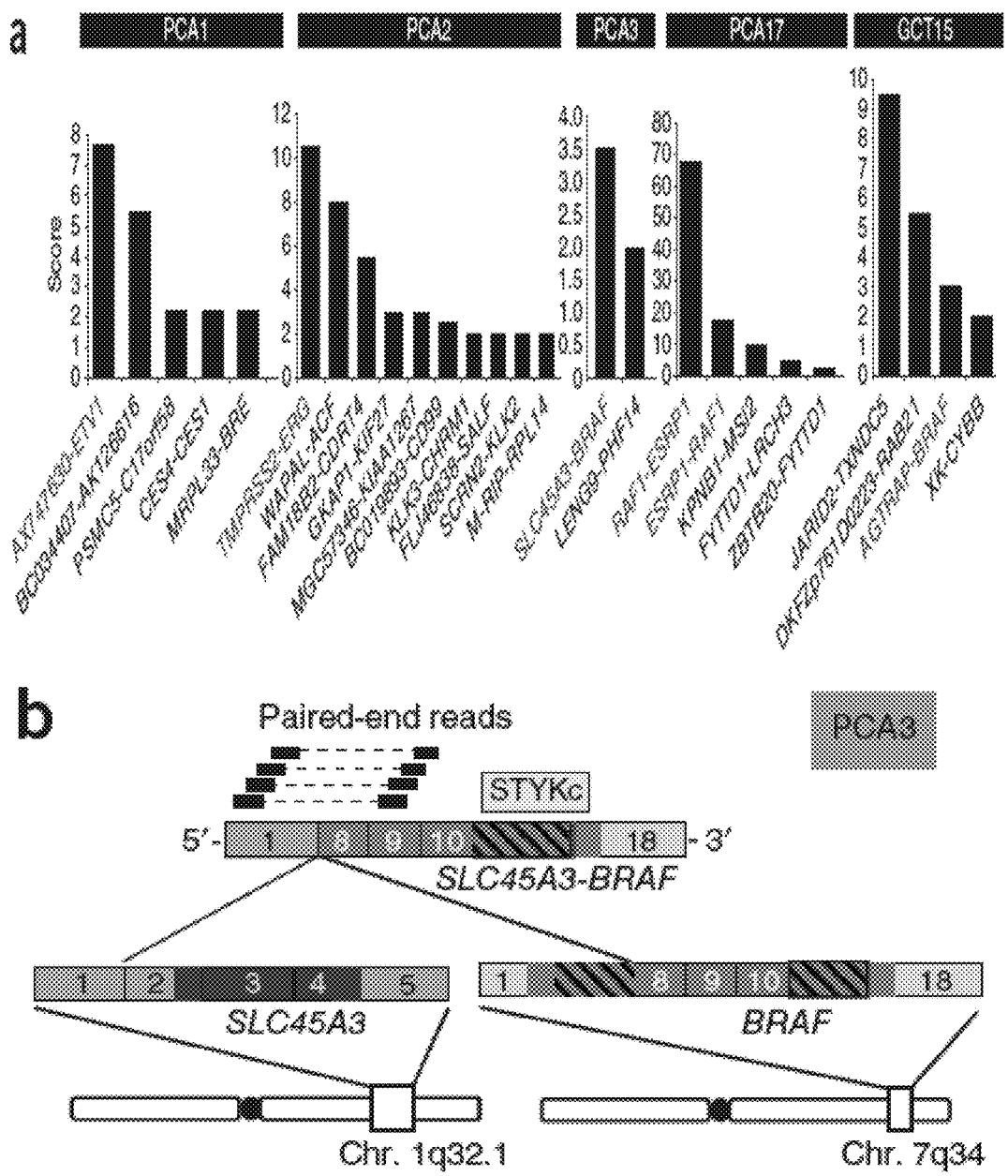
FIG. 1 shows the identification of the SLC45A3-BRAF and ESRP1-RAF1 gene fusions in prostate cancer by paired-end transcriptome sequencing. (a) Histograms of gene fusion nomination scores in clinically localized prostate tumor samples PCA1, PCA2, PCA3 and PCA17 harboring AX747630-ETV1, TMPRSS2-ERG, SLC45A3-BRAF, ESRP1-RAF1 and RAF1-ESR1, respectively, and a gastric cancer sample, GCT15, harboring AGTRAP-BRAF. (b) Schematic representation of reliable paired-end reads supporting the interchromosomal gene fusion between SLC45A3 and BRAF. (c,d) As in b, except showing the fusions between ESRP1 and RAF1, resulting in reciprocal fusion genes ESRP1-RAF1 and RAF1-ESRP1. (e) As in b, except showing the fusion between AGTRAP and BRAF.
Figure 1:
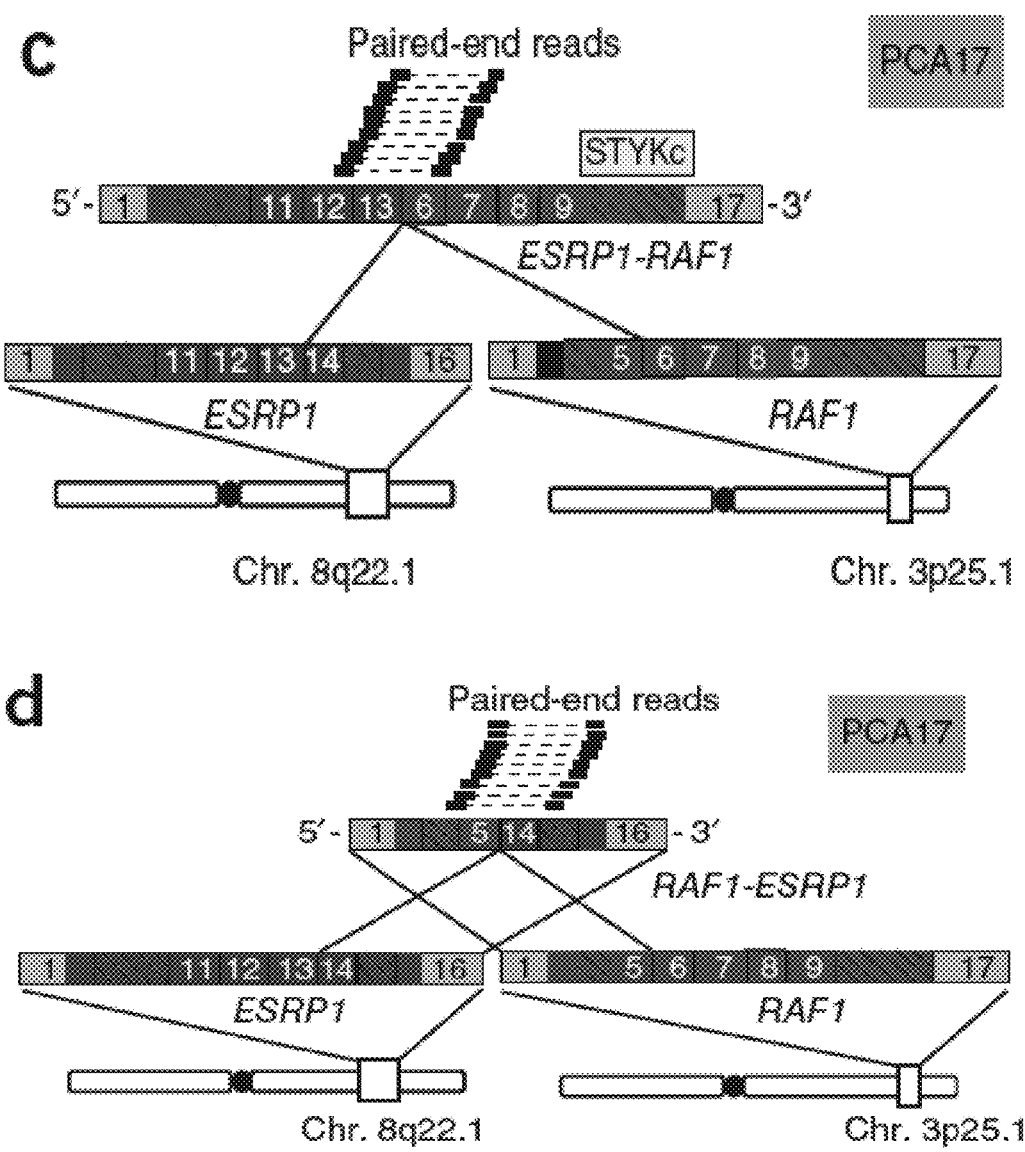
Figure 1:
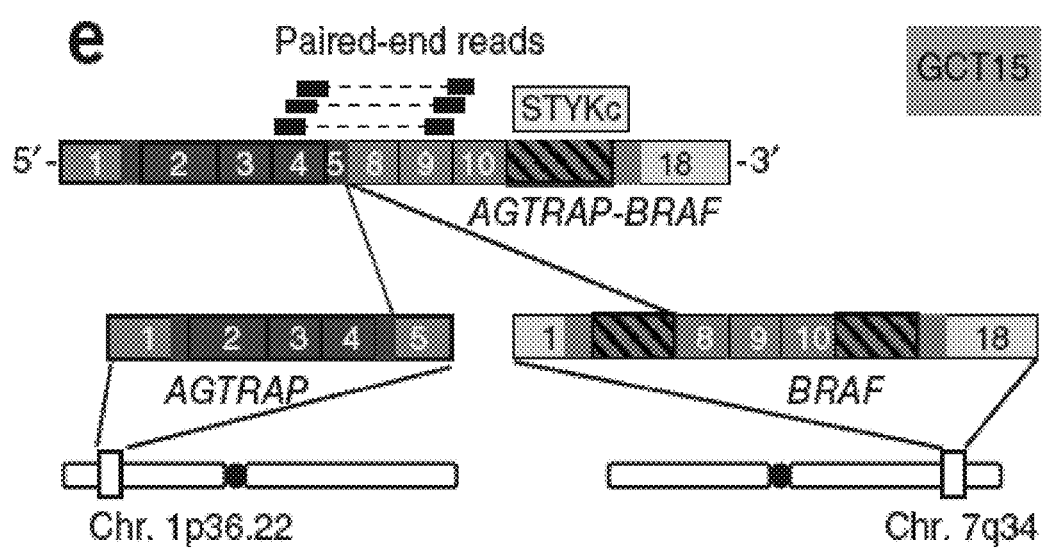

Unless defined otherwise, all terms of art, notations and other scientific terms or terminology used herein have the same meaning as is commonly understood by one of ordinary skill in the art to which this disclosure belongs. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

As used herein, "a" or "an" means "at least one" or "one or more."

As used herein, the term "gene fusion" refers to a chimeric genomic DNA, a chimeric messenger RNA, a truncated protein or a chimeric protein resulting from the fusion of at least a portion of a first gene to at least a portion of a second gene. The gene fusion need not include entire genes or exons of genes.

As used herein, the term "gene upregulated in cancer" refers to a gene that is expressed (e.g., mRNA or protein expression) at a higher level in cancer (e.g., prostate cancer) relative to the level in other tissue. In this context, "other tissue" may refer to, for example, tissues from different organs in the same subject or to normal tissues of the same or different type. In some embodiments, genes upregulated in cancer are expressed at a level between at least 10% to 300% higher than the level of expression in other tissue. For example, genes upregulated in cancer are frequently expressed at a level preferably at least 25%, at least 50%, at least 100%, at least 200%, or at least 300% higher than the level of expression in other tissue. In some embodiments, genes upregulated in prostate cancer are "androgen regulated genes."

As used herein, the term "gene upregulated in prostate tissue" refers to a gene that is expressed (e.g., mRNA or protein expression) at a higher level in prostate tissue relative to the level in other tissue. In some embodiments, genes upregulated in prostate tissue are expressed at a level between at least 10% to 300%. For example, genes upregulated in cancer are frequently expressed at a level preferably at least 25%, at least 50%, at least 100%, at least 200%, or at least 300% higher than the level of expression in other tissues. In some embodiments, genes upregulated in prostate tissue are exclusively expressed in prostate tissue.

As used herein, the term "transcriptional regulatory region" refers to the region of a gene comprising sequences that modulate (e.g., upregulate or downregulate) expression of the gene. In some embodiments, the transcriptional regulatory region of a gene comprises a non-coding upstream sequence of a gene, also called the 5' untranslated region (5'UTR). In other embodiments, the transcriptional regulatory region contains sequences located within the coding region of a gene or within an intron (e.g., enhancers).

As used herein, the term "androgen regulated gene" refers to a gene or portion of a gene whose expression is induced or repressed by an androgen (e.g., testosterone). The promoter region of an androgen regulated gene may contain an "androgen response element" that interacts with androgens or androgen signaling molecules (e.g., downstream signaling molecules).

As used herein, the terms "detect", "detecting" or "detection" may describe either the general act of discovering or discerning or the specific observation of a detectably labeled composition.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "probe" refers to an oligonucleotide, whether occurring naturally as in a purified restriction digest or produced synthetically, recombinantly or by PCR amplification, which is capable of hybridizing to at least a portion of another oligonucleotide of interest. A probe may be single-stranded or double-stranded. Probes are useful in the detection, identification and isolation of particular gene sequences. It is contemplated that any probe used in methods of the present disclosure will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the methods or reagents of the present disclosure be limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. An isolated nucleic acid is present in a form or setting that is different from that in which it is found in nature. In contrast, non-isolated nucleic acids are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the nucleic acid, oligonucleotide or polynucleotide often will contain, at a minimum, the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present invention.

DETAILED DESCRIPTION OF THE INVENTION

The present disclosure is based on the discovery of recurrent gene fusions in prostate cancer. The present disclosure provides diagnostic, research, and therapeutic methods that either directly or indirectly detect or target the gene fusions. The present disclosure also provides compositions for diagnostic, research, and therapeutic purposes.

I. Gene Fusions

The present disclosure identifies recurrent gene fusions indicative of cancer (e.g., melanoma or gastric cancer). In some embodiments, the gene fusions are the result of a chromosomal rearrangement of a transcriptional regulatory region of a first gene (e.g., an androgen regulated gene or other gene) or a RAF family member gene and an RAF family member gene or other gene. The gene fusions typically comprise a 5' portion from a transcriptional regulatory region of first gene (e.g., SLC45A3, RAF family member gene, AGTRAP or ESRP1) and a 3' portion from an RAF family member gene or ESRP1gene. The recurrent gene fusions have use as diagnostic markers and clinical targets for cancer.

In some embodiments, the 5' fusion partner is a transcriptional region of an androgen regulated gene. Genes regulated by androgenic hormones are of critical importance for the normal physiological function of the human prostate gland. They also contribute to the development and progression of prostate carcinoma. Recognized ARGs include, but are not limited to: TMPRSS2; SLC45A3; HERV-K_22q11.23; C15ORF21; FLJ35294; CANT1; PSA; PSMA; KLK2; SNRK; Seladin-1; and, FKBP51 (Paoloni-Giacobino et al., *Genomics* 44: 309 (1997); Velasco et al., *Endocrinology* 145(8): 3913 (2004)).

SLC45A3, also known as prostein or P501 S, has been shown to be exclusively expressed in normal prostate and prostate cancer at both the transcript and protein level (Kalos et al., Prostate 60, 246-56 (2004); Xu et al., Cancer Res 61, 1563-8 (2001)).

In some embodiments, gene fusions of the present disclosure comprise transcriptional regulatory regions of an ARG. The transcriptional regulatory region of an ARG may contain coding or non-coding regions of the ARG, including the promoter region. The promoter region of the ARG may further comprise an androgen response element) of the ARG.

In other embodiments, 5' fusion partners comprise a portion (e.g., a transcriptional regulatory region) of an Type-1 angiotensin II receptor-associated protein (AG-TRAP; NM_001040194, NM_001040195, NM_001040196 and NM_001040197) or epithelial splicing regulatory protein 1 (ESRP1; NM_017697) or a RAF family member gene.

In some embodiments, the 3' or 5' fusion partner comprises at least a portion of an ESRP1 gene or a RAF family member gene.

The BRAF gene makes a protein called B-RAF, which is involved in sending signals in cells and in cell growth. See, e.g., Ikawa et al., *Mol. Cell Biol.* 8(6):2651-54 (1988). This protein belongs to the raf/mil family of serine/threonine protein kinases. Though not desiring to be bound by theory, this protein is known to plays a role in regulating the MAP kinase/ERKs signaling pathway, which affects cell division, differentiation, and secretion. The BRAF gene may be mutated in a variety of cancer types, which causes a change in the B-RAF protein. See, e.g., Davies et al., *Nature* 417 (6892): 949-54 (2002); Wan et al. *Cell* 116:855-867 (2004) This can increase the growth and spread of cancer cells.

Mutations in this gene have been associated with cardio-faciocutaneous syndrome, a disease characterized by heart defects, mental retardation and a distinctive facial appearance. Mutations in this gene have also been associated with various cancers, including non-Hodgkin's lymphoma, colorectal cancer, malignant melanoma, thyroid carcinoma, non-small cell lung carcinoma, and adenocarcinoma of the lung.

c-raf is a gene that encodes a protein kinase called "Raf-1.". The Raf-1 protein functions in the MAPK/ERK signal transduction pathway as part of a protein kinase cascade. Raf-1 is a serine/threonine-specific kinase. Raf-1 is a MAP kinase kinase kinase (MAP3K) which functions downstream of the Ras family of membrane associated GTPases to which it binds directly. Activated Raf-1 can phosphorylate to activate the dual specificity protein kinases MEK1 and MEK2, which in turn phosphorylate to activate the serine/threonine specific protein kinases ERK1 and ERK2. Activated ERKs are pleiotropic effectors of cell physiology and play an important role in the control of gene expression involved in the cell division cycle, apoptosis, cell differentiation and cell migration.

The first identified raf gene is the oncogene v-raf (Mark et al., (Apr. 1984). *Science* 224 (4646): 285-9). Normal (non-oncogenic) cellular homologs of v-raf were soon found to be conserved components of eukaryotic genomes and it was shown that they could mutate and become oncogenes (Shimizu et al., (1986). *Int. Symp. Princess Takamatsu Cancer Res. Fund* 17: 85-91). A-Raf and B-Raf are two protein kinases with similar sequences to Raf-1. Mutations in B-Raf genes are found in several types of cancer (See, e.g., Davies et al., *Nature* 417 (6892): 949-54 (2002)). The Raf kinases are targets for anticancer drug development (Sridhar et al., (Apr. 2005). *Mol. Cancer Ther.* 4 (4): 677-85). There are several quantitative immunochemical methods available to detect Raf kinase inhibiting drugs (Olive (October 2004). Expert Rev Proteomics 1 (3): 327-41).

Human BRAF DNA has the nucleotide sequence described by Genbank Accession No. NG_007873. Human BRAF mRNA has the nucleotide sequence described by Genbank Accession No. NM_004333.

Human RAF1 DNA has the nucleotide sequence described by Genbank Accession No. NG_007467. Human RAF1 mRNA has the nucleotide sequence described by Genbank Accession No. NM_002880.

II. Antibodies

The gene fusion proteins of the present disclosure, including fragments, derivatives and analogs thereof, may be used as immunogens to produce antibodies having use in the diagnostic, screening, research, and therapeutic methods described below. The antibodies may be polyclonal or monoclonal, chimeric, humanized, single chain, Fv or Fab fragments. Various procedures known to those of ordinary skill in the art may be used for the production and labeling of such antibodies and fragments. See, e.g., Burns, ed., *Immunochemical Protocols*, 3$^{rd}$ ed., Humana Press (2005); Harlow and Lane, *Antibodies: A Laboratory Manual*, Cold Spring Harbor Laboratory (1988); Kozbor et al., *Immunology Today* 4: 72 (1983); Köhler and Milstein, *Nature* 256: 495 (1975). Antibodies or fragments exploiting the differences between the truncated or chimeric protein resulting from a gene fusion and their respective native proteins are particularly preferred.

III. Diagnostic and Screening Applications

The gene fusions described herein may be detectable as DNA, RNA or protein. Initially, the gene fusion is detectable as a chromosomal rearrangement of genomic DNA having a 5' portion from a first gene and a 3' portion from a second gene. Once transcribed, the gene fusion is detectable as a chimeric mRNA having a 5' portion from a first gene and a 3' portion from a second gene. Once translated, the gene fusion is detectable as fusion of a 5' portion from a first protein and a 3' portion from a second protein or a truncated version of a first or second protein. The truncated or fusion proteins may differ from their respective native proteins in amino acid sequence, post-translational processing and/or secondary, tertiary or quaternary structure. Such differences, if present, can be used to identify the presence of the gene fusion. Specific methods of detection are described in more detail below.

The present disclosure provides DNA, RNA and protein based diagnostic and screening methods that either directly or indirectly detect the gene fusions. The present disclosure also provides compositions and kits for diagnostic and screening purposes.

The diagnostic and screening methods of the present disclosure may be qualitative or quantitative. Quantitative methods may be used, for example, to discriminate between indolent and aggressive cancers via a cutoff or threshold level. Where applicable, qualitative or quantitative methods of embodiments of the disclosure include amplification of a target, a signal or an intermediary (e.g., a universal primer).

An initial assay may confirm the presence of a gene fusion but not identify the specific fusion. A secondary assay may then be performed to determine the identity of the particular fusion, if desired. The second assay may use a different detection technology than the initial assay.

The gene fusions may be detected along with other markers in a multiplex or panel format. Markers are selected for their predictive value alone or in combination with the gene fusions. Exemplary prostate cancer markers include, but are not limited to: AMACR/P504S (U.S. Pat. No. 6,262,245); PCA3 (U.S. Pat. No. 7,008,765); PCGEM1 (U.S. Pat. No. 6,828,429); prostein/P501S, P503S, P504S, P509S, P510S, prostase/P703P, P710P (U.S. Publication No. 20030185830); RAS/KRAS (Bos, Cancer Res. 49:4682-89 (1989); Kranenburg, Biochimica et Biophysica Acta 1756: 81-82 (2005)); and, those disclosed in U.S. Pat. Nos. 5,854, 206 and 6,034,218, 7,229,774, each of which is herein incorporated by reference in its entirety. Markers for other cancers, diseases, infections, and metabolic conditions are also contemplated for inclusion in a multiplex or panel format.

The diagnostic methods of the present disclosure may also be modified with reference to data correlating particular gene fusions with the stage, aggressiveness or progression of the disease or the presence or risk of metastasis. Ultimately, the information provided will assist a physician in choosing the best course of treatment for a particular patient.

A. Sample

Any sample suspected of containing the gene fusions may be tested according to the methods of the present disclosure. By way of non-limiting example, the sample may be tissue (e.g., a prostate biopsy sample or a tissue sample obtained by prostatectomy, a gastric biopsy sample, or a skin sample), blood, urine, semen, cells, fecal amples, cell secretions or a fraction thereof (e.g., plasma, serum, exosomes, urine supernatant, or urine cell pellet). A urine sample is preferably collected immediately following an attentive digital rectal examination (DRE), which causes prostate cells from the prostate gland to shed into the urinary tract.

In some embodiments, skin and/or gastic samples are obtained using known methods. For example, skin samples are generally obtained via biopsy of skin cells. There are four main types of skin biopsies: shave biopsy, punch biopsy, excisional biopsy, and incisional biopsy. All involve scraping or cutting a small sample of skin for analysis. Gastric cell samples are generally obtained via endoscopic or surgical biopsy or via a fecal sample.

The patient sample typically involves preliminary processing designed to isolate or enrich the sample for the gene fusion(s) or cells that contain the gene fusion(s). A variety of techniques known to those of ordinary skill in the art may be used for this purpose, including but not limited to: centrifugation; immunocapture; cell lysis; and, nucleic acid target capture (See, e.g., EP Pat. No. 1 409 727, herein incorporated by reference in its entirety).

B. DNA and RNA Detection

The gene fusions of the present disclosure may be detected as chromosomal rearrangements of genomic DNA or chimeric mRNA using a variety of nucleic acid techniques known to those of ordinary skill in the art, including but not limited to: nucleic acid sequencing; nucleic acid hybridization; and, nucleic acid amplification.

1. Sequencing

Illustrative non-limiting examples of nucleic acid sequencing techniques include, but are not limited to, chain terminator (Sanger) sequencing and dye terminator sequencing, or high throughput sequencing methods. The present disclosure is not intended to be limited to any particular methods of sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

2. Hybridization

Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with radio-, fluorescent- or antigen-labeled bases is localized and quantitated in the tissue using autoradiography, fluorescence microscopy or immunohistochemistry. ISH can also use two or more probes, labeled with radioactivity or the other non-radioactive labels, to simultaneously detect two or more transcripts.

a. FISH

In some embodiments, fusion sequences are detected using fluorescence in situ hybridization (FISH). The preferred FISH assays for methods of embodiments of the present disclosure utilize bacterial artificial chromosomes (BACs). These have been used extensively in the human genome sequencing project (see *Nature* 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

b. Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limited to: printing with fine-pointed pins onto glass slides; photolithography using pre-made masks; photolithography using dynamic micromirror devices; ink-jet printing; or, electrochemistry on microelectrode arrays.

Southern and Northern blotting may be used to detect specific DNA or RNA sequences, respectively. In these techniques DNA or RNA is extracted from a sample, fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

3. Amplification

Chromosomal rearrangements of genomic DNA and chimeric mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Pat. No. 7,374,885 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPaS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

4. Detection Methods

Non-amplified or amplified gene fusion nucleic acids can be detected by any conventional means. For example, the gene fusions can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174; Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs, including fluorescence resonance energy transfer (FRET) labels, are disclosed in, for example U.S. Pat. Nos. 6,534,274 and 5,776,782, each of which is herein incorporated by reference in its entirety.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label should be maximal. A FRET binding event can be conveniently measured through standard fluorometric detection means well known in the art (e.g., using a fluorimeter).

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DAB-CYL and EDANS). Molecular beacons are disclosed, for example, in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in method of embodiments of the present disclosure. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products methods of embodiments of the present disclosure. See, e.g., U.S. Pat. No. 5,814,447 (herein incorporated by reference in its entirety).

C. Protein Detection

The gene fusions of the present disclosure may be detected as truncated or chimeric proteins using a variety of protein techniques known to those of ordinary skill in the art, including but not limited to: protein sequencing and immunoassays.

1. Sequencing

Illustrative non-limiting examples of protein sequencing techniques include, but are not limited to, mass spectrometry and Edman degradation.

Mass spectrometry can, in principle, sequence any size protein. A protein is digested by an endoprotease, and the resulting solution is passed through a high pressure liquid chromatography column. At the end of this column, the solution is sprayed out of a narrow nozzle charged to a high positive potential into the mass spectrometer. The charge on the droplets causes them to fragment until only single ions remain. The peptides are then fragmented and the mass-charge ratios of the fragments measured. The mass spectrum is analyzed by computer and often compared against a database of previously sequenced proteins in order to determine the sequences of the fragments. The process is then repeated with a different digestion enzyme, and the overlaps in sequences are used to construct a sequence for the protein.

In the Edman degradation reaction (see, e.g., Edman, Acta Chem. Scand. 4:283-93 (1950)), the peptide to be sequenced is adsorbed onto a solid surface (e.g., a glass fiber coated with polybrene). Though there are various well known modifications to this procedure (including automated modifications), one exemplary method involves the use of the Edman reagent, phenylisothiocyanate (PITC), which is added, together with a mildly basic buffer solution of 12% trimethylamine, to an adsorbed peptide, and which reacts with the amine group of the N-terminal amino acid of the adsorbed peptide. The terminal amino acid derivative can then be selectively detached by the addition of anhydrous acid. The derivative isomerizes to give a substituted phenylthiohydantoin, which can be washed off and identified by chromatography, and the cycle can be repeated. The efficiency of each step is about or over 98%, which allows about 50 amino acids to be reliably determined.

2. Immunoassays Illustrative non-limiting examples of immunoassays include, but are not limited to: immunoprecipitation; Western blot; ELISA; immunohistochemistry; immunocytochemistry; immunochromatography; flow cytometry; and, immuno-PCR. Polyclonal or monoclonal antibodies detectably labeled using various techniques known to those of ordinary skill in the art (e.g., colorimetric, fluorescent, chemiluminescent or radioactive labels) are suitable for use in the immunoassays.

Immunoprecipitation is the technique of precipitating an antigen out of solution using an antibody specific to that antigen. The process can be used to identify proteins or protein complexes present in cell extracts by targeting a specific protein or a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme.

The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and optionally sorting microscopic particles or cells suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

D. Data Analysis

In some embodiments, a computer-based analysis program is used to translate the raw data generated by the detection assay (e.g., the presence, absence, or amount of a given gene fusion or other markers) into data of predictive value for a clinician. The clinician can access the predictive data using any suitable means. Thus, in some preferred embodiments, the present disclosure provides the further benefit that the clinician, who may not be specifically trained in genetics or molecular biology, need not understand the raw data. The data is can be presented directly to the clinician in its most useful form. The clinician is may then be then able to immediately utilize the information in order to optimize the care of the subject.

The present disclosure contemplates any method capable of receiving, processing, and transmitting the information to and from laboratories conducting the assays, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data may then be prepared in a format suitable for interpretation by a treating clinician. For example, rather than providing raw expression data, the prepared format may represent a diagnosis or risk assessment (e.g., likelihood of cancer being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose, for example, further or altered intervention or counseling based on the results. In some embodiments, the data is used for research use. For example, the data may be used to further optimize the inclusion or elimination of markers as useful indicators of a particular condition or stage of disease.

E. In Vivo Imaging

The gene fusions of the present disclosure may also be detected using in vivo imaging techniques, including but not limited to: radionuclide imaging; positron emission tomography (PET); computerized axial tomography, X-ray or magnetic resonance imaging methods, fluorescence detection, and chemiluminescent detection. In some embodiments, in vivo imaging techniques are used to visualize the presence of or expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present disclosure are described below.

The in vivo imaging methods of the present disclosure are useful in the diagnosis of cancers that express the cancer markers of the present invention (e.g., prostate cancer, gastric cancer, melanoma). In vivo imaging is used to visualize the presence of a marker indicative of the cancer. Such techniques allow for diagnosis without the use of an unpleasant biopsy. The in vivo imaging methods of the present disclosure are also useful for providing prognoses to cancer patients. For example, the presence of a marker indicative of cancers likely to metastasize can be detected. The in vivo imaging methods of the present disclosure can further be used to detect metastatic cancers in other parts of the body.

In some embodiments, reagents (e.g., antibodies) specific for the gene fusions of the present disclosure are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990]) have described an optimized antibody-chelator for the radioimmunoscintographic imaging of tumors using Indium-111 as the label. Griffin et al., (J Clin Onc 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a gene fusion of the present disclosure). When active, it leads to a reaction that emits light. A CCD camera and software is used to capture the image and analyze it.

F. Compositions & Kits

Any of these compositions, alone or in combination with other compositions of the present disclosure, may be provided in the form of a kit. For example, the single labeled probe and pair of amplification oligonucleotides may be provided in a kit for the amplification and detection of gene fusions of the present invention. Kits may further comprise appropriate controls and/or detection reagents. The probe and antibody compositions of the present disclosure may also be provided in the form of an array.

Compositions for use in the diagnostic methods of the present invention include, but are not limited to, probes, amplification oligonucleotides, and antibodies. Particularly preferred compositions detect a product only when a first gene fuses to a second gene gene. These compositions include: a single labeled probe comprising a sequence that hybridizes to the junction at which a 5' portion from a first gene fuses to a 3' portion from a second gene (i.e., spans the gene fusion junction); a pair of amplification oligonucleotides wherein the first amplification oligonucleotide comprises a sequence that hybridizes to a transcriptional regulatory region of a 5' portion from a first gene fuses to a 3' portion from a second gene; an antibody to an amino-terminally truncated protein resulting from a fusion of a first protein to a second gene; or, an antibody to a chimeric protein having an amino-terminal portion from a first gene and a carboxy-terminal portion from a second gene. Other useful compositions, however, include: a pair of labeled probes wherein the first labeled probe comprises a sequence that hybridizes to a transcriptional regulatory region of a first gene and the second labeled probe comprises a sequence that hybridizes to a second gene.

IV. Companion Diagnostics

In some embodiments, the present disclosure provides compositions and methods for determining a treatment course of action in response to a subject's gene fusion status. For example, screening for RAF kinase fusions is useful in identifying people with cancer who benefit from treatment with RAF kinase inhibitors. Individuals found to a have a gene fusions that comprises a RAF family member gene fusion are then treated with a RAF inhibitor.

The present disclosure is not limited to a particular RAF inhibitor or RAF pathway inhibitor. RAF kinase inhibitors are known in the art. In some embodiments, inhibitors are antisense oligonucleotides, siRNA, antibodies and small molecules. Exemplary small molecule inhibitors include, but are not limited to, RAF265, XL281, AZD6244, PLX4032, PLX4720, GDC 0879, AZ 628, Sorafenib (BAY43-9006) and those described in US Pat. Pub. No. 2010/0063088 and U.S. Pat. No. 7,199,137, each of which is herein incorporated by reference in its entirety.

BAY43-9006 has the chemical name N-(3-trifluoromethyl-4-chlorophenyl)-N'-(4-(2-methylcarbamoyl pyridin-4-yl)oxyphenyl)urea and the structure:

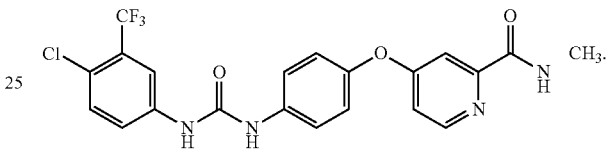

PLX4720 has the structure:

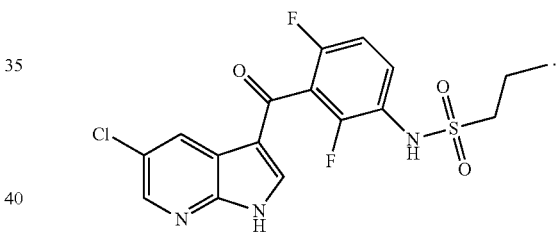

AZ 628 has the structure:

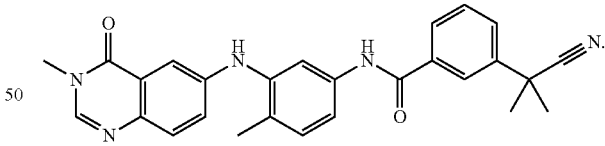

GDC 0879 has the structure:

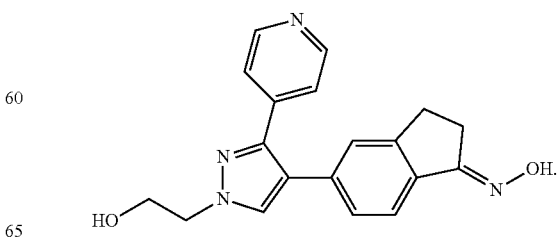

PLX4032 has the structure:

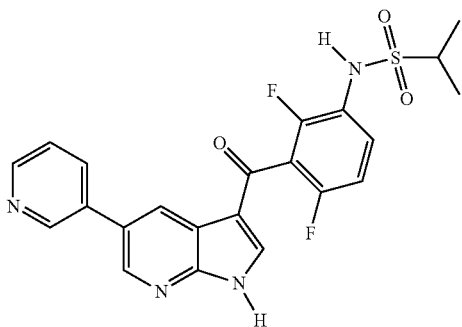 [SMILES: CC(C)S(=O)(=O)Nc1ccc(F)c(C(=O)c2c[nH]c3ncc(-c4cccnc4)cc23)c1F]

RAF265 has the structure:

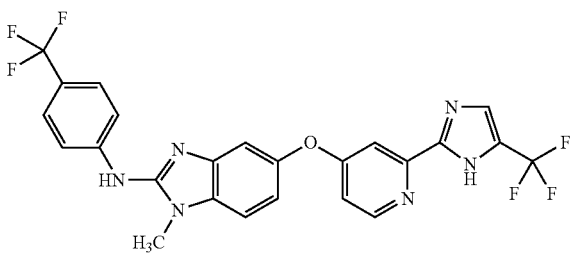 [SMILES: Cn1c(Nc2ccc(C(F)(F)F)cc2)nc2cc(Oc3ccnc(-c4ncc(C(F)(F)F)[nH]4)c3)ccc21]

AZD6244 has the structure:

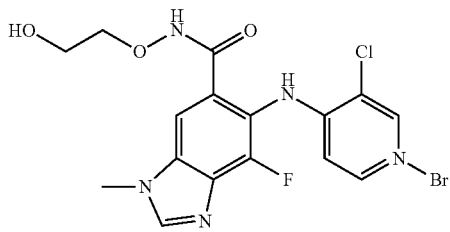

V. Drug Screening Applications

In some embodiments, the present disclosure provides drug screening assays (e.g., to screen for anticancer drugs). The screening methods of the present disclosure utilize cancer markers identified using the methods of the present invention (e.g., including but not limited to, gene fusions of the present invention). For example, in some embodiments, the present disclosure provides methods of screening for compounds that alter (e.g., decrease) the expression of gene fusions. The compounds or agents may interfere with transcription, by interacting, for example, with the promoter region. The compounds or agents may interfere with mRNA produced from the fusion (e.g., by RNA interference, antisense technologies, etc.). The compounds or agents may interfere with pathways that are upstream or downstream of the biological activity of the fusion. In some embodiments, candidate compounds are antisense or interfering RNA agents (e.g., oligonucleotides) directed against cancer markers. In other embodiments, candidate compounds are antibodies or small molecules that specifically bind to a cancer marker regulator or expression products of the present disclosure and inhibit its biological function.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method.

In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

Specifically, the present disclosure provides screening methods for identifying modulators, i.e., candidate or test compounds or agents (e.g., proteins, peptides, peptidomimetics, peptoids, small molecules or other drugs) which bind to gene fusions of the present disclosure, have an inhibitory (or stimulatory) effect on, for example, cancer marker expression or cancer marker activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds that inhibit the activity or expression of cancer markers are useful in the treatment of proliferative disorders, e.g., cancer, particularly prostate, gastric or skin cancer.

In one embodiment, the disclosure provides assays for screening candidate or test compounds that are substrates of a cancer marker protein or polypeptide or a biologically active portion thereof. In another embodiment, the disclosure provides assays for screening candidate or test compounds that bind to or modulate the activity of a cancer marker protein or polypeptide or a biologically active portion thereof.

The test compounds of the present disclosure can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222: 301 [1991]).

In one embodiment, an assay is a cell-based assay in which a cell that expresses a cancer marker mRNA or protein or biologically active portion thereof is contacted with a test compound, and the ability of the test compound to the modulate cancer marker's activity is determined. Determining the ability of the test compound to modulate cancer marker activity can be accomplished by monitoring, for example, changes in enzymatic activity, destruction or mRNA, or the like.

The ability of the test compound to modulate cancer marker binding to a compound, e.g., a cancer marker substrate or modulator, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the cancer marker is coupled with a radioisotope or enzymatic label to monitor the ability of a test compound to modulate cancer marker binding to a cancer marker substrate in a complex. For example, compounds (e.g., substrates) can be labeled with $^{125}I$, $^{35}S$ $^{14}C$ or $^3H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a cancer marker substrate) to interact with a cancer marker with or without the labeling of any of the interactants can be evaluated. For example, a microphysiometer can be used to detect the interaction of a compound with a cancer marker without the labeling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker protein or biologically active portion thereof is contacted with a test compound and the ability of the test compound to bind to the gene fusion protein, mRNA, or biologically active portion thereof is evaluated. Preferred biologically active portions of the gene fusion proteins or mRNA to be used in assays of the present disclosure include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

In another embodiment, determining the ability of the cancer marker protein or mRNA to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize cancer markers, an anti-cancer marker antibody or its target molecule to facilitate separation of complexed from non-complexed forms of one or both of the proteins, as well as to accommodate automation of the assay. Binding of a test compound to a cancer marker protein, or interaction of a cancer marker protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with cancer marker protein or target molecules but which do not interfere with binding of the cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 [1998]; Hageand Tweed J. Chromatogr. Biomed. Sci. App 1 699:499-525 [1997]). Further, fluorescence energy transfer may also be conveniently utilized, as described herein, to detect binding without further purification of the complex from solution.

The assay can include contacting the cancer markers protein, mRNA, or biologically active portion thereof with a known compound that binds the cancer marker to form an assay mixture, contacting the assay mixture with a test compound, and determining the ability of the test compound to interact with a cancer marker protein or mRNA, wherein determining the ability of the test compound to interact with a cancer marker protein or mRNA includes determining the ability of the test compound to preferentially bind to cancer markers or biologically active portion thereof, or to modulate the activity of a target molecule, as compared to the known compound.

To the extent that cancer markers can, in vivo, interact with one or more cellular or extracellular macromolecules, such as proteins, inhibitors of such an interaction are useful. A homogeneous assay can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, which utilizes this approach for immunoassays). The addition of a test substance that competes with and displaces one of the species from the preformed complex will result in the generation of a signal above background. In this way, test substances that disrupt target gene product-binding partner interaction can be identified. Alternatively, gene fusion protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with gene fusions and are involved in gene fusion activity. Such gene fusion-bps can be activators or inhibitors of signals by the cancer marker proteins or targets as, for example, downstream elements of a cancer markers-mediated signaling pathway.

Modulators of gene fusion expression can also be identified. For example, a cell or cell free mixture is contacted with a candidate compound and the expression of cancer marker mRNA or protein evaluated relative to the level of expression of cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer markers mRNA or protein expression can be determined by methods described herein for detecting cancer markers mRNA or protein.

A modulating agent can be identified using a cell-based or a cell free assay, and the ability of the agent to modulate the activity of a cancer markers protein can be confirmed in vivo, e.g., in an animal such as an animal model for a disease (e.g., an animal with prostate cancer or metastatic prostate cancer; or an animal harboring a xenograft of a prostate cancer from an animal (e.g., human) or cells from a cancer resulting from metastasis of a prostate cancer (e.g., to a lymph node, bone, or liver), or cells from a prostate cancer cell line.

This disclosure further pertains to novel agents identified by the above-described screening assays (see e.g., below description of cancer therapies). Accordingly, it is within the scope of this disclosure to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

VI. Transgenic Animals

The present disclosure contemplates the generation of transgenic animals comprising an exogenous cancer marker gene (e.g., gene fusion) of the present disclosure or mutants and variants thereof (e.g., truncations or single nucleotide polymorphisms). In preferred embodiments, the transgenic animal displays an altered phenotype (e.g., increased or decreased presence of markers) as compared to wild-type animals. Methods for analyzing the presence or absence of such phenotypes include but are not limited to, those disclosed herein. In some preferred embodiments, the transgenic animals further display an increased or decreased growth of tumors or evidence of cancer.

The transgenic animals of the present disclosure find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., *supra* /1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present disclosure and are not to be construed as limiting the scope thereof.

Example 1

Materials and Methods

Samples and paired-end library preparation for Illumina sequencing. Prostate cancer tissues negative for ETS family gene rearrangements were selected for paired-end sequencing from the University of Michigan tissue core with informed consent from subjects. (SPORE in Prostate Cancer (Tissue/Serum/Urine) Bank Institutional Review Board #1994-0481). Total RNA was isolated with Trizol (Invitrogen), according to the manufacturer's instructions. Quality assessment of RNA was performed with the Agilent Bioanalyzer 2100 (Agilent Technologies). Paired-end libraries (n=15) for sequencing with Illumina Genome Analyzer II were prepared according to the protocol provided by Illumina, with minor modifications, with the mRNA-seq sample prep kit (Illumina). Sequence analysis was carried out by the Illumina data analysis pipeline.

Nomination of prostate gene fusions. Mate-pair transcriptome reads were mapped to the human genome (hg18) and Refseq transcripts, allowing up to two mismatches, with the Illumina Genome Analyzer Pipeline software ELAND (Efficient Alignment of Nucleotide Databases). Sequence alignments were subsequently processed to nominate gene fusions, using previously described methodology (Maher, C. A. et al. *Nature* 458, 97-101 (2009)). In brief, mate pairs were processed to identify any that either encompassed or spanned the fusion junction. Encompassing mate pairs refer to those in which each read aligns to an independent transcript, thereby encompassing the fusion junction. In contrast, spanning mate pairs refer to those in which one sequence read aligns to a gene and its mate spans the fusion junction. Both categories undergo a series of filtering steps to remove putative false positives before being merged together to generate the final chimera nominations.

Cloning of full-length fusion transcript. The full-length fusion transcripts of SLC45A3-BRAF and ESRP1-RAF1 were cloned into pCR8/GW/TOPO Entry vector by TA cloning method (Invitrogen). All entry vector clones were sequence-confirmed and recombined into the Gateway pcDNA-DEST40 mammalian expression vector (Invitrogen) and the pAd/CMV/V5-DEST Adenoviral expression system (Invitrogen) by LR Clonase II (Invitrogen). Plasmids with N terminus Flag and C terminus V5 tags were generated for initial verification of protein expression in HEK293 cells.

Cell invasion and proliferation assays. Equal numbers of cells were plated into 96-well plates, and a cell proliferation assay was performed using WST-1 reagent (Roche) following the manufacturer's protocol. For the Boyden chamber Matrigel invasion assay, equal numbers of cells were plated into each Matrigelcoated transwell in the presence of sorafenib or U0126 (Calbiochem) or DMSO (Sigma). Invasion assays were performed as described previously (Kleer, C. G. et al. Proc. Natl. Acad. Sci. USA 100, 11606-11611 (2003); Cao, Q. et al. Oncogene 27, 7274-7284 (2008)).

In vitro soft agar growth. For in vitro growth in soft agar, 2 ml of 0.6% SeaPlaque GTG Agarose (Cambrex) dissolved in complete keratinocyte supplement-free medium (Invitrogen) was poured into six-well dishes. After polymerization, a second layer containing 2 ml of 0.4% agar in complete keratinocyte supplement-free medium, and RWPE cells stably expressing SLC45A3-BRAF or ESRP1-RAF1 ($1\times10^4$ cells per well) were poured on top. The next day, cells were treated with sorafenib or U0126 (10 µM) in 1 ml of supplement-free keratinocyte medium. Soft-agar assay plates were incubated for 14 d at 37° C. MEK inhibitor (U0126) or sorafenib was changed once a week. Each experimental condition was done in triplicate. On day 14, colonies larger than 40 µm in diameter were counted.

Fluorescence in situ hybridization. FISH hybridizations were performed on tissue microarrays of prostate, melanoma, gastric, endometrial and liver cancer types. Rearrangement-positive cases identified from tissue microarray were further validated on individual formalin-fixed and paraffin-embedded sections. Bacterial artificial chromosome clones were selected from the University of California-Santa Cruz genome browser and purchased through BACPAC resources (Children's Hospital, Oakland, Calif.). After colony purification, Midi-prep DNA was prepared with QiagenTips-100 (Qiagen). DNA was labeled by nick translation with biotin-16-dUTP and digoxigenin-11-dUTP (Roche). Probe DNA was precipitated and dissolved in hybridization mixture containing 50% formamide, 2× saline sodium citrate, 10% dextran sulfate (Chemicon International) and 1% Denhardt's solution (Sigma). Approximately 200 ng of labeled probe was hybridized to normal human chromosomes to confirm the map position of each BAC clone. FISH signals were obtained with digoxigenin-fluorescein and Alexa Fluor 594 conjugates, to obtain green and red colors, respectively. Fluorescence images were captured with a high-resolution charge-coupled device camera controlled by In Situ Imaging System image processing software (Metasystems).

MEK-ERK signaling pathway analysis. Stable pooled populations of RWPE cells expressing SLC45A3-BRAF or ESRP1-RAF1 were maintained in supplement-free medium without supplements for 2 h. For MEK inhibitor treatments, U0126 (10 µM) was added in the supplement-free keratinocyte medium for 2 h. MEK and ERK activation was assessed by western blot analysis with antibodies to phospho-MEK or ERK and total MEK or ERK antibodies (Cell Signaling Technologies).

Statistical analyses. All data are presented as means±s.e.m., and significance was determined by two-tailed Student's t test.

Cell lines and Tissues. NIH3T3, RWPE-1, and HEK293 cell lines were obtained from the American Type Culture Collection. Prostate cancer tissues were obtained from the University of Michigan tissue core and University of Michigan Rapid Autopsy Program which are part of the University of Michigan Prostate Cancer Specialized Program Of Research Excellence (S.P.O.R.E). Five different tissue microarrays containing a total of 512 samples with 90-100 samples each comprising samples for prostate cancer progression with benign prostate, PIN prostate, prostate tumors and warm autopsy samples. Each of the tissue microarrays were used for the FISH evaluation of both RAF1 and BRAF. Prostate tissues obtained from the radical prostatectomy series at the University Hospital Ulm (Ulm, Germany) comprised of 149 cases of primary prostate cancer (n=136) and lymph node metastasis (n=13) from patients that underwent radical prostatectomy and lymph node dissection between 1989 and 2001 at Ulm University (Ulm, Germany) and were collected under an IRB approved protocol. The mean patient age was 64. The distribution of Gleason pattern was as follows: GS 6 (2%), GS 7 (24%), GS 8-10 (68%), GS N/A (6%). The pT staging distribution is as follows: pT2 (5%), pT3 (93%), pT N/A (2%). The PSA levels range from 0.6-262 ng ml-1 (median 23.75 ng ml-1). 25 (18%) patients received androgen-deprivatio therapy pre-operatively. A tissue microarray was constructed using three 0.6 mm high density cancer tissue cores per case. A small cohort of 59 transurethral resection of prostate (TURP) FFPE material was retrieved from McGill University Hospitals (Montreal, Canada). The patients had been treated with one or multiple therapeutic protocols (radiation therapy, brachytherapy and/or androgen deprivation therapy). The castration-resistant status was determined clinically based on PSA levels and disease progression under treatment. Tissue cores at diameters of 0.6 mm were obtained from areas containing high density tumor and subjected to tissue microarray construction.

Real Time PCR validation. Quantitative PCR (QPCR) was performed using Power SYBR Green Mastermix (Applied Biosystems) on an Applied Biosystems StepOnePlus Real-Time PCR System. All oligonucleotide primers were obtained from Integrated DNA Technologies and are listed below. The GAPDH primer was used as a control. All assays were performed and repeated twice and results were plotted as average fold change relative to GAPDH.

```
SLC45A3 F
                                       (SEQ ID NO: 1)
5'-AGCCGCGCGCCTCGGCCA-3'

BRAF R
                                       (SEQ ID NO: 2)
5'-ATCAGGAATCTCCCAATCATCACT-3'

SLC45A3 F
                                       (SEQ ID NO: 3)
5'-GTACCAGCCCCACCCCTCTATCC-3'

SLC45A3 R
                                       (SEQ ID NO: 4)
5'-TCAGTGGACAGGAAACGCACCATA-3'
```

-continued

BRAF EX8-Stop F  
(SEQ ID NO: 5)  
5'-GCCCCAAATTCTCACCAGTCCGTC-3'

BRAF EX8-Stop R  
(SEQ ID NO: 6)  
5'-TCAGTGGACAGGAAACGCACCA-3'

BRAF EX10-Stop F  
(SEQ ID NO: 7)  
5'-ATGAAACACTTGGTAGACGGGA-3'

BRAF EX10-Stop R  
(SEQ ID NO: 8)  
5'-TCAGTGGACAGGAAACGCACCA-3'

BRAF EX2 F  
(SEQ ID NO: 9)  
5'-AACATATAGAGGCCCTATTGGACA-3'

BRAF EX3 R  
(SEQ ID NO: 10)  
5'-AGAAGATGTAACGGTATCCATTG-3'

BRAF EX4 F  
(SEQ ID NO: 11)  
5'-GGAGTTACAGTCCGAGACAGTCTAA-3'

BRAF EX5 R  
(SEQ ID NO: 12)  
5'-CAGTAAGCCAGGAAATATCAGTGTC-3'

BRAF EX6 F  
(SEQ ID NO: 13)  
5'-AGCGTTGTAGTACAGAAGTTCCACT-3'

BRAF EX7 R  
(SEQ ID NO: 14)  
5'-AGATGTTAGGGCAGTCTCTGCTA-3'

BRAF EX8 F  
(SEQ ID NO: 15)  
5'-TGTGCATATAAACACAATAGAACCTG-3'

BRAF EX10 R  
(SEQ ID NO: 16)  
5'-TTCGATTCCTGTCTTCTGAGG-3'

BRAF EX11F  
(SEQ ID NO: 17)  
5'-AAAACACTTGGTAGACGGGACTC-3'

BRAF EX12R  
(SEQ ID NO: 18)  
5'-CTTGTAACTGCTGAGGTGTAGGTG-3'

BRAF EX13 F  
(SEQ ID NO: 19)  
5'-TTGTATCACCATCTCCATATCATTG-3'

BRAF EX14 R  
(SEQ ID NO: 20)  
5'-GGATGATTGACTTGGCGTGTA-3'

BRAF EX15 F  
(SEQ ID NO: 21)  
5'-CTACAGTGAAATCTCGATGGAGTG-3'

BRAF EX16 R  
(SEQ ID NO: 22)  
5'-TCATACAGAACAATTCCAAATGC-3'

BRAF EX17 F  
(SEQ ID NO: 23)  
5'-CGAGGATACCTGTCTCCAGAT-3'

BRAF EX18 R  
(SEQ ID NO: 24)  
5'-GATGCACTGCGGTGAATTTTT-3'

BRAF 3'UTR F  
(SEQ ID NO: 25)  
5'-AGTGAGAGAGTTCAGGAGAGTAGCA-3'

BRAF 3'UTR R  
(SEQ ID NO: 26)  
5'-AAGTATAAATTTTAGTTTGGGGAAAAA-3'

RAF1 EX5 F  
(SEQ ID NO: 27)  
5'-CATGAGCACTGTAGCACCAAA-3'

ESRP1 EX14 R  
(SEQ ID NO: 28)  
5'-AGCAGCTGTAGGGAAGTAGCC-3'

ESRP1 EX13 F  
(SEQ ID NO: 29)  
5'-GTACTACCCAGCAGGCACTCA-3'

RAF1 Ex6 R  
(SEQ ID NO: 30)  
5'-CTGGGACTCCACTATCACCAA-3'

RAF1 F  
(SEQ ID NO: 31)  
5'-ATGGAGCACATACAGGGAGCT-3'

ESRP1 R  
(SEQ ID NO: 32)  
5'-TTAAATACAAACCCATTCTTTGG-3'

ESRP1 F  
(SEQ ID NO: 33)  
5'-ATGACGGCCTCTCCGGATTA-3'

RAF1 R  
(SEQ ID NO: 34)  
5'-CTAGAAGACAGGCAGCCTCG-3'

DUSP6 F  
(SEQ ID NO: 35)  
5'-CCGCAGGAGCTATACGAGTC-3'

DUSP6 R  
(SEQ ID NO: 36)  
5'-CCTCGTCCTTGAGCTTCTTG-3'

SPRY2 F  
(SEQ ID NO: 37)  
5'-CCCCTCTGTCCAGATCCATA-3'

SPRY2 R  
(SEQ ID NO: 38)  
5'-CCCAAATCTTCCTTGCTCAG-3'

AGTRAP F  
(SEQ ID NO: 39)  
5'-ATCCCTTTGCAGTCCCAGA-3'

BRAF R  
(SEQ ID NO: 40)  
5'-CTGTGGAATTGGAATGGATTTT-3'

GAPDH F  
(SEQ ID NO: 41)  
5'-TGCACCACCAACTGCTTAGC-3'

GAPDH R  
(SEQ ID NO: 42)  
5'-GGCATGGACTGTGGTCATGAG-3'

Gene Expression Profiling. LNCaP and VCaP cells were starved for 48 hours and treated with 1 nM R1881 for 24 and 48 hours and RNA isolated from these cells were used for microarray analysis. Gene expression microarray profiling was performed using the Agilent Whole Human Genome Oligo Microarray according to the manufacturer's protocol.

Confirmation of SLC45A3-BRAF and ESRP1-RAF1 protein expression by Western Blotting. The ESRP1-RAF1 fusion positive prostate cancer tissue and fusion negative tissues were homogenized in NP40 lysis buffer (50 mM Tris-HCl, 1% NP40, pH 7.4, Sigma, St. Louis, Mo.), and complete protease inhibitor mixture (Roche) and phosphatase inhibitor (EMD Bioscience). Fresh frozen material for the SLC45A3-BRAF index case was not available for similar assay. For evaluating the expression and to assess the molecular weight of the fusion protein in the fusion positive tissues, HEK293 cells were separately transfected with SLC45A3-BRAF and ESRP1-RAF1 fusion constructs (cloned in pDEST40 expression vector—Invitrogen). A vector control and the transfected cells were lysed in NP40 lysis buffer with protease inhibitor. Fifteen micrograms of each protein extract were boiled in sample buffer, separated by SDS-PAGE, and transferred onto Polyvinylidene Difluoride membrane (GE Healthcare). The membrane was incubated for one hour in blocking buffer (Tris-buffered saline, 0.1% Tween (TBS-T), 5% nonfat dry milk) and incubated overnight at 4° C. with anti-BRAF (Santa Cruz) and anti-RAFT mouse monoclonal antibody (1:1000 in blocking buffer (BD Bioscience). Following three washes with TBS-T, the blot was incubated with horseradish peroxidase-conjugated secondary antibody and the signals visualized by enhanced chemiluminescence system as described by the manufacturer (GE Healthcare). Blot was reprobed with anti-actin mouse monoclonal (1:5000, Sigma) antibodies.

Foci Formation Assay. NIH3T3 cells ($1.5 \times 10^5$) in 35-mm plastic dishes were transfected with 2 µg of DNA of the plasmid of interest. All the transfections were performed using Fugene 6 according to the manufacturer's protocol (Roche Applied Sciences). Plasmids for fusion transcripts SLC45A3-BRAF, BRAF Ex8-stop, and BRAF Ex10-stop and BRAF mutant V600E were used along with control plasmids (pDEST40 and pBABE respectively). Three days after transfection, cells were split into 140-mm dishes containing DMEM with 5% Calf Serum (Life Technologies). The cultures were fed every 3-4 days. After 3 weeks, the cells were stained with 0.2% crystal violet in 70% ethanol for the visualization of foci, and were counted on colony counter (Oxford Optronix, software v4.1, 2003). Foci counts were further confirmed manually.

BRAF$^{V600}$ Mutation Detection by Pyrosequencing. One to 2 µg of total RNA isolated from fresh frozen localized prostate cancer (n=229), metastatic prostate cancer (n=37) and benign prostate (n=8) tissue samples, and a panel of melanoma (n=34), gastric cancer (n=25) were converted into cDNA using Superscript II Reverse Transcriptase (Invitrogen) according to manufacturer's instructions. Biotinylated sequencing templates were generated by PCR amplification of a 375 bp fragment spanning the mutation in codon 600 (V600, Exon 15) of the BRAF gene using primers from PyroMark Q24 BRAF kit (Biotage-Qiagen) according to manufacturer's instructions. Ten pl of the biotinylated PCR products were immobilized on streptavidin coated Sepharose beads (Streptavidin Sepharose High Performance, GE Healthcare) using Pyromark Q24 Vacuum Prep Workstation, followed by removal of non-biotinylated strand by sodium hydroxide denaturation followed by wash in neutralization buffer and 70% ethanol. The single stranded biotinylated templates were then mixed with 0.3 mM sequencing primer and 'sequencing by synthesis' was carried out through dispensation of the query nucleotide sequence using PyroMark Q24 platform, as described before. The nucleotide sequence ACAGA/TGAAA (SEQ ID NO:43) for codon 600 was analyzed and visualized by Pyromark Q24 1.0.10 software. A panel of 9 melanoma cell lines (SK-MEL-2, SK-MEL-5, SK-MEL-19, SK-MEL-28, SK-MEL-29, SK-MEL-103, G-361, Malme-3M, mel-1 with known mutation status was used to serve as assay standards.

NIH3T3-SLC45A3-BRAF or RWPE-SLC45A3-BRAF Xenograft Models. Four week old male Balb C nu/nu mice were purchased from Charles River, Inc. (Charles River Laboratory, Wilmington, Mass.). Stable polyclonal NIH3T3 cells or RWPE over-expressing fusion transcript SLC45A3-BRAF or vector pDEST40 or single clone ($5 \times 10^6$ cells) were resuspended in 100 pl of saline with 20% Matrigel (BD Biosciences). Cells were implanted subcutaneously into the left flank region of the mice. Mice were anesthetized using a cocktail of xylazine (80-120 mg kg-1 IP) and ketamine (10 mg kg-1 IP) for chemical restraint before implantation. Ten mice were included in each group. Growth in tumor volume was recorded weekly by using digital calipers and tumor volumes were calculated using the formula $(\pi/6)$ $(L \times W^2)$, where "L"=length of the tumor and "W"=width. All procedures involving mice were approved by the University Committee on Use and Care of Animals (UCUCA) at the University of Michigan and conform to their relevant regulatory standards.

Results

To search for druggable rearrangements in prostate cancer, paired-end, massively parallel transcriptome sequencing was used to prioritize candidate gene fusions in prostate tumors by generating a score derived from the quantity of mate-pair reads that meet a series of computational filters implemented to reduce potential false-positive chimera nominations (Maher et al. *Proc. Natl. Acad. Sci. USA* 106, 12353-12358 (2009)). Prioritization histograms for two ETS rearrangement—positive prostate cancers, PCA1 and PCA2, which harbor AX747630 (*Homo sapiens* cDNA FLJ35294 fis, clone PROST2008724)-ETV1 and TMPRSS2-ERG (transmembrane protease, serine 2-v-ets erythroblastosis virus E26 oncogene homolog (avian)) gene fusions, respectively, indicate that the ETS gene fusion had the highest score in each sample (FIG. 1a), as reported previously (Maher et al., 2009, supra; Wang et al., *Nat. Biotechnol.* 27, 1005-1011 (2009)).

In this study, five ETS gene fusion-positive and ten ETS gene fusion-negative prostate cancers (ETS gene fusion status was determined by fluorescence in situ hybridization (FISH), quantitative RT-PCR (qRT-PCR) or both) were sequenced and it was found that two ETS-negative samples, PCA3 and PCA17, each prioritized a fusion involving BRAF and RAF1 genes, key serine-threonine kinase components of the RAF signaling pathway (FIG. 1a). Whereas activating somatic mutations in the RAF kinase pathway, such as BRAF with a mutation that results in a V600E amino acid substitution (BRAFV600E), are common in melanoma, thyroid, colon and ovarian cancers (Cohen et al., *J. Natl. Cancer Inst.* 95, 625-627 (2003); Davies et al., *Nature* 417, 949-954 (2002); Wang et al., *Cancer Res.* 63, 5209-5212 (2003); Xing, *Endocr. Relat. Cancer* 12, 245-262 (2005)), activating gene fusions of pathway members have been reported less frequently and are found in subsets of relatively rare cancers (Ciampi et al. *J. Clin. Invest.* 115, 94-101 (2005); Jones et al. *Cancer Res.* 68, 8673-8677 (2008); Dessars et al. *J. Invest. Dermatol.* 127, 1468-1470 (2007)). The RAF kinase pathway is druggable, with multiple approved and investigational agents in late-stage development. Sorafenib, a US Food and Drug Administration-approved drug, was originally identified as a RAF kinase inhibitor but was subsequently found to target other kinases such as vascular endothelial growth factor receptor-2 (VEGFR-2), VEGFR-3 and platelet-derived growth factor receptor-β (Wilhelm et al. *Mol. CancerTher.* 7, 3129-3140

(2008)). An emerging lead drug candidate, PLX-4032, is highly selective for the BRAFV600E mutation and is being evaluated in people with advanced melanoma (Sala et al. *Mol. Cancer Res.* 6, 751-759 (2008)). Thus, the druggable gene fusions identified in prostate tumors PCA3 and PCA17 were characterized.

Figure 5:
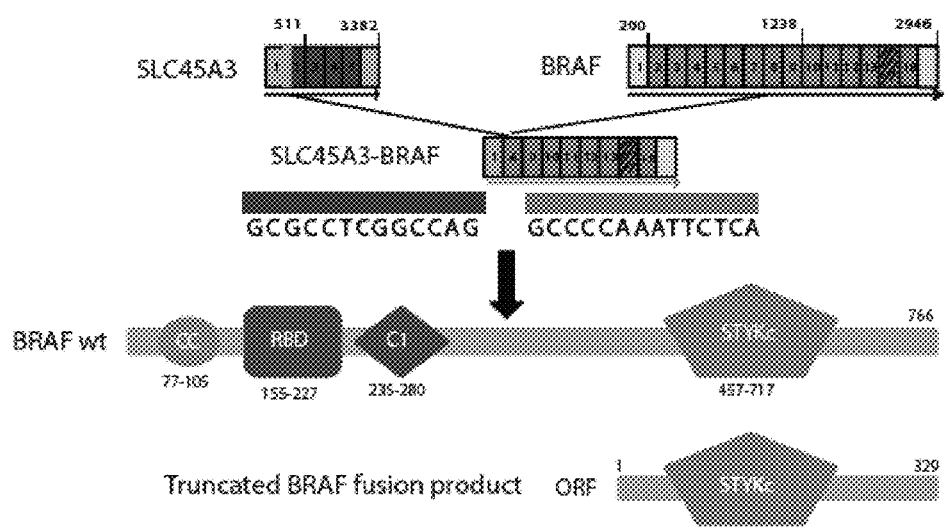
FIG. 5 shows exon and protein domain structure of BRAF and RAF1 wild type and fusion gene constructs. a, Schematic diagram showing the exon structure of wild type SLC45A3 and BRAF and SLC45A3-BRAF fusion gene in the top panel. b, Full length SLC45A3-BRAF fusion transcript (2017 bp) containing the first un-translated exon of SLC45A3 and exon 8 to the last exon of BRAF was cloned into pDEST40 vector. c, Schematic diagram showing the exon structure of wild type ESRP1 and RAF1 genes and ESRP1-RAF1 (left) and RAF1-ESRP1 (right) reciprocal fusion transcripts in the top panel.
Figure 5:
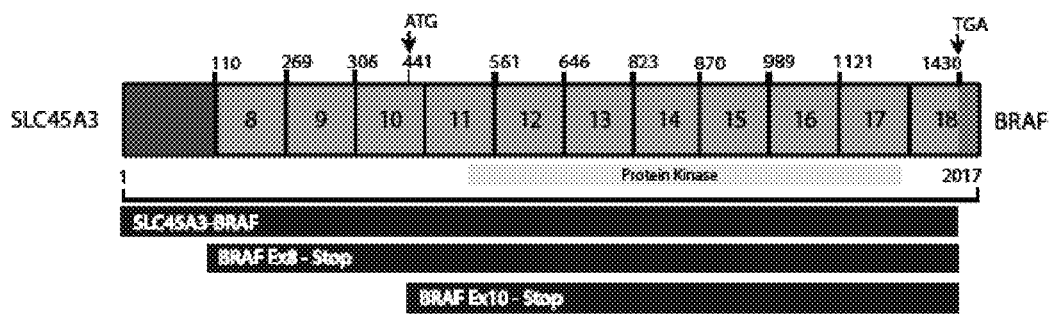
Figure 5:
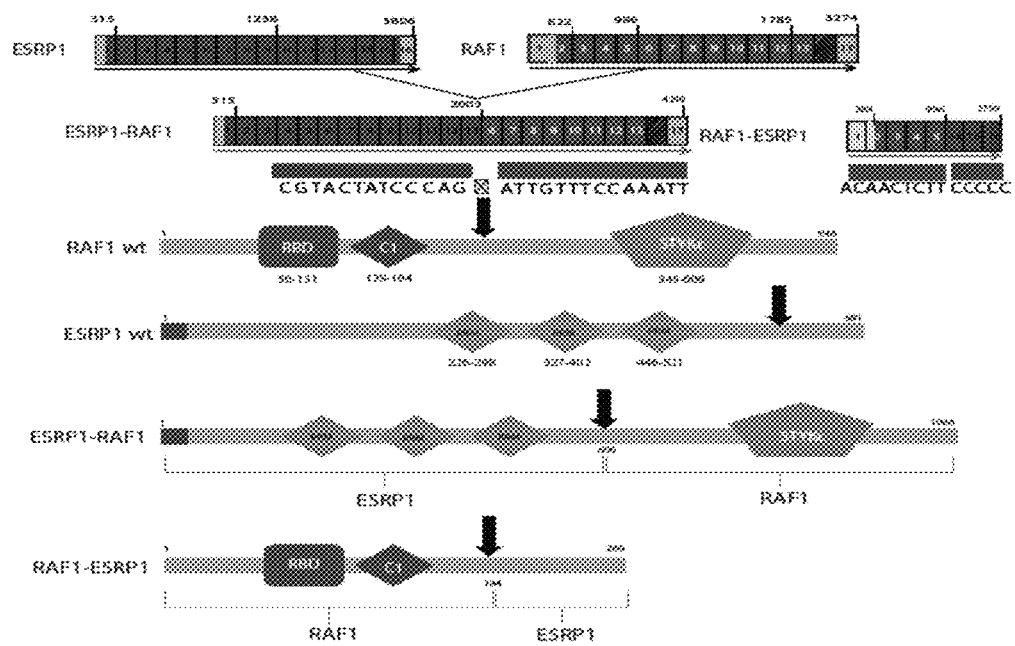
Figure 5:
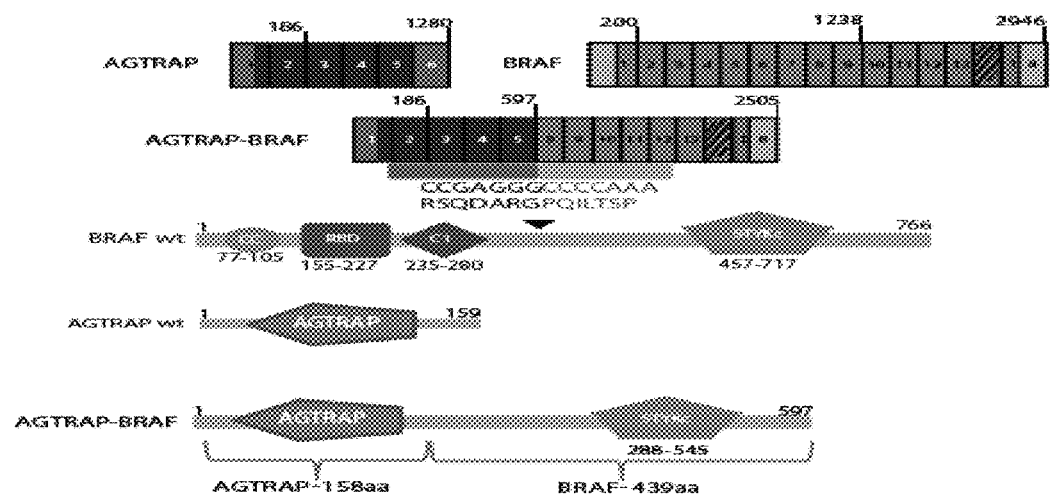
Figure 6:
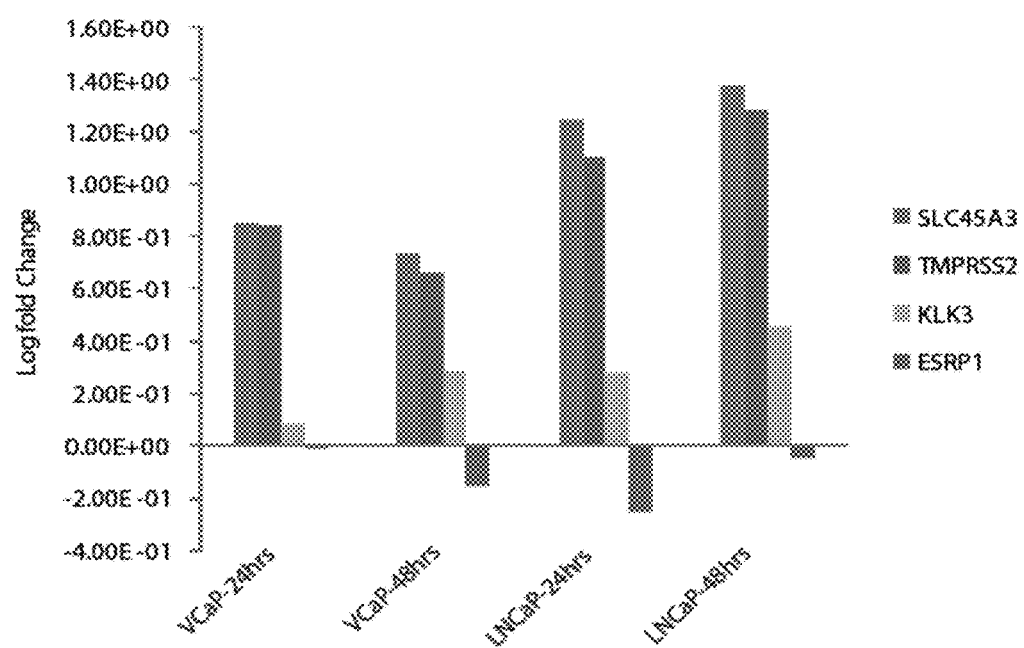
FIG. 6 shows that ESRP1, the 5' fusion partner of RAF1 is not regulated by androgen.
Figure 7:
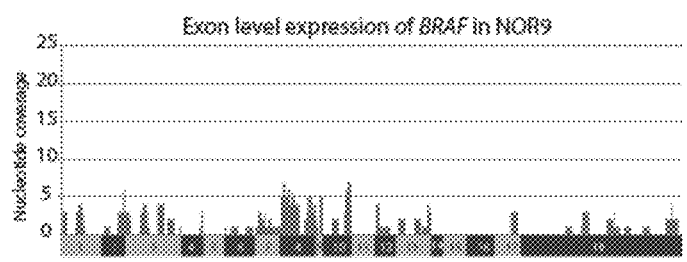
FIG. 7 shows RNA-seq exon coverage and qRT-PCR validation of BRAF exons in normal, metastatic prostate samples and index case (PCA3). a. Exons are shown at the bottom in alternating shades of grey. b. qRT-PCR using exon spanning primers showing high level expression of BRAF exons 8-18 relative to the exons 1-7 in PCA3.
Figure 7:
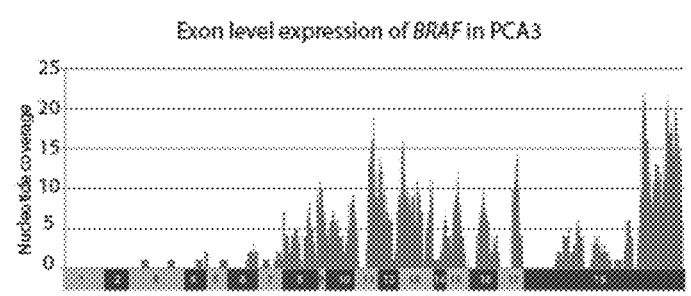
Figure 7:
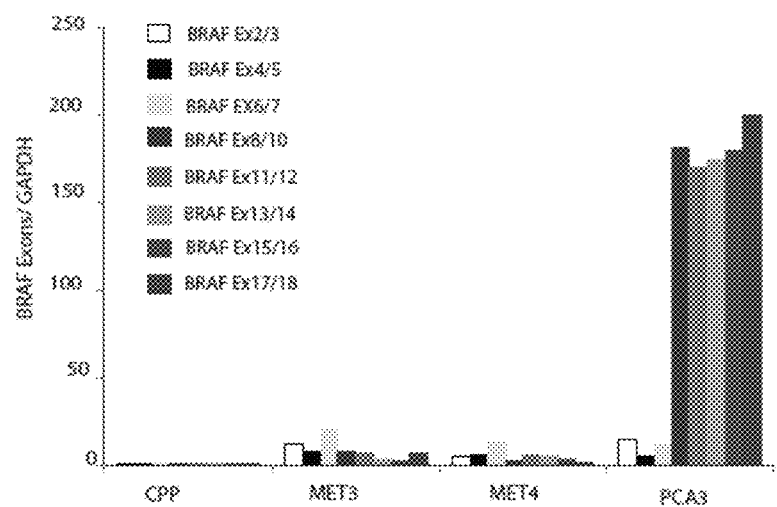

The first case, PCA3, revealed an interchromosomal rearrangement resulting in the fusion of untranslated exon 1 of SLC45A3 with exon 8 of BRAF (FIG. 1b). SLC45A3 is a prostate-specific, androgen responsive gene that has been found fused to ERG (Esgueva et al. *Mod. Pathol.* 23, 539-546 (2010); Han et al. *Cancer Res.* 68, 7629-7637 (2008)) ETV118, ETV519 and ELK4 (Maher et al. *Nature* 458, 97-101 (2009); Rickman et al. *Cancer Res.* 69, 2734-2738 (2009)) in a subset of prostate tumors. The predicted open reading frame encodes 329 amino acids of the C-terminal portion of BRAF (FIG. 5a), retaining the kinase domain but losing the N-terminal RAS-binding domain, indicating that the mutant protein is constitutively active. Having inherited promoter regulatory elements from SLC45A3, this BRAF fusion is likely under androgen regulation (FIG. 6). Consistent with this, the C-terminal exons of BRAF (8-18) present in the fusion protein are overexpressed in PCA3 tumor relative to normal prostate and other prostate cancers (FIG. 7a,b). The second case, PCA17, revealed two highly expressed gene fusions involving ESRP1 and RAF1 (FIG. 1c,d), formed by a balanced reciprocal translocation. ESRP1 is a splicing factor that regulates the formation of epithelial cell-specific isoforms of mRNA (Warzecha et al., *Mol. Cell* 33, 591-601 (2009)), whereas RAF1 (or CRAF) is a serine-threonine protein kinase.

The ESRP1-RAF1 fusion transcript involves the fusion of exon 13 of ESRP1 to exon 6 of RAF1 (FIG. 1c). The predicted open reading frame encodes a 120-kDa fusion protein comprised of the majority of ESRP1, including its three RNA recognition motifs, fused to the C-terminal kinase domain of RAFT (FIG. 6c). Loss of the RAS-binding domain of RAFT indicates that this fusion protein is constitutively active.

In addition to ESRP1-RAF1, the reciprocal gene fusion RAF1-ESRP1, produced from the same genomic rearrangement in PCA17, was also detected. The RAF1-ESRP1 transcript involves the fusion of exon 5 of RAF1 with exon 14 of ESRP1 (FIG. 1d), which encodes a predicted 30-kDa protein comprised of the RAS-binding domain of RAF1 fused to 194 amino acids from the C terminus of ESRP1 (FIG. 5c). Unlike SLC45A3-BRAF, ESRP1-RAF1 is predicted to not be regulated by androgen, as wild-type ESRP1 is not androgen regulated (FIG. 6).

Figure 2:
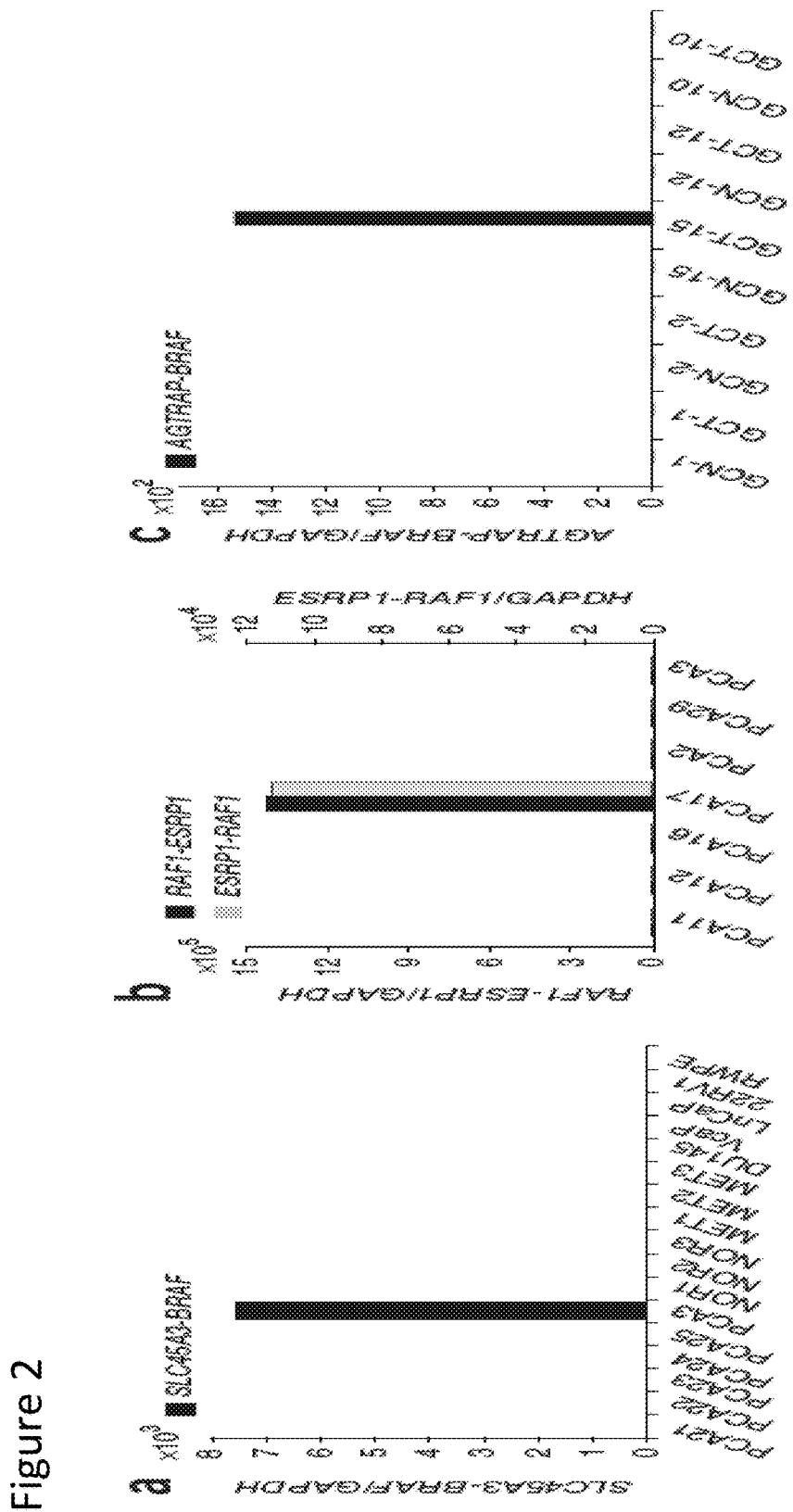
FIG. 2 shows experimental validation of the SLC45A3-BRAF, ESRP1-RAF1 and RAF1-ESRP1 and AGTRAP-BRAF gene fusions in the prostate tumor samples and prostate cancer cell lines (DU145, VCaP, LnCaP and 22RV1) and RWPE as negative controls. (a-c) Expression of SLC45A3-BRAF gene fusion in PCA3 (a), ESRP1-RAF1 and RAF1-ESRP1 fusions in PCA17 (b) and AGTRAP-BRAF fusion in GCT15 (c) tumors are validated by qRT-PCR by normalizing against glyceraldehyde 6-phosphate dehydrogenase (GAPDH) values in each sample. (d) FISH validation of SLC45A3-BRAF (left) and ESRP1-RAF1 (right) gene fusions in PCA3 and PCA17 tumors, respectively. (e) FISH validation of the BRAF rearrangement in GCT15 tumor (left and BRAF 5' deletion (right). (f) FISH validation of the BRAF rearrangement in melanoma case MEL23 (left) and RAFT rearrangement in melanoma case MEL24 (right). (g) Expression of the 120-kDa ESRP1-RAF1 fusion protein in the index case PCA17. (h) Expression of a 70-kDa AGTRAP-BRAF fusion protein in case GCT15.
Figure 2:
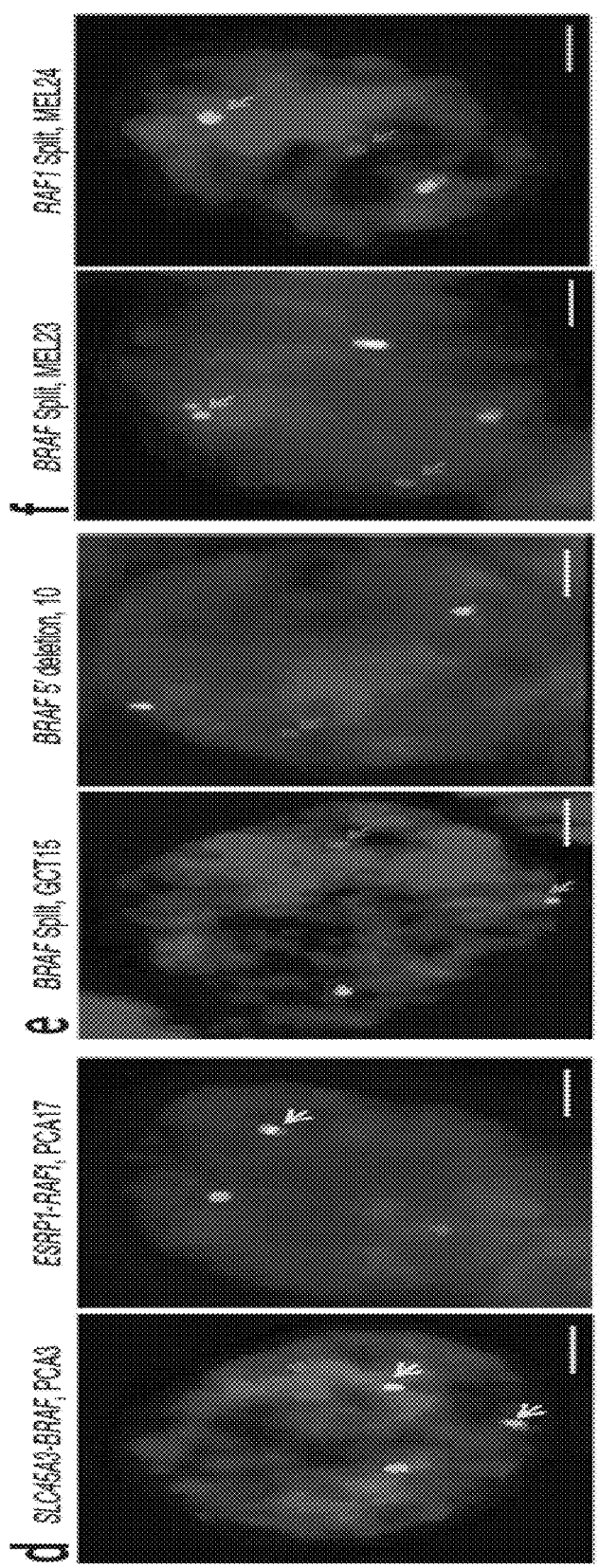
Figure 2:
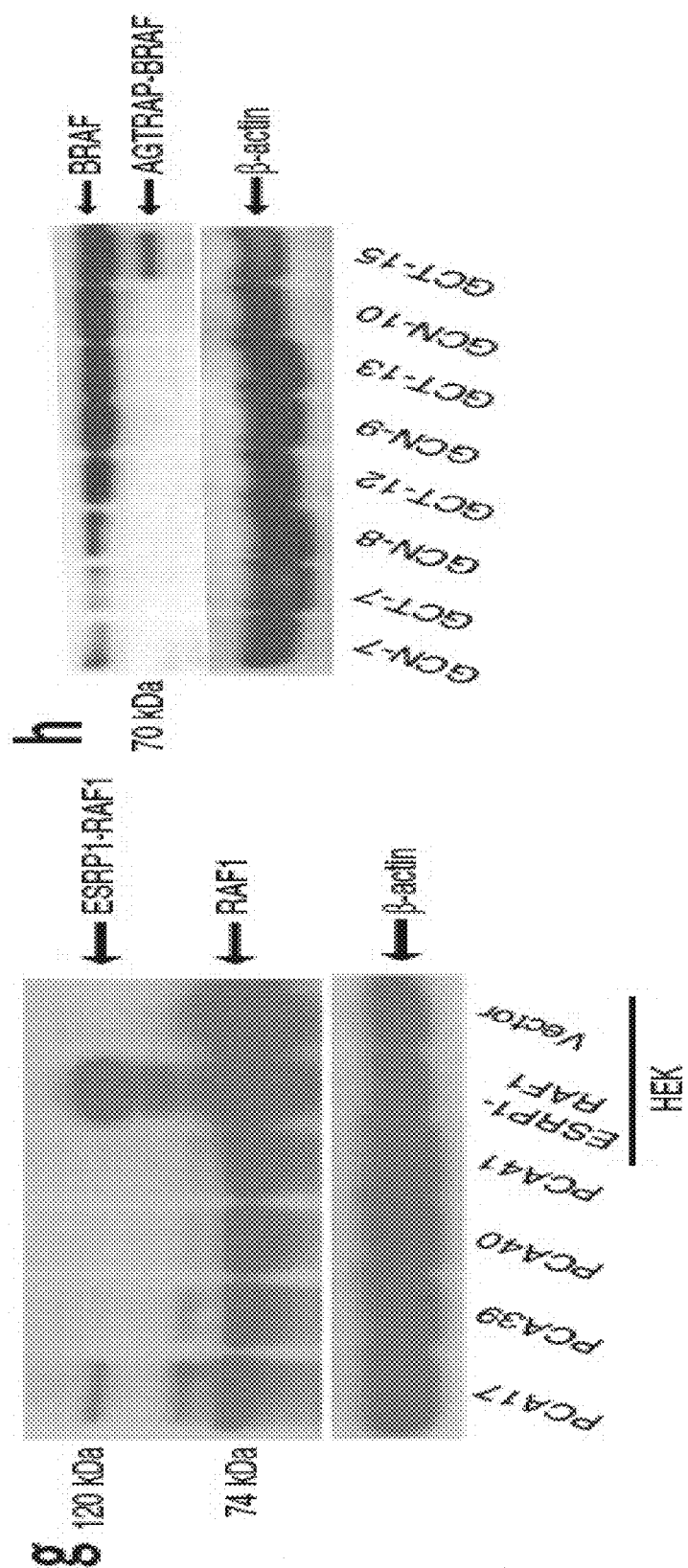
Figure 8:
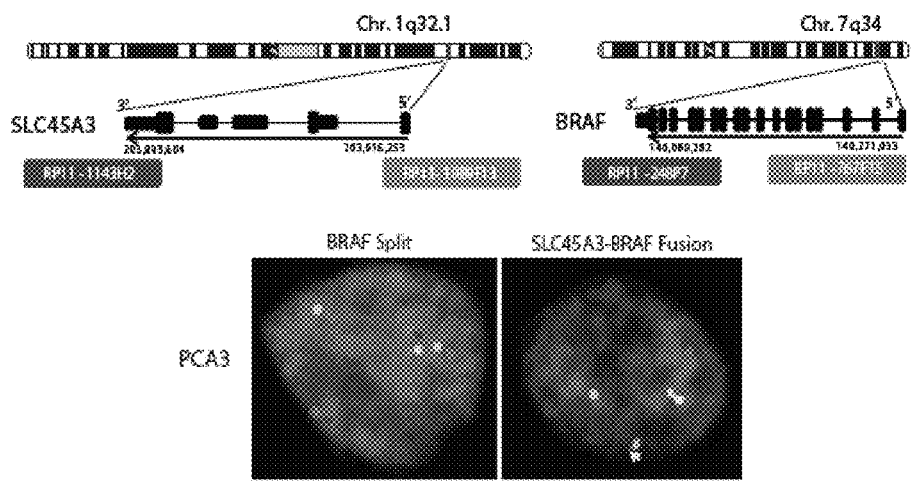
FIG. 8 shows genomic organization and FISH validation of BRAF and RAF1 gene rearrangement. a, Schematic diagrams showing the genomic location of SLC45A3 (left) and BRAF (right) genes on chromosome 1q32.1 and 7q34 respectively. b, Schematic diagrams showing the genomic location of ESRP1 (right) and RAF1 (left) genes on chromosome 8q22.1 and 3p25.1 respectively.
Figure 8:
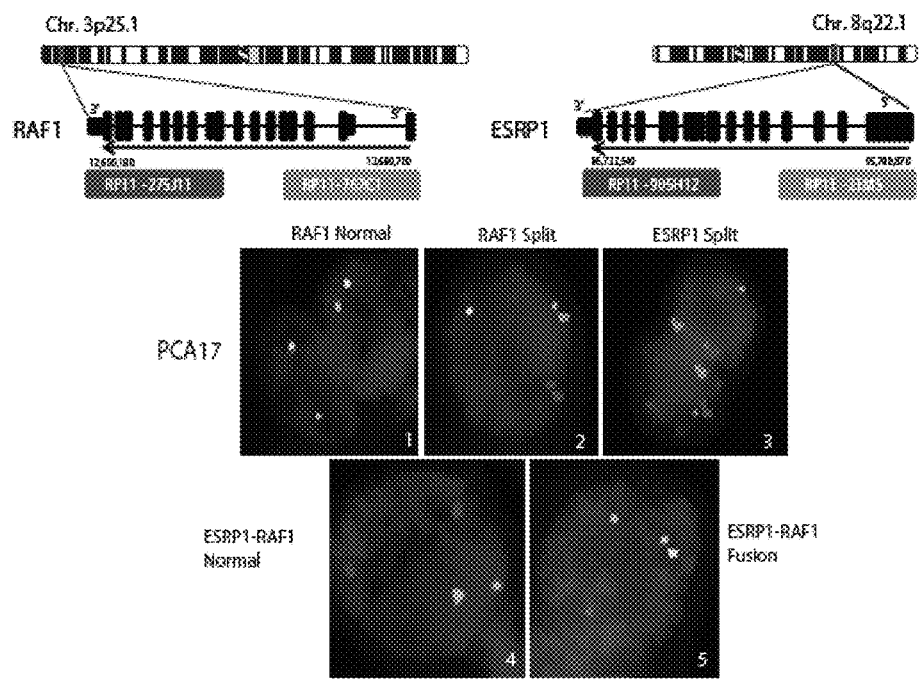
Figure 9:
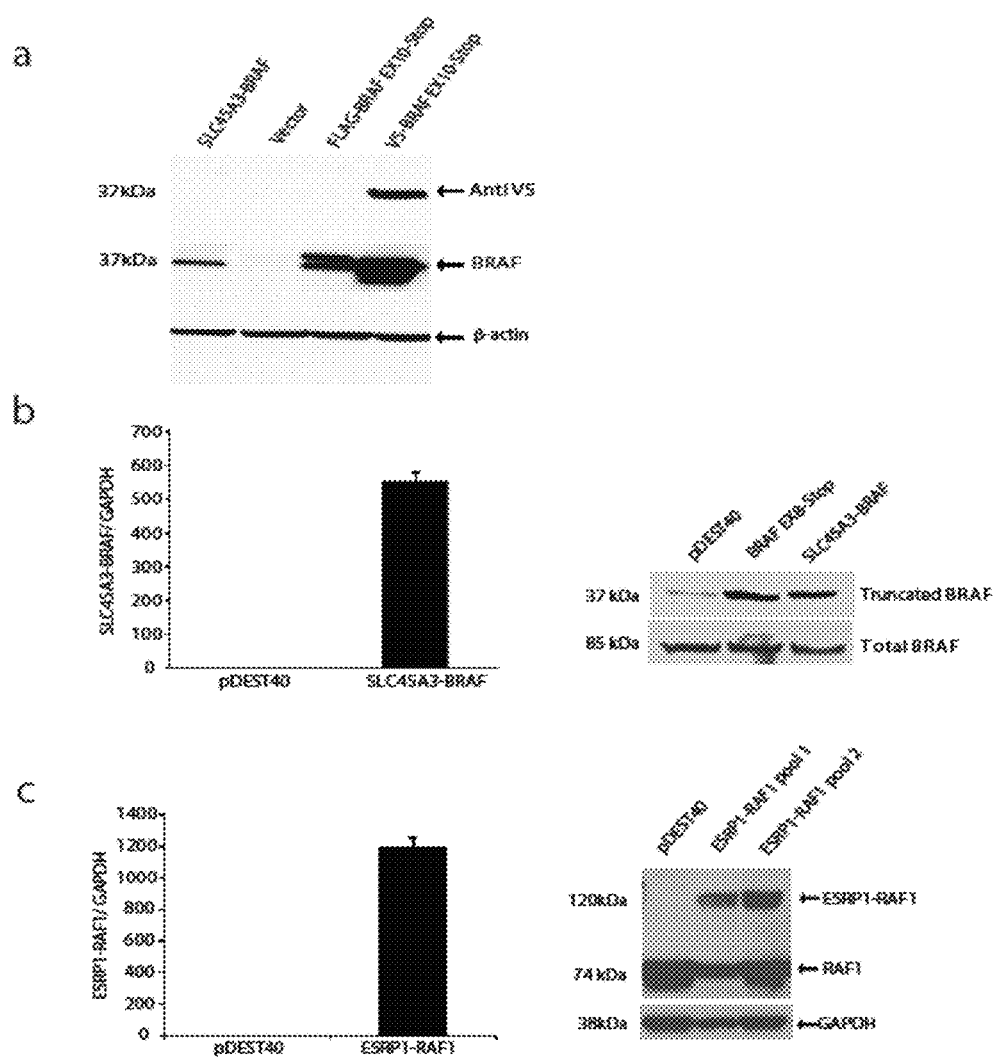
FIG. 9 shows validation of expression constructs by qRT-PCR and western blot analysis. a. SLC45A3-BRAF expression constructs with N-terminus Flag tag and C-terminus V5 tag were transfected in HEK293 cells. b. Stable expression of BRAF EX8-Stop and SLC45A3-BRAF fusion construct in RWPE cells was validated by qRT-PCR and western blot analysis using BRAF specific antibody. c. Stable expression of ESRP1-RAF1 fusion construct in RWPE cells was validated by qRT-PCR (left panel) and western blot analysis (right panel) using RAF1 specific antibody.

Next, the SLC45A3-BRAF fusion was confirmed by fusion-specific qPCR in PCA3 tumor. Rearrangement at the DNA level was validated by FISH and confirmed the presence of two copies of rearranged chromosomes by break-apart (FIG. 8a) and fusion (FIG. 2) assays. Expression of the SLC45A3-BRAF fusion gene in HEK293 cells and stable expression in RWPE (human benign immortalized prostate epithelial cell line) cells generated a 37-kDa protein (FIG. 9a,b).

ESRP1-RAF1 and RAF1-ESRP1 were also validated by qRTPCR (FIG. 2b) in the index PCA17 tumor. FISH confirmed the DNAlevel rearrangement and fusion of the ESRP1 and RAF1 loci (FIG. 2d and FIG. 8b). Expression of a 120-kDa ESRP1-RAFT fusion protein was observed in PCA17 tumor and upon overexpression in HEK293 (FIG. 2g) and RWPE cells (FIG. 9c).

BRAF and RAF1 rearrangement frequencies were estimated in three independent prostate cancer clinical cohorts by FISH on tissue microarrays with break-apart probes. Out of 349 prostate cancer cases that were evaluable by FISH, six cases had an aberration at the BRAF locus (five rearrangements and one deletion of the 5' probe), and four of 450 cases showed rearrangement at the RAF1 locus (one rearrangement and three deletions of the 3' probe). Other than the index cases PCA3 and PCA17, these cases did not show rearrangement of the SLC45A3 or ESRP1 loci, indicating fusions involving multiple 5' partners, similar to ETV1 fusions in prostate cancer (Tomlins et al. *Nature* 448, 595-599 (2007)). A majority of the cases that were positive for rearrangements of BRAF or RAF1 had advanced features including high Gleason score and castration resistance. All of the cases were negative for ETS gene rearrangement (except MET37, which had an ERG rearrangement), indicating that these aberrations occur predominantly in ETS-negative prostate cancers (Table 1a).

The analysis of BRAF and RAF1 rearrangements was extended to other solid tumors by using break-apart FISH probes on tissue microarrays of breast (n=49), endometrial (n=26), gastric (n=85), melanoma (n=131) and liver (n=42) tumors. Similar to the case in prostate cancer, a 1-2% incidence of BRAF aberrations was found in gastric cancer (2 of 105) (FIG. 2e) and one case each of BRAF and RAF1 rearrangement in melanoma (2 of 131) (FIG. 2f). In the gastric cancer index case GCT-15, paired-end transcriptome sequencing revealed that exon 8 of the BRAF gene was fused with exon 5 of AGTRAP (encoding angiotensin II, type I receptor-associated protein) (FIG. 1e). The AGTRAP-BRAF fusion transcript was validated by qRT-PCR (FIG. 2c) and the DNA-level rearrangement by FISH analysis (FIG. 2f). The AGTRAP-BRAF fusion resulted in the formation of a 597-amino acid fusion protein with the C-terminal kinase domain of BRAF fused to the N-terminal angiotensin II, type 1 receptor-associated domain of AGTRAP (FIG. 5d). The expression of the predicted AGTRAP-BRAF fusion protein was confirmed by immunoblot analysis of the index tumor GCT-15 (FIG. 2h).

Considering the prevalence of oncogenic mutations in BRAF in various cancer types, the BRAFV600E mutation was screened for by pyrosequencing in 274 prostate samples, 23 gastric cancer samples, two gastroesophageal cancer samples and 34 melanoma samples. It was found that 20 of 34 (59%) melanoma samples, one of 25 gastroesophageal cancers and zero of 274 prostate samples were positive for the BRAFV600E mutation. The present disclosure is not limited to a particular mechanism. Indeed, an understanding of the mechanism is not necessary to practice the present disclosure. Nonetheless, none of the RAF pathway gene rearrangement-positive prostate cancers, gastroesophageal cancers and melanomas identified herein harbored BRAFVa1600E mutations, indicating genomic rearrangement, rather than mutation, as a mechanism for RAF gene activation in a subset of solid tumors. In an Asian cohort, 10% of prostate cancer cases have been reported to be positive for BRAFV600E mutations (Cho et al. *Int. J. Cancer* 119, 1858-1862 (2006)). No BRAFVal600 mutations were found in the prostate cancer cohorts, which is consistent with a recently published study (zero of 95 prostate cancers were positive for Val600) (MacConaill et al. *PLoS One* 4, e7887 (2009)).

Figure 3:
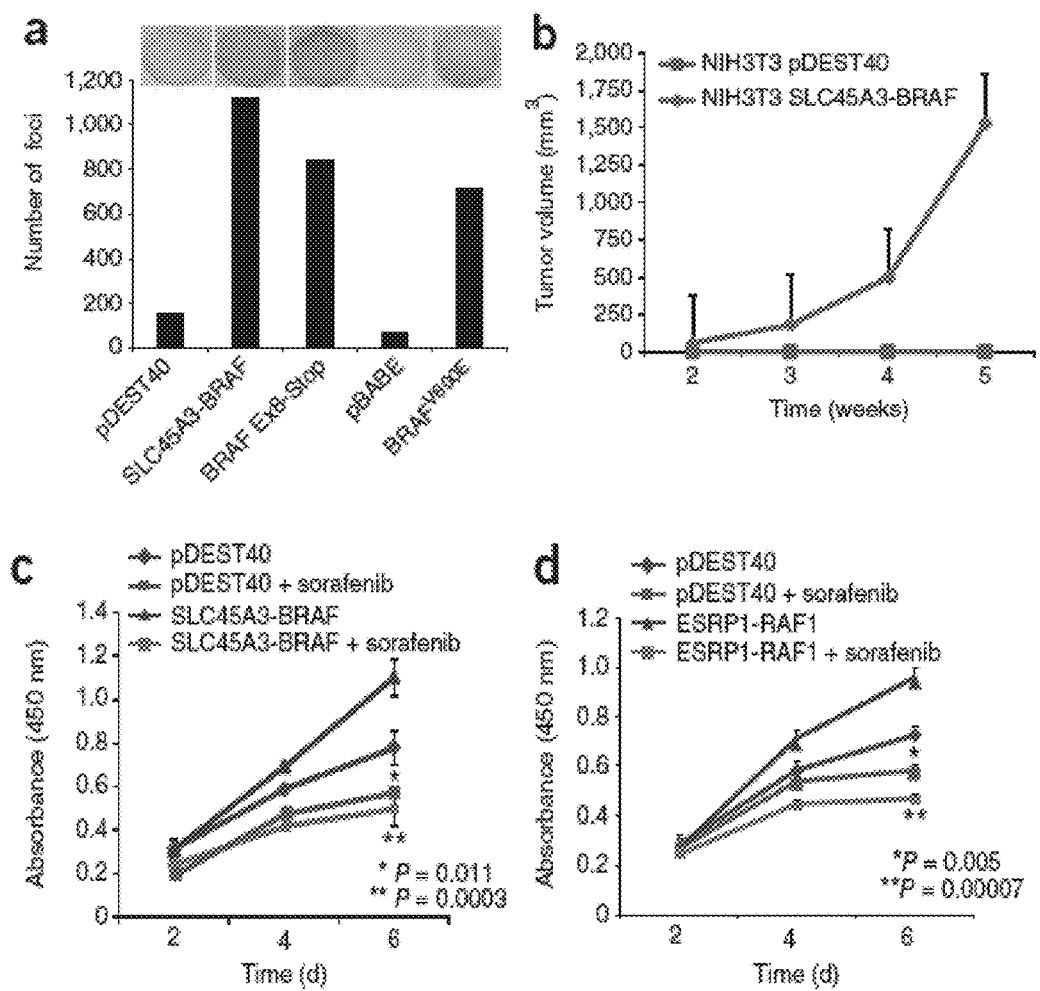
FIG. 3 shows oncogenic properties of SLC45A3-BRAF and ESRP1-RAF1 gene fusions. (a) Foci formation by SLC45A3-BRAF, BRAFV600E and vector control (pDEST40 and pBABE) constructs in NIH3T3 cells. (b) Tumor growth in nude mice implanted with NIH3T3 cells overexpressing SLC45A3-BRAF or pDEST40 vector control. (c,d) Cell proliferation assay using RWPE cells overexpressing SLC45A3-BRAF (c) and ESRP1-RAF1 (d) gene fusions.
Figure 10:
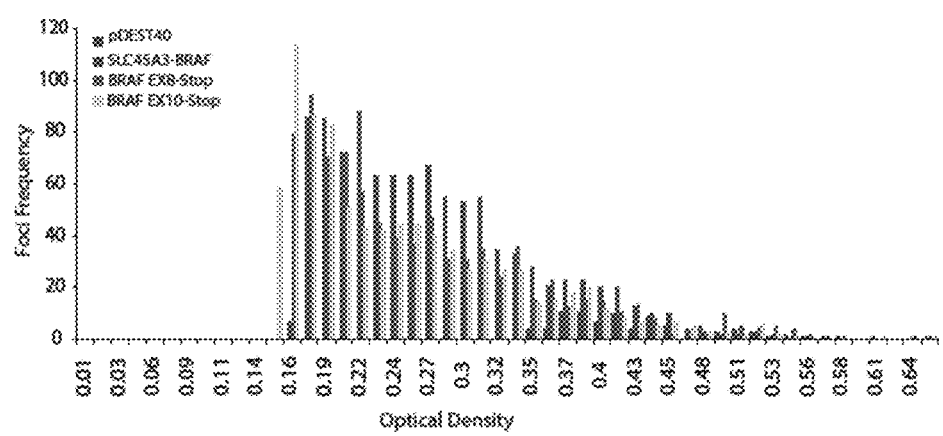
FIG. 10 shows a, Comparison of the foci frequencies of NIH3T3 cells expressing fusion transcript SLC45A3-BRAF, BRAF Ex8-Stop and BRAF Ex10-Stop and pDEST40 vector. b, Stable RWPE cells over-expressing SLC45A3-BRAF form small tumors in Balb C nu/nu mice.
Figure 10:
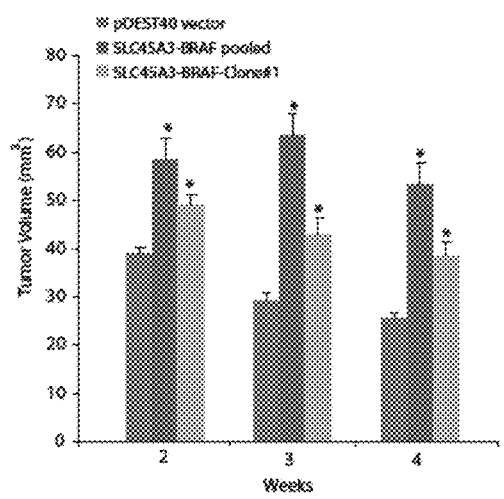

The functional relevance of the fusions involving RAF pathway members in prostate cancer was examined. First, the SLC45A3-BRAF fusion was examined in mouse fibroblast NIH3T3 cells, a system classically used to study RAS and RAF biology (Garte et al., *Cancer Res.* 47, 3159-3162 (1987)). Overexpression of SLC45A3-BRAF (FIG. 5b) or mutant BRAFV600E showed a marked increase in the number of foci as compared to vector controls (FIG. 3a). The foci assay data were further validated by automated colony counting (FIG. 10a). NIH3T3 cells overexpressing SLC45A3-BRAF formed rapidly growing tumors in nude mice (FIG. 3b); however, NIH3T3 cells overexpressing ESRP1-RAF1 did not form tumors.

Figure 4:
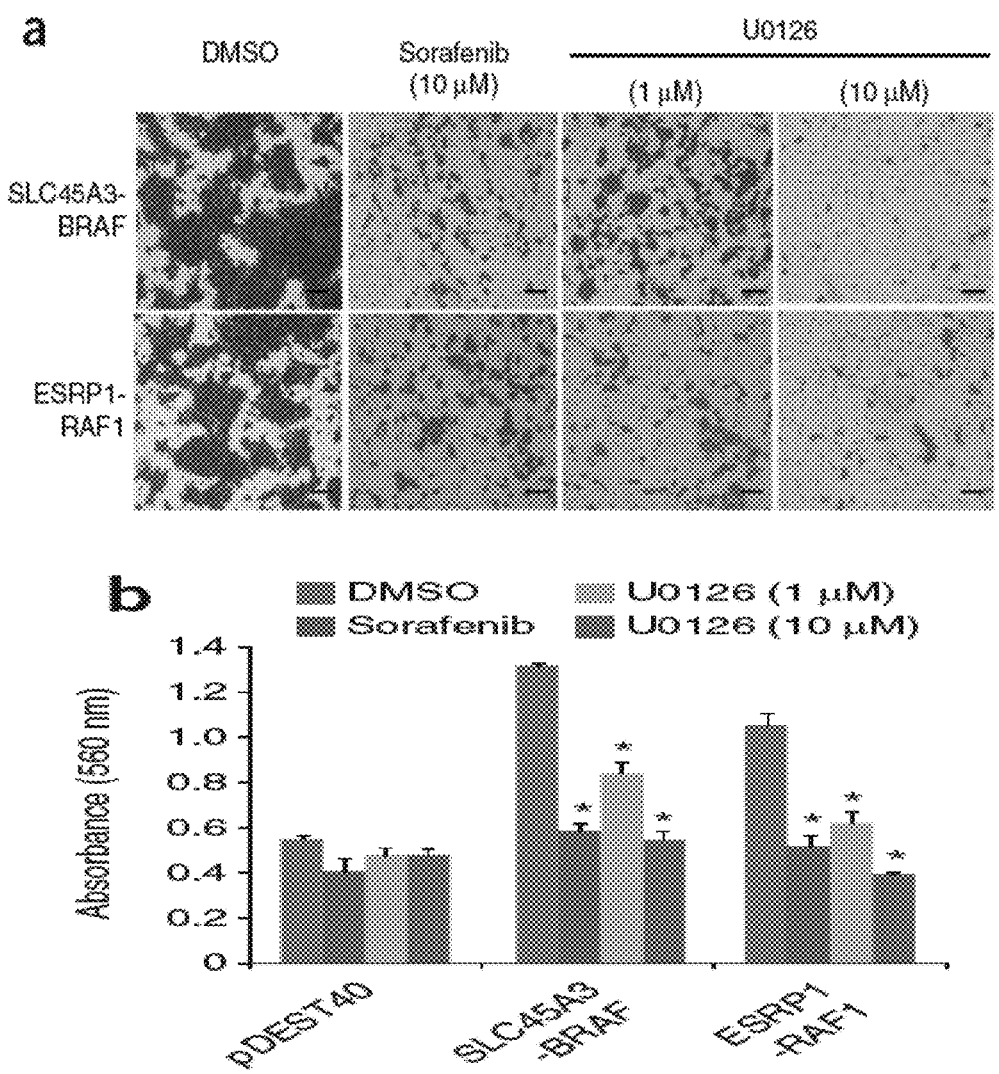
FIG. 4 shows that RAF and MEK inhibitors block SLC45A3-BRAF or ESRP1-RAF1 gene fusion-mediated oncogenic phenotypes. (a,b) SLC45A3-BRAF- or ESRP1-RAF1-mediated cell invasion in RWPE prostate cells is sensitive to sorafenib (10 μM) or the MEK inhibitor U0126 (1 or 10 μM). (a) Crystal violet staining of cells after invasion through Matrigel. (b) Quantification of cells by absorbance. (c,d) Photomicrographs (c) or quantification (d) of SLC45A3-BRAF- or ESRP1-RAF1-induced anchorage-independent colony growth in soft agar, which was sensitive to sorafenib or U0126. (e) Evaluation of the downstream signaling pathways activated by the SLC45A3-BRAF or ESRP1-RAF1 gene fusions in RWPE prostate cells.
Figure 4:
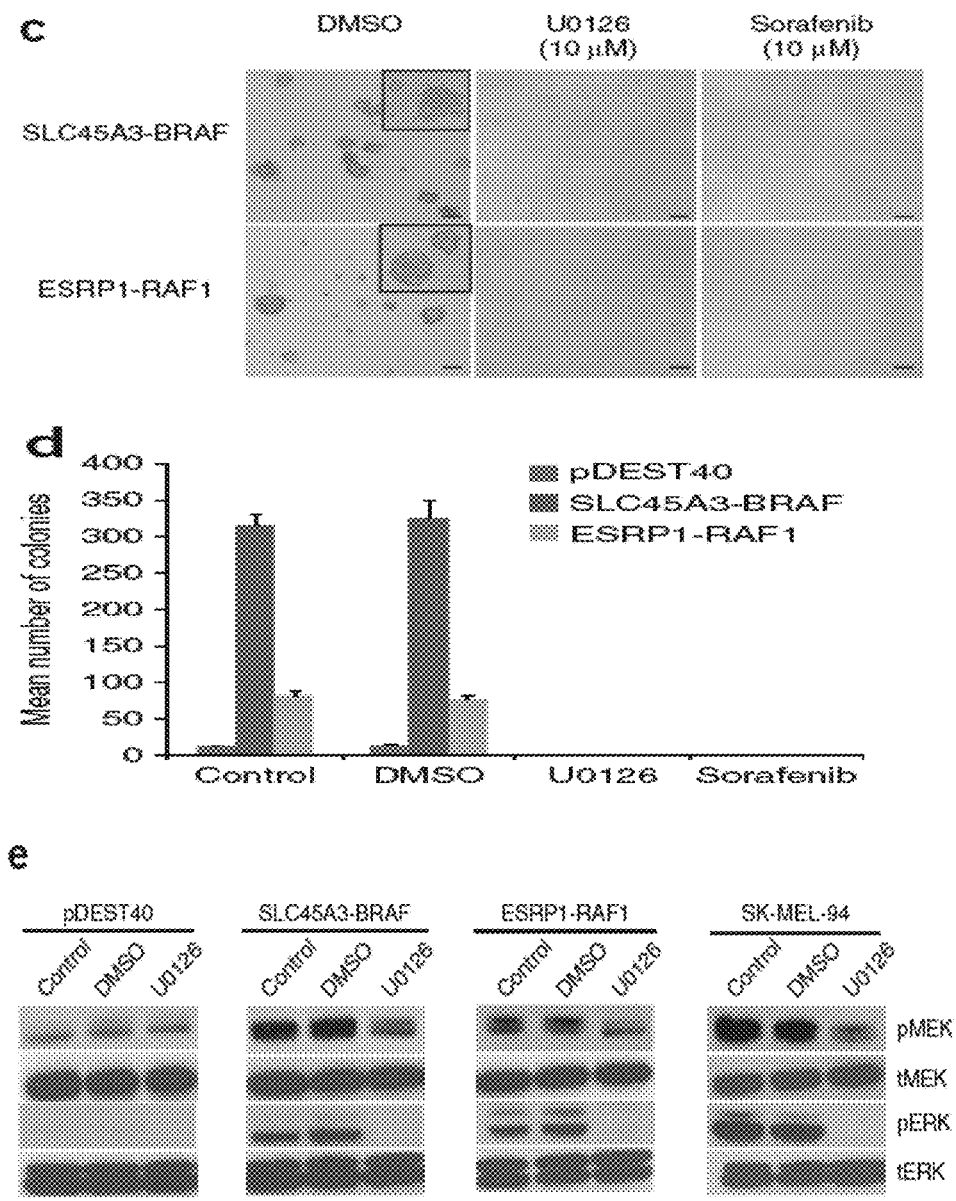

To examine the role of these fusions in the prostate, SLC45A3-BRAF or ESRP1-RAF1 was overexpressed in RWPE cells; both gene fusions resulted in increased cell proliferation that was sensitive to the RAF kinase inhibitor sorafenib (FIG. 3c,d). A marked increase in cell invasion of RWPE cells expressing either SLC45A3-BRAF or ESRP1-RAF1, which was sensitive to sorafenib or the MEK inhibitor U0126 was also observed (FIG. 4a,b). Furthermore, RWPE cells expressing either SLC45A3-BRAF or ESRP1-RAF1 formed anchorage independent colonies in soft agar, which were again sensitive to RAF and MEK inhibitors (FIG. 4c,d). Finally, RWPE cells stably expressing SLC45A3-BRAF formed small tumors in immunodeficient mice that regressed after 4 weeks (FIG. 10b).

Figure 11:
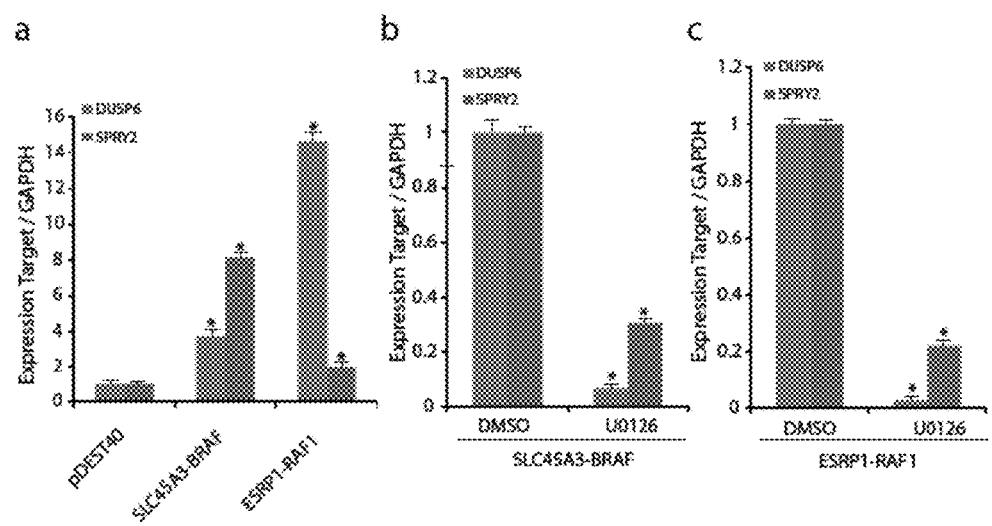
FIG. 11 shows down-regulation of genes involved in the MEK pathway after U0126 treatment. a, Stable RWPE cells expressing SLC45A3-BRAF or ESRP1-RAF1 showed increase in DUSP6 or SPRY2 mRNA expression as compared to pDEST40 vector. b, c, MEK inhibitor (U0126, 10 mM) treatment for 2 hours in Keratinocyte-supplement free media significantly decreases expression of these genes in RWPE cells expressing SLC45A3-BRAF or ESRP1-RAF1.

The RAF family is known to have a pivotal role in transducing signals from RAS to downstream kinases, mitogen-activated protein kinase and extracellular signal-regulated kinase (ERK) kinase (MEK1/2) and ERK1/2 (Hoeflich et al. Clin. Cancer Res. 15, 4649-4664 (2009)). Overexpression of SLC45A3-BRAF or ESRP1-RAF1 in RWPE cells induced MEK and ERK phosphorylation, which was sensitive to treatment with a MEK inhibitor (FIG. 4e). The MEK inhibitor also decreased MEK1/2 and ERK1/2 phosphorylation in a control BRAFV600E mutation-positive human melanoma cell line, SK-MEL-94, consistent with previous data (Pratilas et at Proc. Natl. Acad. Sci. USA 106, 4519-4524 (2009). It was also found that an increase in mRNA expression of genes encoding the feedback effectors dual-specificity phosphatase-6 and sprouty homolog-2 in RWPE cells stably expressing SLC45A3-BRAF or ESRP1-RAF1, and the expression of these feedback effectors was decreased upon MEK inhibitor treatment (FIG. 11).

The results emphasize the key role of the RAF pathway in prostate cancer development and progression. Although it is rare in human prostate tumors, activation of the BRAF pathway via the V600E mutation in genetically engineered mice has been shown to cooperate with other lesions to initiate the development of invasive prostate cancer (Jeong et al. PLoS One 3, e3949 (2008). ETS transcription factors, including ETV1, have been shown to be downstream targets activated by the RAS-RAF-MAPK signaling pathway (Janknecht, Mol. Cell. Biol. 16, 1550-1556 (1996); Bosc et al., J. Cell. Biochem. 86, 174-183 (2002)).

Sequencing tumor transcriptomes and genomes identifies rare targetable fusions across cancer types. Screening for RAF kinase fusions is useful in identifying people with cancer who benefit from treatment with RAF kinase inhibitors. The identification of RAF pathway gene rearrangements in 1-2% of prostate cancers, gastric cancers and melanomas supports the general principle that cancers should be classified by driving molecular events, rather than by organ site, in the context of rational targeted therapy.

TABLE 1

Clinicopathological characteristics of the index cases in prostate, gastric cancer and melanoma with BRAF and RAF1 gene rearrangement a

|   | Sample ID | Age | Diagnosis | Gleason Score | CR | ERG rearrangement | BRAF rearrangement | RAF1 rearrangement | Fusion |
|---|---|---|---|---|---|---|---|---|---|
| BRAF | PCA3 | 59 | PCA | 4 + 4 | − | − | + | − | SLC45A3-BRAF |
|  | PCA44 | 75 | PCA | 4 + 4 | + | − | + | − |  |
|  | PCA45 | NA | PCA | 4 + 4 | + | − | + | − |  |
|  | PCA46 | 89 | PCA | 5 + 4 | + | − | + | − |  |
|  | MET37 | 63 | MET | 4 + 5 | + | + | + | − |  |
|  | PCA47 | 62 | PCA | 4 + 3 | − | − | 5'del | − |  |
| RAF1 | PCA17 | NA | PCA | 3 + 4 | − | − | − | + | ESRP1-RAF1 |
|  | PCA48 | 66 | PCA | 3 + 3 | − | − | − | 3'del |  |
|  | MET36 | 62 | MET | NA | + | − | − | 3'del |  |
|  | PCA49 | NA | PCA | NA | − | − | − | 3'del |  | b

| Sample ID | Age | Sex | Diagnosis | BRAF rearrangement | RAF1 Rearrangement | Fusion |
|---|---|---|---|---|---|---|
| GCT15 | 61 | F | Gastric adenocarcinoma | + | − | AGTRAP-BRAF |
| GC#10 | 51 | F | Adenocarcinoma of GE junction | 5'del | − | − |
| MEL23 | 58 | M | Metastatic Melanoma | + | − | − |
| MEL24 | 88 | F | Metastatic Melanoma | − | + | − |

CR: Castration-resistant; PCA, clinically localized prostate cancer; MET, metastatic prostate cancer Although a variety of embodiments have been described in connection with the present disclosure, it should be understood that the claimed invention should not be unduly limited to such specific embodiments. Indeed, various modifications and variations of the described compositions and methods of the invention will be apparent to those of ordinary skill in the art and are intended to be within the scope of the following claims.

We claim:

1. A composition comprising an oligonucleotide probe that hybridizes to a junction of a chimeric genomic DNA or a chimeric mRNA, wherein a 5' portion of the chimeric genomic DNA or the chimeric mRNA is from an SLC45A3 gene and a 3' portion of the chimeric genomic DNA or the chimeric mRNA is from a RAF family member gene.

2. The composition of claim 1 wherein the RAF family member gene is BRAF.

3. The composition of claim 1 wherein the 3' portion of the chimeric genomic DNA or the chimeric mRNA comprises a wild-type sequence of the RAF family member gene.

4. The composition of claim 1 further comprising a chimeric genomic DNA or a chimeric mRNA, wherein a 5' portion of the chimeric genomic DNA or the chimeric mRNA is from an SLC45A3 gene and a 3' portion of the chimeric genomic DNA or the chimeric mRNA is from a RAF family member gene.

5. The composition of claim 1 wherein the 3' portion of the chimeric genomic DNA or the chimeric mRNA comprises exon 8 of BRAF.

6. The composition of claim 1 wherein the chimeric genomic DNA or the chimeric mRNA comprises exon 1 of SLC45A3 fused to exon 8 of BRAF.

7. The composition of claim 1 wherein the oligonucleotide probe is labeled.

8. The composition of claim 4 wherein the oligonucleotide probe is hybridized to said chimeric genomic DNA or said chimeric mRNA.

\* \* \* \* \*

UNITED STATES PATENT AND TRADEMARK OFFICE
CERTIFICATE OF CORRECTION

PATENT NO. : 9,567,644 B2
APPLICATION NO. : 14/589543
DATED : February 14, 2017
INVENTOR(S) : Arul Chinnaiyan, Nallasivam Palanisamy and Shanker Kalyana-Sundaram It is certified that error appears in the above-identified patent and that said Letters Patent is hereby corrected as shown below:

In the Claims

Column 55, Lines 55-61:
Claim 1 reads: "A composition comprising an oligonucleotide probe that hybridizes to a junction of a chimeric genomic DNA or a chimeric mRNA, wherein a 5' portion of the chimeric genomic DNA or the chimeric mRNA is from an SLC45A3gene and a 3' portion of the chimeric genomic DNA or the chimeric mRNA is from a RAF family member gene."

Claim 1 should read: "A composition comprising an oligonucleotide probe that hybridizes to a junction of a chimeric genomic DNA or a chimeric mRNA, wherein a 5' portion of the chimeric genomic DNA or the chimeric mRNA is from an SLC45A3 gene and a 3' portion of the chimeric genomic DNA or the chimeric mRNA is from a RAF family member gene."

Signed and Sealed this
Twenty-fifth Day of April, 2017

Michelle K. Lee
*Director of the United States Patent and Trademark Office*

SEQUENCE LISTING

<160> NUMBER OF SEQ ID NOS: 51

<210> SEQ ID NO 1
<211> LENGTH: 18
<212> TYPE: DNA
<213> ORGANISM: Artificial Sequence
<220> FEATURE:
<223> OTHER INFORMATION: Synthetic

<400> SEQUENCE: 1
agccgcgcgc ctcggcca                                                18

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
atcaggaatc tcccaatcat cact                                         24

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
gtaccagccc cacccctcta tcc                                          23

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
tcagtggaca ggaaacgcac cata                                         24

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
gccccaaatt ctcaccagtc cgtc                                         24

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
tcagtggaca ggaaacgcac ca                                           22

<210> SEQ ID NO 7
<211> LENGTH: 22
<212> TYPE: DNA
<213> ORGANISM: Artificial Sequence

```
<220> FEATURE:
<223> OTHER INFORMATION: Synthetic

<400> SEQUENCE: 7
atgaaacact tggtagacgg ga                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
tcagtggaca ggaaacgcac ca                                              22

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
aacatataga ggccctattg gaca                                            24

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10
agaagatgta acggtatcca ttg                                             23

<210> SEQ ID NO 11
<211> LENGTH: 25
<212> TYPE: DNA
<213> ORGANISM: Artificial Sequence
<220> FEATURE:
<223> OTHER INFORMATION: Synthetic

<400> SEQUENCE: 11
ggagttacag tccgagacag tctaa                                           25

<210> SEQ ID NO 12
<211> LENGTH: 25
<212> TYPE: DNA
<213> ORGANISM: Artificial Sequence
<220> FEATURE:
<223> OTHER INFORMATION: Synthetic

<400> SEQUENCE: 12
cagtaagcca ggaaatatca gtgtc                                           25

<210> SEQ ID NO 13
<211> LENGTH: 25
<212> TYPE: DNA
<213> ORGANISM: Artificial Sequence
<220> FEATURE:
<223> OTHER INFORMATION: Synthetic

<400> SEQUENCE: 13
agcgttgtag tacagaagtt ccact                                           25
```

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
agatgttagg gcagtctctg cta                                              23

<210> SEQ ID NO 15
<211> LENGTH: 26
<212> TYPE: DNA
<213> ORGANISM: Artificial Sequence
<220> FEATURE:
<223> OTHER INFORMATION: Synthetic

<400> SEQUENCE: 15
tgtgcatata aacacaatag aacctg                                           26

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
ttcgattcct gtcttctgag g                                                21

<210> SEQ ID NO 17
<211> LENGTH: 23
<212> TYPE: DNA
<213> ORGANISM: Artificial Sequence
<220> FEATURE:
<223> OTHER INFORMATION: Synthetic

<400> SEQUENCE: 17
aaaacacttg gtagacggga ctc                                              23

<210> SEQ ID NO 18
<211> LENGTH: 24
<212> TYPE: DNA
<213> ORGANISM: Artificial Sequence
<220> FEATURE:
<223> OTHER INFORMATION: Synthetic

<400> SEQUENCE: 18
cttgtaactg ctgaggtgta ggtg                                             24

<210> SEQ ID NO 19
<211> LENGTH: 25
<212> TYPE: DNA
<213> ORGANISM: Artificial Sequence
<220> FEATURE:
<223> OTHER INFORMATION: Synthetic

<400> SEQUENCE: 19
ttgtatcacc atctccatat cattg                                            25

<210> SEQ ID NO 20
<211> LENGTH: 21
<212> TYPE: DNA
<213> ORGANISM: Artificial Sequence
<220> FEATURE:
<223> OTHER INFORMATION: Synthetic

```
<400> SEQUENCE: 20
ggatgattga cttggcgtgt a                                           21

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
ctacagtgaa atctcgatgg agtg                                        24

<210> SEQ ID NO 22
<211> LENGTH: 23
<212> TYPE: DNA
<213> ORGANISM: Artificial Sequence
<220> FEATURE:
<223> OTHER INFORMATION: Synthetic

<400> SEQUENCE: 22
tcatacagaa caattccaaa tgc                                         23

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
cgaggatacc tgtctccaga t                                           21

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
gatgcactgc ggtgaatttt t                                           21

<210> SEQ ID NO 25
<211> LENGTH: 25
<212> TYPE: DNA
<213> ORGANISM: Artificial Sequence
<220> FEATURE:
<223> OTHER INFORMATION: Synthetic

<400> SEQUENCE: 25
agtgagagag ttcaggagag tagca                                       25

<210> SEQ ID NO 26
<211> LENGTH: 27
<212> TYPE: DNA
<213> ORGANISM: Artificial Sequence
<220> FEATURE:
<223> OTHER INFORMATION: Synthetic

<400> SEQUENCE: 26
aagtataaat tttagtttgg ggaaaaa                                     27

<210> SEQ ID NO 27
```

```
<211> LENGTH: 21
<212> TYPE: DNA
<213> ORGANISM: Artificial Sequence
<220> FEATURE:
<223> OTHER INFORMATION: Synthetic

<400> SEQUENCE: 27
catgagcact gtagcaccaa a                                              21

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
agcagctgta gggaagtagc c                                              21

<210> SEQ ID NO 29
<211> LENGTH: 21
<212> TYPE: DNA
<213> ORGANISM: Artificial Sequence
<220> FEATURE:
<223> OTHER INFORMATION: Synthetic

<400> SEQUENCE: 29
gtactaccca gcaggcactc a                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetic

<400> SEQUENCE: 30
ctgggactcc actatcacca a                                              21

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
atggagcaca tacagggagc t                                              21

<210> SEQ ID NO 32
<211> LENGTH: 23
<212> TYPE: DNA
<213> ORGANISM: Artificial Sequence
<220> FEATURE:
<223> OTHER INFORMATION: Synthetic

<400> SEQUENCE: 32
ttaaatacaa acccattctt tgg                                            23

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
```
atgacggcct ctccggatta                                                  20

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
ctagaagaca ggcagcctcg                                                  20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
ccgcaggagc tatacgagtc                                                  20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
cctcgtcctt gagcttcttg                                                  20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
cccctctgtc cagatccata                                                  20

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
cccaaatctt ccttgctcag                                                  20

<210> SEQ ID NO 39
<211> LENGTH: 19
<212> TYPE: DNA
<213> ORGANISM: Artificial Sequence
<220> FEATURE:
<223> OTHER INFORMATION: Synthetic

<400> SEQUENCE: 39
atccctttgc agtcccaga                                                   19

<210> SEQ ID NO 40
<211> LENGTH: 22
<212> TYPE: DNA

```
<213> ORGANISM: Artificial Sequence
<220> FEATURE:
<223> OTHER INFORMATION: Synthetic

<400> SEQUENCE: 40
ctgtggaatt ggaatggatt tt                                          22

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
tgcaccacca actgcttagc                                             20

<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
ggcatggact gtggtcatga g                                           21

<210> SEQ ID NO 43
<211> LENGTH: 9
<212> TYPE: DNA
<213> ORGANISM: Artificial Sequence
<220> FEATURE:
<223> OTHER INFORMATION: Synthetic

<400> SEQUENCE: 43 acagwgaaa                                                          9

<210> SEQ ID NO 44
<211> LENGTH: 13
<212> TYPE: DNA
<213> ORGANISM: Artificial Sequence
<220> FEATURE:
<223> OTHER INFORMATION: Synthetic

<400> SEQUENCE: 44
gcgcctcggc cag                                                    13

<210> SEQ ID NO 45
<211> LENGTH: 14
<212> TYPE: DNA
<213> ORGANISM: Artificial Sequence
<220> FEATURE:
<223> OTHER INFORMATION: Synthetic

<400> SEQUENCE: 45
gccccaaatt ctca                                                   14

<210> SEQ ID NO 46
<211> LENGTH: 13
<212> TYPE: DNA
<213> ORGANISM: Artificial Sequence
<220> FEATURE:
<223> OTHER INFORMATION: Synthetic

<400> SEQUENCE: 46
cgtactatcc cag                                                    13
```

```
<210> SEQ ID NO 47
<211> LENGTH: 14
<212> TYPE: DNA
<213> ORGANISM: Artificial Sequence
<220> FEATURE:
<223> OTHER INFORMATION: Synthetic

<400> SEQUENCE: 47
attgtttcca aatt                                                          14

<210> SEQ ID NO 48
<211> LENGTH: 9
<212> TYPE: DNA
<213> ORGANISM: Artificial Sequence
<220> FEATURE:
<223> OTHER INFORMATION: Synthetic

<400> SEQUENCE: 48 acaactctt                                                                 9

<210> SEQ ID NO 49
<211> LENGTH: 5
<212> TYPE: DNA
<213> ORGANISM: Artificial Sequence
<220> FEATURE:
<223> OTHER INFORMATION: Synthetic

<400> SEQUENCE: 49 ccccc                                                                     5

<210> SEQ ID NO 50
<211> LENGTH: 14
<212> TYPE: DNA
<213> ORGANISM: Artificial Sequence
<220> FEATURE:
<223> OTHER INFORMATION: Synthetic

<400> SEQUENCE: 50
ccgagggccc caaa                                                          14

<210> SEQ ID NO 51
<211> LENGTH: 14
<212> TYPE: PRT
<213> ORGANISM: Artificial Sequence
<220> FEATURE:
<223> OTHER INFORMATION: Synthetic

<400> SEQUENCE: 51

Arg Ser Gln Asp Ala Arg Gly Pro Gln Ile Leu Thr Ser Pro
1               5                   10
```